US012749561B2

(12) United States Patent
Campellone et al.

(10) Patent No.: US 12,749,561 B2
(45) Date of Patent: Sep. 29, 2026

(54) DYNAMIC SELECTION OF CONFIGURATION FILES FOR APPLICATIONS IN ACCORDANCE WITH ADAPTIVE GOAL SETTING

(71) Applicant: Click Therapeutics, Inc., New York, NY (US)

(72) Inventors: Tim Campellone, Oakland, CA (US); Demetrius Johnson, San Francisco, CA (US); Chris Murphy, Glen Cove, NY (US); Puneet Sodhi, Columbus, OH (US)

(73) Assignee: Click Therapeutics, Inc., New York, NY (US)

( * ) Notice: Subject to any disclaimer, the term of this patent is extended or adjusted under 35 U.S.C. 154(b) by 0 days.

(21) Appl. No.: 18/208,067

(22) Filed: Jun. 9, 2023

(65) Prior Publication Data

US 2023/0410967 A1 Dec. 21, 2023

Related U.S. Application Data

(60) Provisional application No. 63/350,976, filed on Jun. 10, 2022.

(51) Int. Cl.

*G16H 20/00* (2018.01)
*G06F 9/445* (2018.01)
*G16H 10/20* (2018.01)

(52) U.S. Cl.

CPC ......... *G16H 20/00* (2018.01); *G06F 9/44505* (2013.01); *G16H 10/20* (2018.01)

(58) Field of Classification Search

CPC ..... G16H 20/00; G16H 10/20; G06F 9/44505

(Continued)

(56) References Cited

U.S. PATENT DOCUMENTS

2004/0015586 A1 1/2004 Hegli et al.
2004/0064480 A1 4/2004 Bartlett et al.

(Continued)

FOREIGN PATENT DOCUMENTS

WO WO-2021168078 A1 * 8/2021 ............. A61B 5/743
WO WO-2022232537 A1 * 11/2022

(Continued)

OTHER PUBLICATIONS

International Search Report and Written Opinion for PCT Appl. No. PCT/US2023/24985, mailed Sep. 5, 2023.

(Continued)

*Primary Examiner* — Jason B Dunham
*Assistant Examiner* — Kimberly A. Sass
(74) *Attorney, Agent, or Firm* — MORRISON & FOERSTER LLP

(57) ABSTRACT

Provided herein are systems and methods for selecting configuration files for applications. A computing system may maintain configuration files readable by an application. Each of the plurality of configuration files may identify a respective set of content items to prompt users to perform at least one of a plurality of activities via the application towards achieving a respective endpoint of a plurality of endpoints. The computing system may determine an endpoint of the plurality of endpoints to address a condition of a user. The user may be on a medication to address the condition, at least partially in concurrence with performance of the activity via the application. The computing system may select a configuration file identifying a set of content items for an activity of the plurality of activities to be performed by the user via the application towards achieving the endpoint.

38 Claims, 46 Drawing Sheets

(58) Field of Classification Search
USPC ............................................................ 705/2
See application file for complete search history.

(56) References Cited

U.S. PATENT DOCUMENTS

| | | | | |
|---|---|---|---|---|
| 2005/0060565 | A1 | 3/2005 | Chebolu et al. | |
| 2008/0297829 | A1 | 12/2008 | Paek | |
| 2010/0250461 | A1 | 9/2010 | Arnold et al. | |
| 2016/0022193 | A1* | 1/2016 | Rau | A61B 5/4884 600/595 |
| 2018/0114596 | A1* | 4/2018 | Churchwell | G16H 20/70 |
| 2018/0374560 | A1* | 12/2018 | Paty | G16Z 99/00 |
| 2019/0019581 | A1 | 1/2019 | Vaughan et al. | |
| 2019/0074080 | A1 | 3/2019 | Appelbaum et al. | |
| 2019/0273754 | A1* | 9/2019 | Ting | G06N 3/088 |
| 2020/0004583 | A1 | 1/2020 | Kelly et al. | |
| 2020/0131581 | A1 | 4/2020 | Jain et al. | |
| 2020/0143931 | A1 | 5/2020 | Ghaemi et al. | |
| 2020/0335191 | A1 | 10/2020 | Brown et al. | |
| 2020/0372990 | A1 | 11/2020 | Ho | |
| 2021/0026626 | A1 | 1/2021 | Jain et al. | |
| 2021/0219892 | A1 | 7/2021 | Gossens et al. | |
| 2022/0300787 | A1 | 9/2022 | Wall et al. | |
| 2025/0253030 | A1 | 8/2025 | Ung et al. | |

FOREIGN PATENT DOCUMENTS

| | | | | |
|---|---|---|---|---|
| WO | WO-2023118907 A1 * | 6/2023 | G06F 21/554 |
| WO | 2024/167826 A1 | 8/2024 | |

OTHER PUBLICATIONS

International Preliminary Report on Patentability issued Dec. 10, 2024, for PCT application No. PCT/US2023/024985 filed Jun. 9, 2023, 7 pages.

Davidson, M. et al. (2022, e-pub. Feb. 25, 2022). "Efficacy and Safety of Roluperidone for the Treatment of Negative Symptoms of Schizophrenia," Schizophrenia Bulletin 48(3):609-619.

Ghaemi, S.N. et al. (2022). "A Smartphone-Based Intervention as a Adjunct to Standard-of-Care Treatment for Schizophrenia: Randomized Controlled Trial," JMIR Formative Research 6(3):e29154, 16 pages.

International Preliminary Report on Patentability issued Aug. 12, 2025, for PCT application No. PCT/US2024/014423 filed Feb. 5, 2024, 8 pages.

International Search Report and Written Opinion mailed May 24, 2024, for PCT application No. PCT/US2024/014423 filed Feb. 5, 2024, 9 pages.

Walling, D. et al. (2015, e-pub. Jun. 12, 2015). "Phase 2 Trial of an Alpha-7 Nicotinic Receptor Agonist (TC-5619) in Negative and Cognitive Symptoms of Schizophrenia," Schizophrenia Bulleting 42(2):335-343.

* cited by examiner

Step 1

Step 3

Step 4

Step 1

Step 2

Step 2

Step 3

Step 4

DYNAMIC SELECTION OF CONFIGURATION FILES FOR APPLICATIONS IN ACCORDANCE WITH ADAPTIVE GOAL SETTING

CROSS REFERENCES TO RELATED APPLICATIONS

The present application claims the benefit of priority under 35 U.S.C. § 119(e) to U.S. Patent Provisional Application No. 63/350,976, titled "Selection of Configuration Files for Applications in Accordance with Adaptive Goal Setting," filed Jun. 10, 2022, which is incorporated herein entirely by reference.

BACKGROUND

An application may be deployed and installed on a computing device to provide a digital therapeutic to address a behavioral or psychological condition of a user. As part of the digital therapeutic, the application itself may be configured to present a user interface containing various elements for display and carry out a multitude of operations in response to user interactions with elements of the user interface. After deployment, it may be difficult for the application to dynamically adapt to the responses from the user, leading to a lower likelihood that the user is to interact with the application. As a result, the efficacy of the digital therapeutic and user adherence to the digital therapeutic may be greatly diminished.

In a network environment, an application on a client may present one or more content items received as part of a message from a server. The content items may be customized for the particular user of the client, and may be selected based on any number of factors, such as user history, device type, location, or time, among others. The content items may also contain a script (e.g., event listeners or handlers) to specify presentation functionality when loaded onto the application of the client. For example, the content items may be provided as a part of a digital therapeutics platform and may include a textual content related to a condition associated with the user (e.g., smoke cessation, dieting, exercising, and psychological illnesses). Upon receipt, the application on the client may display the content items as user interface elements in a graphical user interface (GUI) of the application. As the content items are displayed via the application, the user may interact with one or more of the user interface elements to trigger the functionality of the corresponding content items.

While the provision of content items in this manner may carry out the specified functionalities, the range of possible functionalities and the selection of additional, subsequent content items for the user may be highly limited. In the context of digital therapeutics, the selection and provision of content items may be inadequate at achieving an endpoint associated the condition with the user. For one, the digital therapeutics application itself may have relatively static and fixed functionality once deployed and installed on the client, without resorting to updating the application. For instance, the application once installed may provide limited number of different configurations for graphical user interfaces in which to present the content items. For another, the state and behavior of the user may change throughout time, and the information of the factors used to select content items in advance may be inadequate to adapt to the related ever-changing state of the user.

In addition, the content items themselves may lack logic at accounting for such changes, and thus may be too generic and irrelevant to the state of the user at the time of presentation, leading to poor quality of human-computer interaction (HCI) between the application and the user. These may result in the expenditure of computing resources from loading and rendering these content items on the application, and consumption of network bandwidth from back-and-forth communications between the client and the server. From an HCI perspective, the lack of adaptability of the content items may lead to lower user engagement and lower adherence to the digital therapeutics provided through the presentation of the content items.

SUMMARY

To address these and other challenges, presented herein are systems and methods for dynamically selecting configuration files for applications in accordance with an adaptive goal setting (AGS) framework. The configuration files can be selected and personalized for the user initially based on baseline measurements of the user and then subsequently followed by response data from the user. The provision of digital therapeutic via the configuration files on the application in this manner may increase user engagement and adherence and ultimately the efficacy of the digital therapeutic. The AGS framework can continuously and dynamically configure the application to be tailored toward the user and their endpoints, by capturing the user's interest (meeting users where they are) and providing personalized content, and leveling goals based on baseline proficiency and metrics (matching goals with where the user is in their current functioning). The framework may provide for daily activity engagement (e.g., multiple times a day) to the user to take advantage of the application on their personal mobile devices to increase engagement and likelihood of therapeutic efficacy (compared to the traditional model, which only allows for interaction between a physician and a user when the user can visit a clinic in-person, which might be once a week, if that). The AGS framework may also provide for mood mitigation strategies to address user's states and to increase retention. In addition, the AGS framework may include personalized features such as a daily mood check-in, pre- and post-activity rating self-assessment, personal values exploration, and a "do it now" option.

The server (or a computing device) may select configuration files to provide to the application for presentation of content. Each configuration file may include logic or a module for an automaton (e.g., a finite state machine (FSM)) for one or more endpoints specifying one or more activities to be performed via the application on the client within a set time period. For digital therapeutics applications, the configuration file may identify a set of states and a set of transitions. Each state may correspond to a level associated with the activities of the endpoint, and may specify activities of the level to be performed via the application. Each transition may correspond to a condition to satisfy to move from one state to the next. The condition may be, for example, success or failure at carrying out the specified activities within the set time period.

The selection, provision, and the internal logic of the configuration files themselves may be in accordance with a framework for adaptive goal setting (AGS). The AGS framework may support the performance of activities for an endpoint (also referred herein as a goal, target, or objective) to address a condition of the user in an adaptive manner. The framework may include an introduction of a skill, setting up of a plan to achieve the endpoint, keeping track of the progress of the user, and adaptively varying the activities to incorporate for the endpoint.

To that end, during the introduction phase, a user profile may be constructed using user responses to prompts (e.g., questionnaire) related to the condition and endpoint for the user. The user profile may then be used to determine one or more endpoints and select configuration files to effectuate the endpoints as part of a plan to address the condition of the user. This AGS framework may be used to modulate, for example: different categories of objectives (e.g., smoke cessation, dieting to lower weight, improving exercise routine, and addressing symptoms of psychological illnesses); different types of activities (e.g., walking, running, swimming, hiking, dancing, and stair climbing); different difficulty levels of activities (e.g. lead climbing, top rope climbing, bouldering); a duration of activities (e.g., 5 minutes, 10 minutes, and 1 hour), a frequency of the activities (e.g., 1 time a week, 1 time a day, and 3 times a day), and a time of day in which to perform the activity (e.g., morning, afternoon, and after meals), among others.

The configuration file may provide the automaton logic with a persistent state, so that the user progress can be maintained across usage sessions. The configuration file itself may be a plug-in for the application and may be modified (e.g., by a clinician) for a particular endpoint, without relying on reconfiguration of the application. The automaton logic may be used to hold a set of variables, such as a level, an activity, an endpoint, and frequency, among others. For example, one set of variables may correspond to a level four of Activity A for 5 minutes every other day in the morning for a user. Given this information, the configuration file may be constructed to provide a set of content items to guide the user to perform and record the activity via the application on the client. As the user progresses through the automaton logic, the level, activity, endpoint, and frequency may be updated to provide a customized experience at each state. The logic may modulate the content items up or down to meet the current state of the user based on the responses via the application. In addition, over the course of the time period, different endpoints may be adaptively determined using response data and various configuration files may be dynamically selected in accordance with the endpoint to provide to the application.

By providing the configuration files in this manner, the application may be customized upon request and may provide a greater range of user experiences to the user to meet different endpoints, thereby improving the HCI between the user and the application. As the content items can be selected based on the states associated with the user in accordance with the configuration file, the content items may lead to higher user engagement with the digital therapeutic application. With higher likelihood of engagement, the digital therapeutic provided by the application may have higher efficacy in addressing the condition and increased adherence of the user with the digital therapeutic. The configuration files may also reduce resorting to having to update the application itself to provide additional functionality. Dynamically selecting and providing the configuration files may decrease the consumption of computing resources (e.g., processor, memory, and network bandwidth) from providing and loading irrelevant content items on the application. Furthermore, the configuration files may reduce the expenditure of network bandwidth from back-and-forth communications associated with requesting and retrieving the content items.

Aspects of the present disclosure are directed to systems, methods, and non-transitory computer-readable media for selecting configuration files for applications. A computing system may maintain a plurality of configuration files readable by an application. Each of the plurality of configuration files may identify a respective set of content items to prompt users to perform at least one of a plurality of activities via the application towards achieving a respective endpoint of a plurality of endpoints. The computing system may determine an endpoint of the plurality of endpoints to address a condition of a user. The computing system may select, from the plurality of configuration files, a configuration file identifying a set of content items for an activity of the plurality of activities to be performed by the user via the application towards achieving the endpoint. The computing system may provide the configuration file to the application to present the set of content items to prompt the user to perform the activity via the application.

In some embodiments, the computing system may receive, from the application, response data identifying one or more interactions by the user with the set of content items presented via the application towards achieving the endpoint. The computing system may determine a second endpoint of the plurality of endpoints based on the response data for the endpoint. The computing system may select, from the plurality of configuration files, a second configuration file based on the second endpoint to provide to the application.

In some embodiments, the computing system may identify, from a profile of the user, a first level of a plurality of levels towards achieving the endpoint. The computing system may determine a transition from the first level to a second level, based on response data identifying one or more interactions by the user with the set of content items presented via the application. The computing system may select, from the plurality of configuration files, a second configuration file based on the transition to the second level. In some embodiments, the computing system may determine, based on a performance of the activity of the user towards achieving the endpoint, whether to transition to the first level or a second level of the plurality of levels towards achieving a second endpoint.

In some embodiments, each of the plurality of configuration files may identify a respective criterion defining a first measure of the user to select a corresponding configuration file identifying the set of content items to prompt users to perform the activity. The computing system may determine a second measure based on a profile of the user. The second measure may identify at least one of: (i) a likelihood that the user is to perform the activity or (ii) a predicted efficacy of the activity on the user towards achieving the endpoint. In some embodiments, the computing system may identify, from the plurality of activities, the activity based on a comparison of the first measure with the second measure.

In some embodiments, the computing system may receive, from the application, a response identifying a mood of the user in response to presentation of a prompt via the application at a defined time. In some embodiments, the computing system may identify, from the plurality of activities, the activity based on the mood of the user indicated in the response. In some embodiments, the computing system may receive, from the application, a response identifying a plurality of personal values of the user. In some embodiments, the computing system may identify, from the plurality of activities, the activity based on the plurality of personal values associated with the user identified in the response. In some embodiments, the computing system may determine a progression metric based on performance of the activity towards achieving the endpoint. In some embodiments, the computing system may present, via the application, a connection between the progression metric and the personal value associated with the user.

In some embodiments, the computing system may present, via the application, a prompt for the user to indicate a first rating associated with the activity prior to performance of the activity via the application. In some embodiments, the computing system may store a response identifying the first rating associated with the activity from the application. In some embodiments, the computing system may present, via the application, a prompt for the user to indicate a second rating associated with the activity subsequent to performance of the activity via the application. In some embodiments, the computing system may present, via the application, a comparison of the second rating with the first rating. In some embodiments, the computing system may determine, from the plurality of endpoints, the endpoint based on at least one of (i) a baseline assessment and (ii) an indication by the user requesting an activity towards achieving the endpoint.

In some embodiments, at least one configuration file of the plurality of configuration files may define a finite state machine. The finite state machine may identify a plurality of states including at least a first state and a second state, each of which corresponds to an intensity level for a corresponding activity and specifies an output. The output may identify the one or more content items to present via a user interface of the application. The finite state machine may identify a plurality of transitions, each of which specifies an event to be detected via the user interface of the application to move from the first state to the second state, the event corresponding to an interaction to be performed via the application for the respective activity.

In some embodiments, the plurality of endpoints may be associated with at least one of a plurality of classifications for endpoints. In some embodiments, a first subset of the plurality of endpoints may be associated with a first classification and a second subset of the plurality of endpoints may be associated with a second classification. In some embodiments, the user may be on a medication to address the condition, at least partially in concurrence with performance of the activity via the application. In some embodiments, the condition may include a psychological or mental illness.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

DETAILED DESCRIPTION

For purposes of reading the description of the various embodiments below, the following enumeration of the sections of the specification and their respective contents may be helpful:

Section A describes embodiments of systems and methods of selecting configuration files for applications; and Section B describes a network and computing environment which may be useful for practicing embodiments described herein.

A. System and Method for Selecting Configuration Files for Applications

Figure 1:
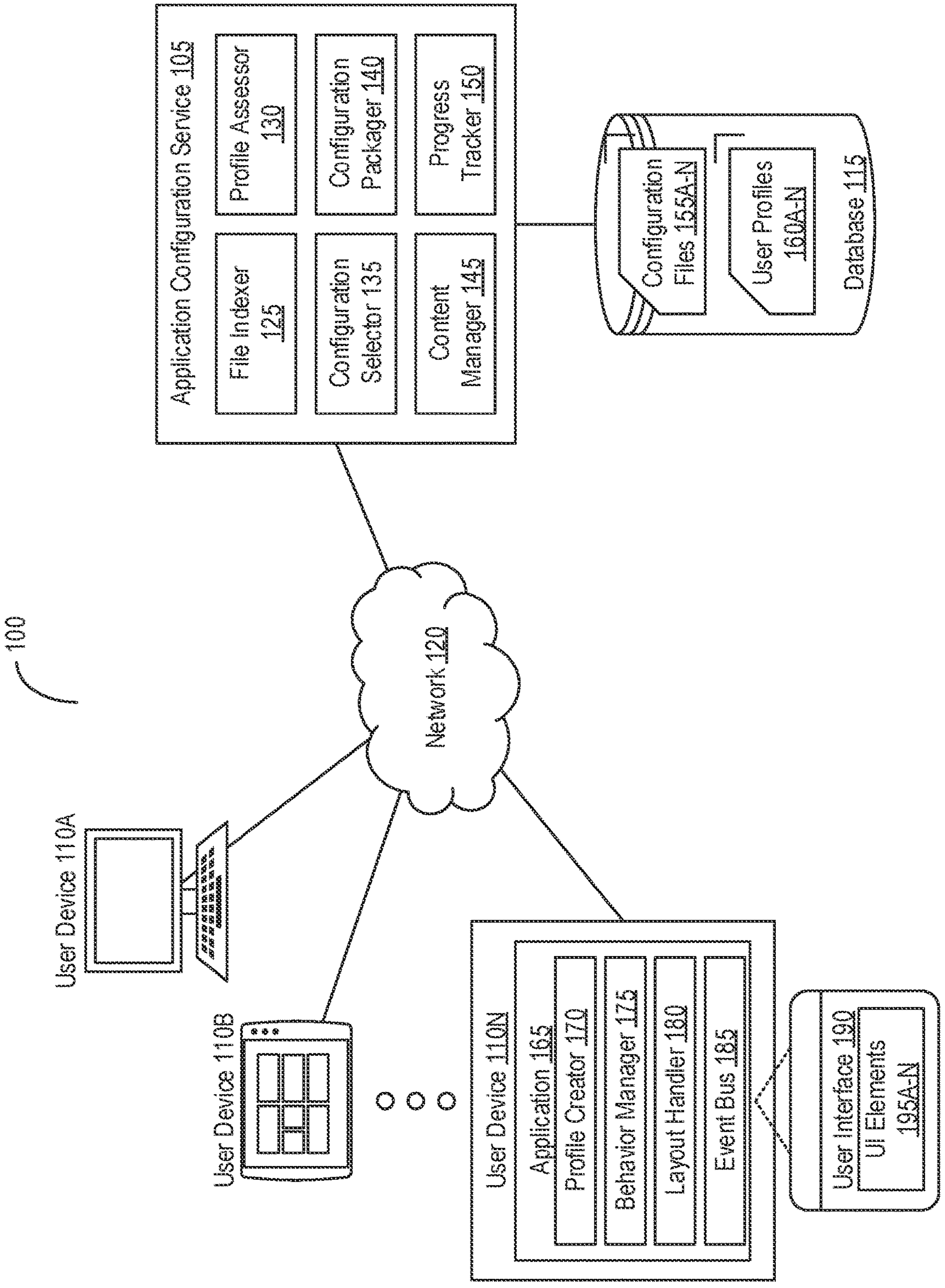
FIG. 1 depicts a block diagram of a system for selecting configuration files for applications, in accordance with an illustrative embodiment.

Referring now to FIG. 1, depicted is a block diagram of a system 100 for selecting configuration files for applications. In overview, the system 100 may include at least one application configuration service 105, one or more user devices 110A-N (hereinafter generally referred to as user device 110), and at least one database 115, communicatively coupled with one another via at least one network 120. The application configuration service 105 may include at least one file indexer 125, at least one profile assessor 130, at least one configuration selector 135, at least one configuration packager 140, at least one content manager 145, and at least one progress tracker 150, among others. The database 115 may store, maintain, or otherwise include a set of configuration files 155A-N (hereinafter generally referred to as configuration files 155) and a set of user profiles 160A-N (hereinafter generally referred to as user profiles 160), among others. At least one of the user devices 110 may include at least one application 165. The application 165 may include at least one profile creator 170, at least one behavior manager 175, at least one layout handler 180, and at least one event bus 185, among others. The application 165 may also provide at least one user interface 190 including one or more user interface elements 195A-N (hereinafter generally referred to as UI elements 195).

Each of the components in the system 100 (e.g., the application configuration service 105 and its components and each user device 110 and its components) may be executed, processed, or implemented using hardware or a combination of hardware, such as the system 1700 detailed herein in Section B. In some embodiments, the application configuration service 105 may be part of the user device 110 (e.g., as part of the application 165). In some embodiments, at least a portion of the functionalities of the application configuration service 105 (including the file indexer 125, the profile assessor 130, the configuration selector 135, the configuration packager 140, the content manager 145, and the progress tracker 150) may be performed on the user device 110. For example, the operations of the profile assessor 130, the configuration selector 135, and the configuration packager 140 may be performed on the user device 110.

In further detail, the application configuration service 105 may (sometimes herein generally referred to as a service) be any computing device comprising one or more processors coupled with memory and software and capable of performing the various processes and tasks described herein. The application configuration service 105 may be in communication with the one or more user devices 110 and the database 115 via the network 120. The application configuration service 105 may be situated, located, or otherwise associated with at least one server group. The server group may correspond to a data center, a branch office, or a site at which one or more servers corresponding to the application configuration service 105 is situated.

Within the application configuration service 105, the file indexer 125 may generate and store configuration files 155 to be provided to the applications 165. The profile assessor 130 may create user profiles 160 for users of applications 165 on user devices 110. The endpoint selector 135 may determine an endpoint for the user and select configuration files 155 to provide. The configuration packager 140 may provide the configuration files 155 to be loaded on the application 165. The content manager 145 may identify and provide content to be presented via the UI elements 195 of the user interface 190 for the application 165. The progress tracker 150 may update the user profiles 160 and manage re-determination of endpoints for the user. The functionalities of the various components of the application configuration service 105 may be carried out by the application 165 on the user device 110.

The user device 110 (sometimes herein referred to as a client, a client device, or an end user computing device) may be any computing device comprising one or more processors coupled with memory and software and capable of performing the various processes and tasks described herein. The user device 110 may be in communication with the application configuration service 105 and the database 115 via the network 120. The user device 110 may be a smartphone, other mobile phone, tablet computer, wearable computing device (e.g., smart watch, eyeglasses), or laptop computer. The user device 110 may be used to access the application 165. In some embodiments, the application 165 may be downloaded and installed on the user device 110 (e.g., via a digital distribution platform). In some embodiments, the application 165 may be a web application with resources accessible via the network 120.

The application 165 executing on the user device 110 may be a digital therapeutics application and may provide one or more sessions (sometimes referred to herein as a therapy session) to address at least one condition of the user. The condition of the user may include, for example, a habit (e.g., smoking, dieting, or exercising), a chronic pain (e.g., associated with or include arthritis, migraine, fibromyalgia, back pain, Lyme disease, endometriosis, repetitive stress injuries, irritable bowel syndrome, inflammatory bowel disease, and cancer pain), a skin pathology (e.g., atopic dermatitis, psoriasis, dermatillomania, and eczema), an affective disorder (e.g., depression, bipolar disorder, or dysthymia), a cognitive impairment (e.g., mild cognitive impairment (MCI), Alzheimer's, multiple sclerosis, and schizophrenia), and other ailments (e.g., narcolepsy and oncology), among others. The affective disorder and cognitive impairment may fall under a psychological (or mental) illness or disorder.

The user may be at least partially concurrently taking a medication to address the condition, while being provided sessions through application 165. The application 165 may enhance, augment, or otherwise increase the efficacy of the medication in addressing the condition of the user. For instance, if the medication is for pain, the user may be taking: acetaminophen; a nonsteroidal anti-inflammatory composition; an antidepressant; an anticonvulsant; or other composition; among others. For skin pathologies, the user may be taking: a steroid, antihistamine, or topic antiseptic, among others. For cognitive impairments, the user may be taking cholinesterase inhibitors, memantine, or an antipsychotic, such as risperidone, quetiapine, olanzapine, ziprasidone, paliperidone, or aripiprazole, among others. For certain neurological disorders, the user may be on a stimulant or antidepressant, among others. For affective disorders, the user may be on an antidepressant or mood stabilizers, among others. The user of the application 165 may also be undergoing other psychotherapies for these conditions.

The application 165 can include, present, or otherwise provide the user interface 190 including the one or more UI elements 195 to a user of the user device 110 in accordance with the configuration file 155 loaded on the application 165. The UI elements 195 may correspond to visual components of the user interface 190, such as a command button, a text box, a check box, a radio button, a menu item, and a slider, among others. The application 165 may be a digital therapeutics application and may provide a session (sometimes referred to herein as a therapy session) via the user interface 190 towards achieving one or more endpoints of the user (sometimes herein referred to as a patient, person, or subject).

Figure 2A:
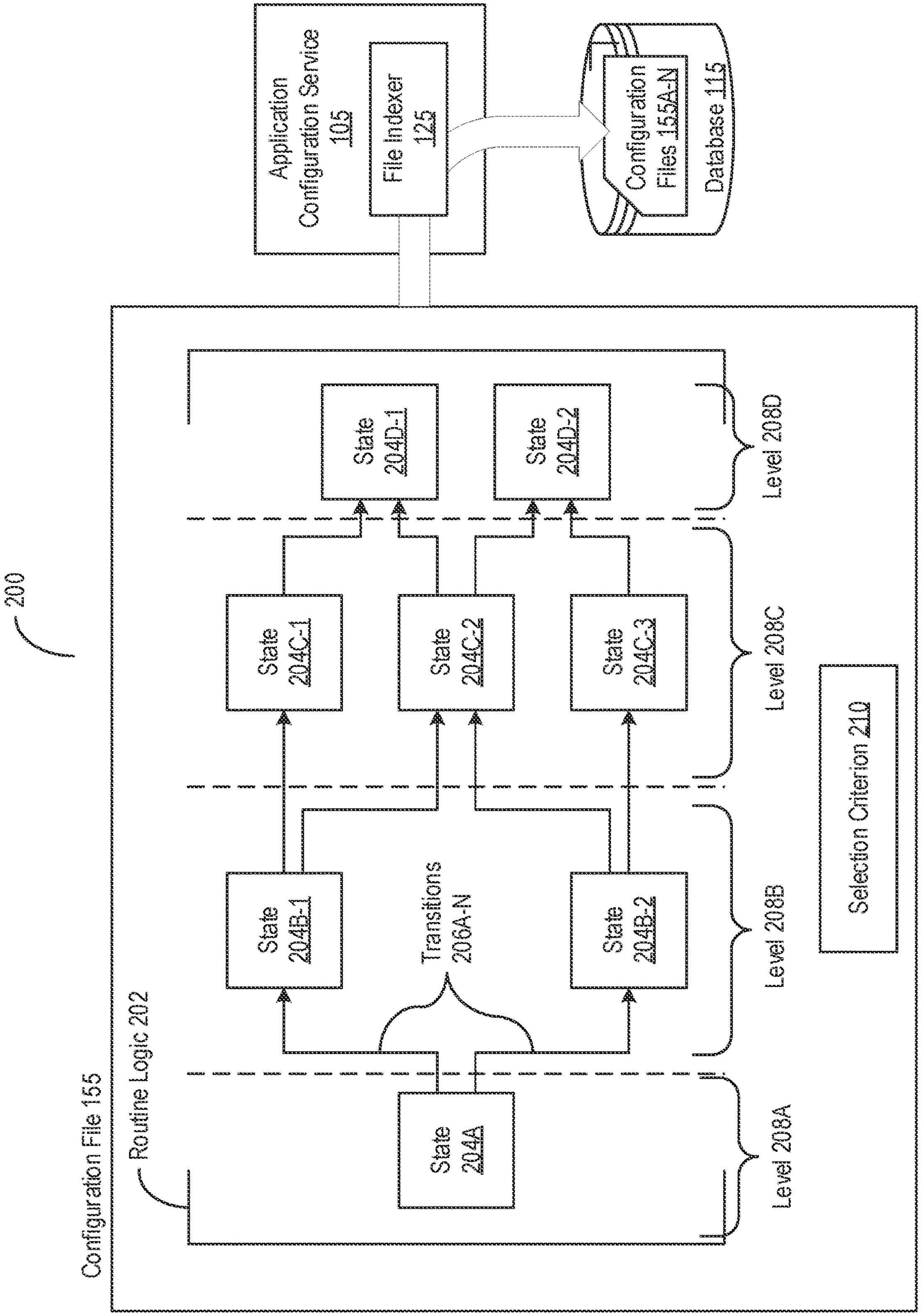
FIG. 2A depicts a block diagram of a process for maintaining configuration files in the system for selecting configuration files, in accordance with an illustrative embodiment.

Referring now to FIG. 2A, depicted is a block diagram of a process 200 for maintaining configuration files in the system 100 for selecting configuration files. The process 200 may include or correspond to operations in the system 100 to store and catalogue configuration files for applications. Under the process 200, the file indexer 125 executing on the application configuration service 105 may retrieve, identify, or otherwise receive at least one configuration file 155. The configuration file 155 may be from another source, such as a computing device of a developer creating the configuration file 155. For example, a clinician may compose a script to form a suite of configuration files 155 for providing a digital therapeutics. The configuration file 155 may include instructions for configuring, defining, or otherwise specifying various functionalities of a package (or plug-in) to be provided to the application 165. The functionalities specified by the configuration file 155 may be separate from the built-in logic and functionalities of the application 165, such as those of the application configuration service 105. In some embodiments, the instructions included in the configuration file 155 may be in a human-readable format, such as Yet Another Markup Language (YAML), Extensible Markup Language (XML), and JavaScript Object Notation (JSON), among others. In this manner, the effort undertaken by a developer in writing the human readable instructions in the configuration file 155 may be less than that of composing instructions in other formats.

The configuration file 155 may specify, define, or otherwise identify at least one routine logic 202. In some embodiments, the routine logic 202 itself may be defined in accordance with an automaton, such as a finite state machine (FSM), a decision tree, or a pushdown automaton, among others. The routine logic 202 may identify a set of content items to prompt users to perform a set of activities towards achieving one or more endpoints (sometimes referred herein as goals, targets, or objectives) in addressing a condition of a user of the application 165. For example, the condition may include smoking, obesity, psychological disorders (e.g., Schizophrenia), mental cognition, and depression, among others, on the part of the user. The activities defined by the routine logic 202 may include those for treatment or management of the conditions. The set of activities may form steps along a progression of a user to achieve the target endpoint for a given condition, such as cessation of smoking.

The routine logic 202 of the configuration file 155 may identify or include a set of states 204A-N (hereinafter generally referred to as states 204), a set of transitions 206A-N (hereinafter generally referred to as transitions 206), and a set of levels 208A-N (hereinafter generally referred to as levels 208), among others. The set of states 204, the set of transitions 206, and the set of levels 208 in conjunction may be used to define or specify the set of activities to be performed by the user of the application 165 towards achieving one or more endpoints. Each state 204 may define, identify, or otherwise specify at least one output to be produced by the routine logic 202 upon invocation. The output may be for a particular activity for the set of activities, and may include one or more operations to be performed by the application 165. In some embodiments, the output may identify user interface elements 195 to be presented via the user interface 190 of the application 165. For example, the output may include or specify a set of content items to be generated or retrieved (e.g., using one or more identifiers (e.g., uniform resource locator (URL)) for presentation as user interface elements 195 in the user interface 190. In some embodiments, the output may identify another configuration file 155 to be loaded. For instance, the output may include an identifier (e.g., a file name) for the next configuration file 155 to be loaded on the application 165. At least one state 204 may correspond to the state 204 at which the routine logic 202 is to start from (e.g., the state 204A as depicted).

Between a pair of states 204, the routine logic 202 may define, specify, or otherwise include at least one transition 206. Each transition 206 may define, identify, or otherwise specify an event to be detected via the application 165 to transition or update the routine logic 202 from one state 204 to another state 204. The event may correspond to a user interaction received via the application 165 on the user device 110. For instance, the transition 206 may specify to move from one state 204A to the next state 204B, the user is to record completion of Exercise A via the user interface 1685 of the application 165. In some embodiments, the routine logic 202 may include at least two transitions 206 from a given state 204. For example, the routine logic 202 may identify one transition 206 for successful completion of the activity associated with the state 204. Conversely, the routine logic 202 may identify another transition 206 for failure of completion of the activity associated with the state 204.

Among the set of states 204 and the set of transitions 206, the routine logic 202 may define, identify, or otherwise include the levels 208. In some embodiments, the level 208 may be defined, identified, or otherwise specified in the states 204 or the transitions 206 themselves. Depending on the level 208, the set of activities specified by the corresponding set of states 204 may be defined in terms of a duration, a frequency, and a time of day for the activity. In some embodiments, the levels 208 may correspond to the same endpoint or a different endpoint. For example, the first level 208A may correspond to a lower level for a given endpoint and the second level 208B may correspond to a higher level for the same endpoint or another endpoint. In general, with the successful completion of the activity from the previous state 204, the higher the level 208, the activity associated with a given state 204 may have a higher difficulty or intensity in terms of duration or frequency, or both. For example, for a set of activities, one state 204A at a lower level 208A may specify Activity B once a week in the evening, while another state 204B-1 at a higher level 208B may specify Activity C five times a week every morning. Conversely, with the failure in completion of the activity from the previous state 204, the higher the level 208, the activity associated with the given state 204 may lower difficulty or intensity in terms of duration or frequency, or both. The activity associated with the given state 204 may differ from the activity associated with the previous state 204. For example, the activity may be part of a mitigation measure for when the previous activity is not successfully completed.

Figure 6A:
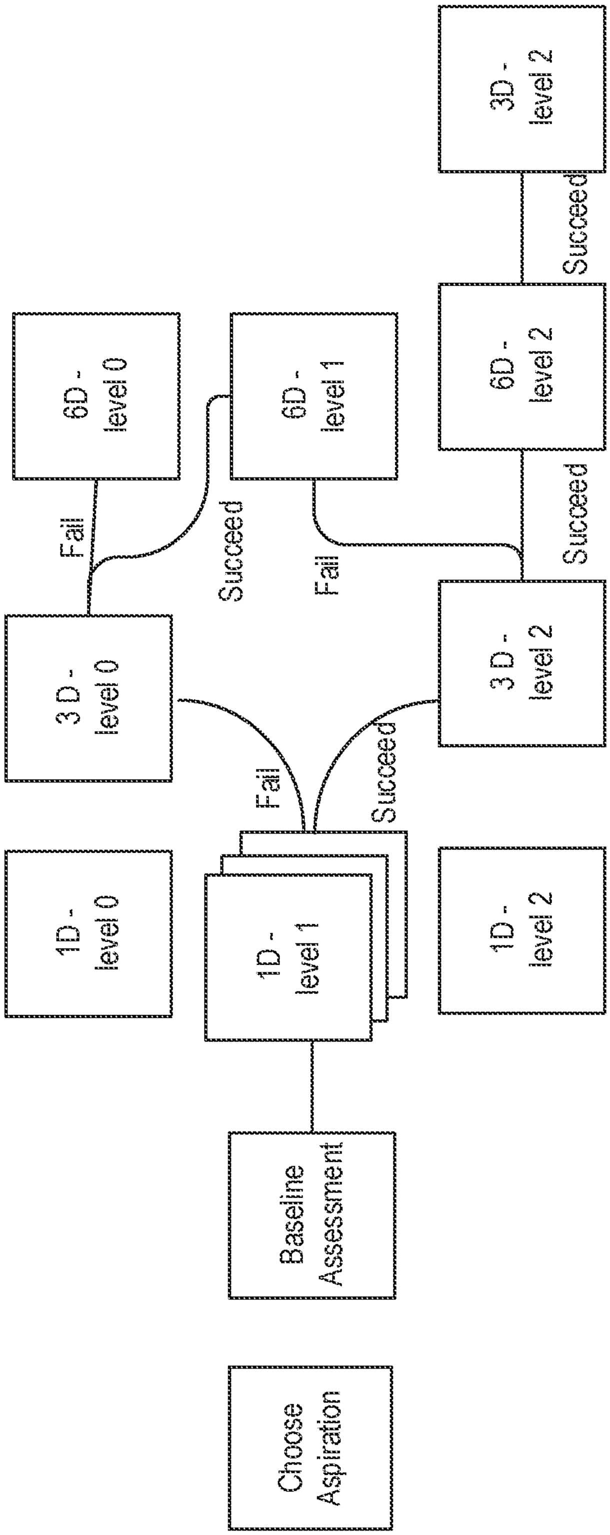
FIGS. 6A-C each depict a block diagram of configuration files to perform routines, in accordance with an illustrative embodiment.
Figure 6B:
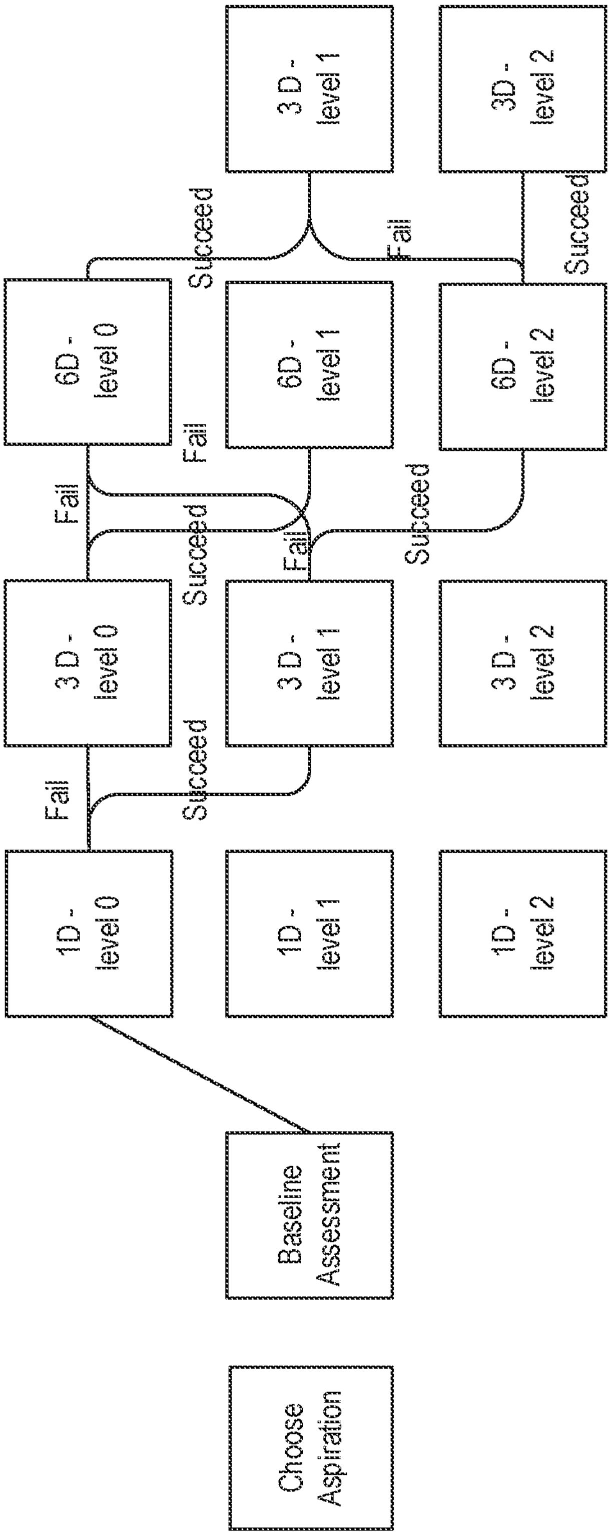
Figure 6C:
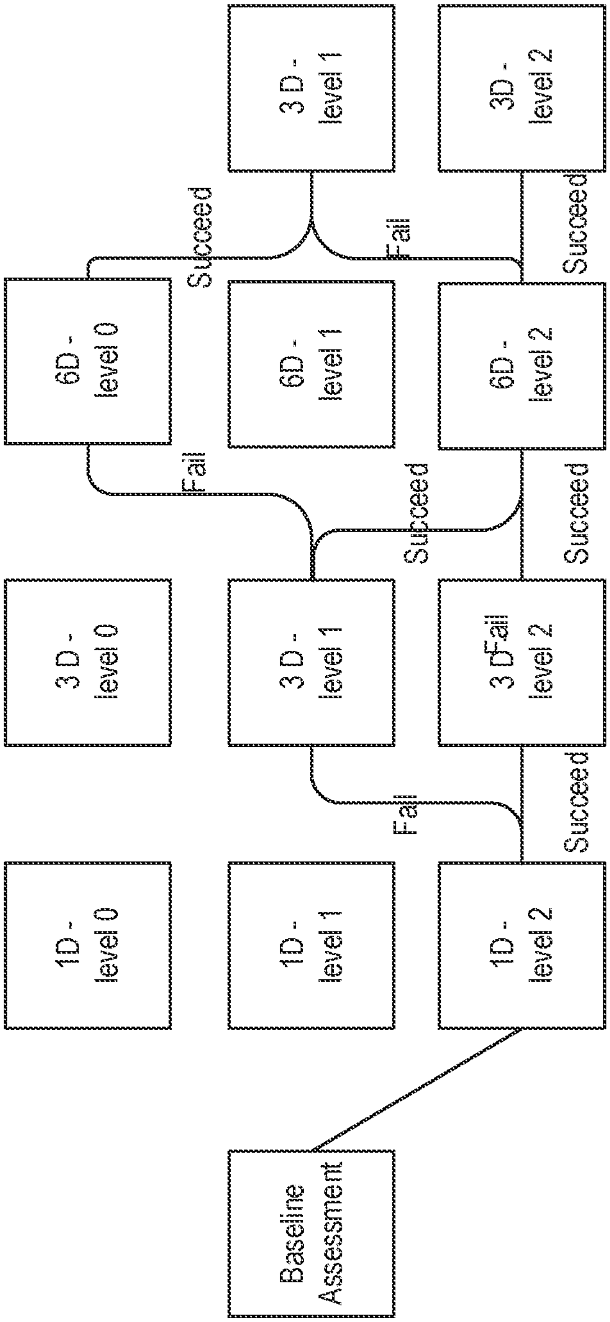

With the definition of the states 204, the transitions 206, and the levels 208, the routine logic 202 of the configuration file 155 may titrate the type, frequency, and duration of activity to specify the user to perform via the application 165. Furthermore, the routine logic 202 may adaptively produce outputs in response to the actions of the user of the application 165. Examples of the routine logic 202, including the states 204, the transitions 206, and the levels 208, are detailed herein in conjunction with FIGS. 6A-C. The routine logic 202 across the set of configuration files 155 may be used to effectuate an adaptive goal setting (AGS) framework. For example, as depicted in FIGS. 6A-C, the user may take a baseline assessment and select an aspiration. The user may then be presented with a 1-day (1D) goal (or endpoint) to orient the user. The user may then proceed to a 3-day (3D) goal at the same level or lower level depending on success. The user may progress through the 3-day goals until reaching the lowest or highest level. The user may be able to choose a new aspiration to work on (if there is sufficient time remaining).

Each configuration file 155 may correspond to one or more goals, and may be selected based on a baseline assessment of the user's function to inform the level of the goal and associated activities. An assessment of the user's interests or aspirations in the domain may be used to identify the content of the goal and associated activities for the goal and configuration files 155. Following the introduction, the users can receive up to any number of goals as part of the configuration file 155. For example, if there are four phases, a user might receive 4 goals, then 4 more goals, then 4 more goals, then 8 goals. Each goal may be associated, for example, with four daily activities. Users that complete all activities associated with the goal may transition onto the next level goal within the same interest or aspiration. When the user completes a goal, the application 165 may provide a positive affirmation as well as opportunities to savor positive emotions associated with completing their goal. If the minimum or maximum goal level within an interest or aspiration has been reached, the new goal may be within a new interest or aspiration presented via the application 165 at the level determined from the initial baseline assessment. If a certain number of goals within the same interest or aspiration has been reached, the user may be asked to reselect an interest or aspiration.

When provided to the application 165, the configuration file 155 may provide one or more endpoint or goal-related activities for a user of the application 165 to perform and complete. The configuration file 155 may provide the user the option (e.g., via user interface elements 195 on the user interface 190 of the application 165) to perform the specified activities when prompted or schedule at a later time. The activities may be configured to increase likelihood of reflection and practice of therapeutic skills learned through the activities. The configuration files 155 and the activities may be selected based on personal values related to classifications of endpoints.

Through selective provision of the configuration files 155, the application 165 may provide daily activities within an endpoint that are sequential. When the user completes an activity, the application 165 may provide a positive affirmation. If the user indicates during daily check-in that they did not complete the previous day's activity, the application 165 may prompt the user to perform the same daily activity to continue towards achieving the endpoint or goal. New activities may be locked if the user has been inactive or has not completed the preceding activity. For example, after a certain time period (e.g., 1-2 days) of inactivity or activity non-completion, the user may be prompted by the application 165 with the same daily activity to continue. After another period of time (e.g., above 3 days) of inactivity or activity non-completion, the user may be provided via the application 165 the option of repeating the previously presented activity or getting an activity from a new endpoint.

Continuing on, for certain phases, if a user chooses to get an activity from a new endpoint, the activity may be presented at a decremented level within the same aspiration via the application 165. If the user has reached the lowest possible level for an endpoint, the user may be presented with repeating the previously presented activity. For other configuration files 155, if the user selects an activity from a new endpoint, the user may be presented to reselect an aspiration or domain. After a daily activity is presented to the user, the application 165 may prompt the user to either start the activity immediately or set a time later in the day to complete the activity. If the user chooses to set a reminder, the application 165 may send a notification at the selected time. The user may have the option to start the scheduled activity ahead of or after the scheduled time via the home screen of the application 165.

In addition, the configuration file 155 may identify, define, or specify at least one selection criterion 210 for selection of the corresponding configuration file 155. In some embodiments, the selection criterion 210 may be separate from the configuration file 155 and be associated with the configuration file 155. For example, an association between the selection criterion 210 and the configuration file 155 may be stored on the database 115 using one or more data structures, such as a linked list, a tree, a table, an array, a graph, a heap, or hash tables, among others. The selection criterion 210 may specify one or more parameters identified with the user profile 160 for which the configuration file 155 is to be selected for provision to the application 165 on the user device 110. When the parameters specified in the selection criterion 210 match the parameters identified in the user profile 160, the configuration file 155 may be selected for provision to the application 165. In some embodiments, the selection criterion 210 may define one or more baseline measures derived from the user profile 160 for which the configuration file 155 is to be selected. When the measures derived from the parameters of the user profile 160 satisfy (e.g., greater than or equal to) the baseline measures specified by the selection criterion 210, the configuration file 155 may be selected for provision to the application 165. Additional details in relation to the parameters or baseline measures for the selection criterion 210 will be detailed herein below.

Upon receipt, the file indexer 125 may store and maintain the configuration file 155 on the database 115. The database 115 may be part of the application configuration service 105 or otherwise be accessible by the application configuration service 105. In some embodiments, the file indexer 125 may store an association between the configuration file 155 and the source from which the configuration file 155 is received. In some embodiments, the file indexer 125 may store an association between the configuration file 155 and a version identifier for the configuration file 155. The configuration file 155 may be maintained on the database 115 for provision to instances of the applications 165 across various clients 110. As the configuration file 155 is separate from the application 165, the configuration files 155 may be readily updated and interchanged.

Figure 2B:
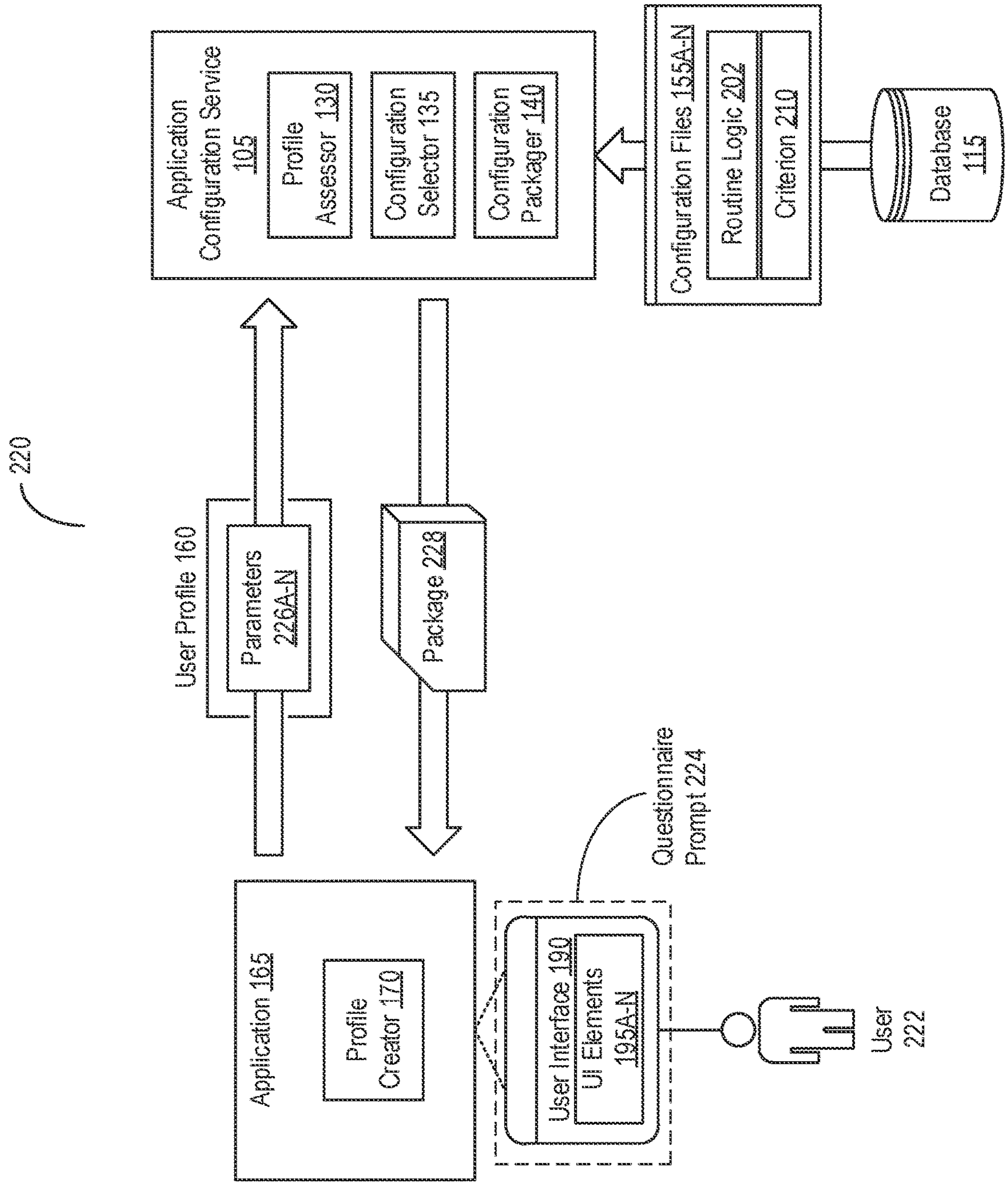
FIG. 2B depicts a block diagram of a process for assessing user profiles to provide configuration files in the system for selecting configuration files, in accordance with an illustrative embodiment.

Referring now to FIG. 2B, depicted is a block diagram of a process 220 for assessing user profiles to provide configuration files in the system 100 for selecting configuration files. The process 220 may include or correspond to operations in the system 100 for evaluating parameters in user profiles to select configuration files 155 to generate packages for provision to the application 165. Under the process 220, the profile creator 170 of the application 165 executing on the user device 110 may produce, output, or otherwise generate the user profile 160 for a user 222 of the application 165. The user profile 160 may be generated based on one or more responses from the user 222. The responses may identify, define, or otherwise be associated with the endpoint and the condition as indicated by the user 222.

In generating the user profile 160, the profile creator 170 may display, render, or otherwise present at least one prompt 224 to receive the responses from the user 222. The prompt 224 may be presented to the user 222 using one or more of the user interface elements 195 on the user interface 190. In some embodiments, the prompt 224 may be presented upon installation of the application 165 on the user device 110. In some embodiments, the prompt 224 may be presented in response to an interaction on the user interface 190 on the application 165. The interaction may correspond to a request by the user 222 for another endpoint or a new set of activities to be performed via the application 165. In some embodiments, the prompt 224 may be in accordance with a defined time period, for example, once every 2-6 hours, once a day in the morning, or once every week, among others. The prompt 224 may identify or include a set of questions for the user 222. The questions themselves may correspond to text, audio, or visual content on the user interface elements 195 of the user interface 190. The responses to the questions may be entered or inputted by the user 222 via other user interface elements 195, such as radio buttons, command buttons, text boxes, sliders, or check boxes, among others.

The profile creator 170 may include one or more event listeners to detect, retrieve, or otherwise receive responses via the prompt 224 presented on the user interface 190. The set of questions presented in the prompt 224 may be composed, set, or otherwise configured by the administrator of the application configuration service 105 or the application 165. The questions may inquire the user 222 to indicate at least one desired endpoint to achieve (sometimes herein referred to as a goal, objective, or target) and at least one condition to be addressed (e.g., behavioral, psychological, or physical), among others. The questions may also inquire the user 222 to identify at least one state (e.g., mood, emotional, behavioral, or physiological state) of the user 222. The questions may also ask the user 222 preferences for performance of activities or routines, such as type of routine, frequency, duration, day of week, and time of day, among others. The responses to the questions may be recorded, inputted, or entered via the user interface elements 195 on the user interface 190.

Figure 7A:
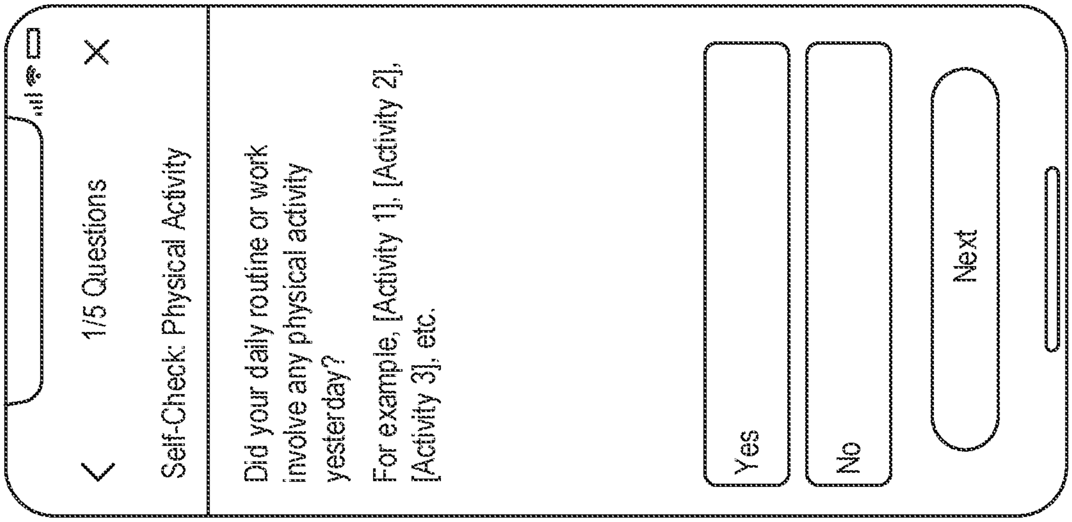
FIGS. 7A-F each depict examples of screenshots of a prompt to assess a physical activity of a user, in accordance with an illustrative embodiment.
Figure 7B:
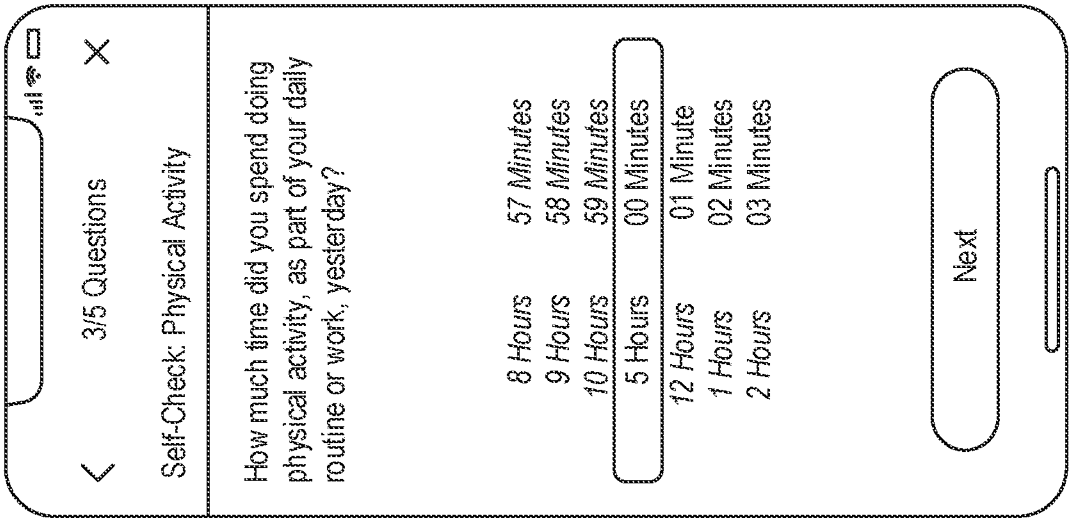
Figure 7C:
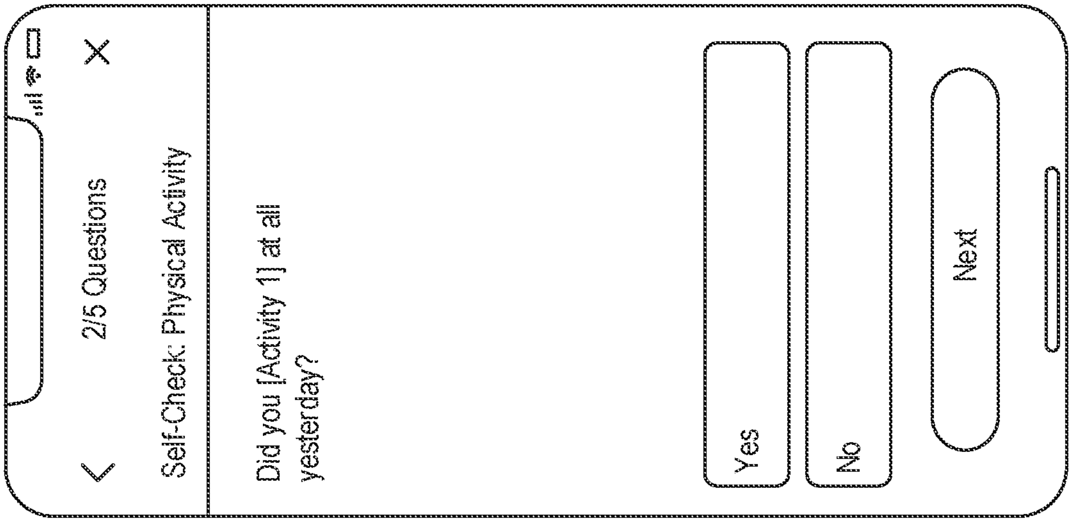
Figure 7D:
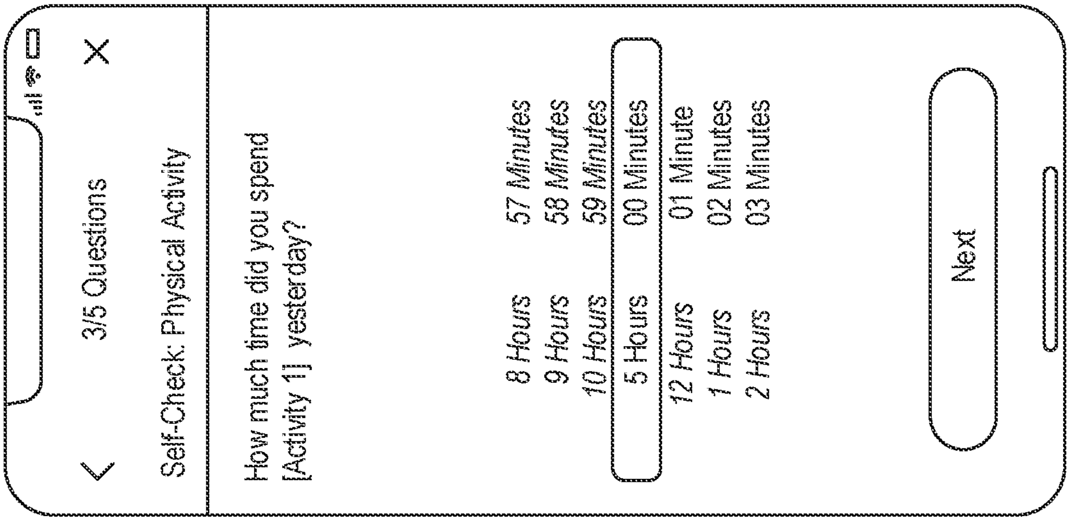
Figure 7E:
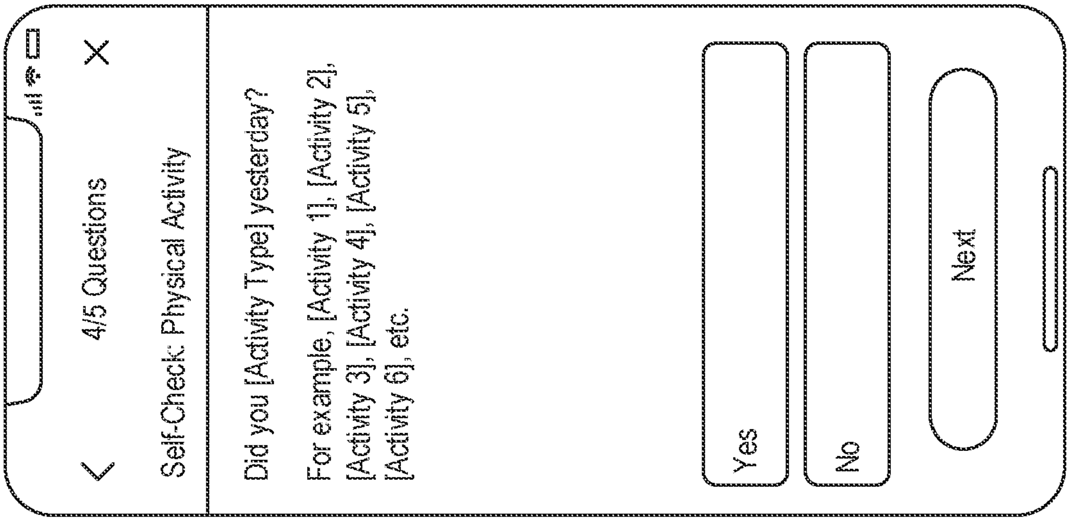
Figure 7F:
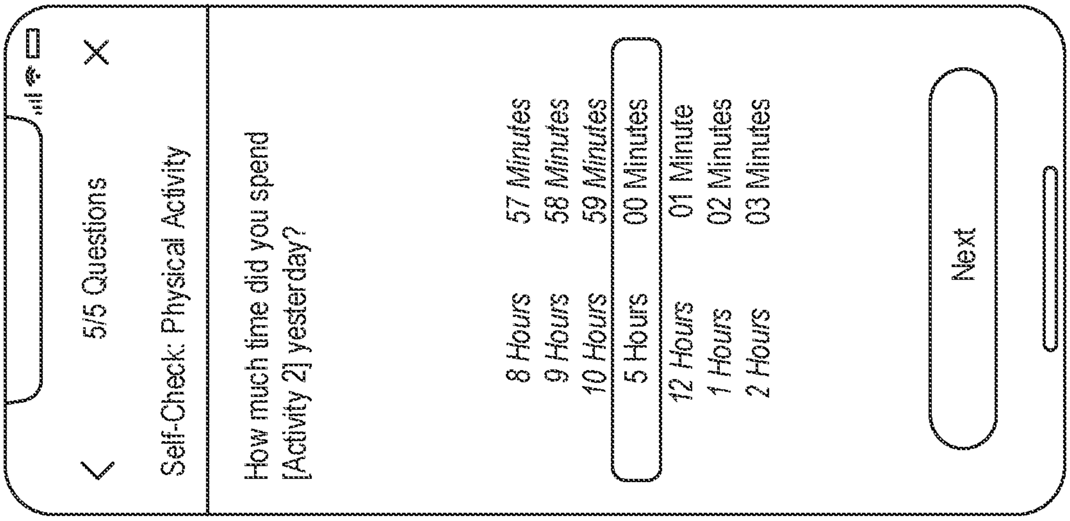
Figure 8A:
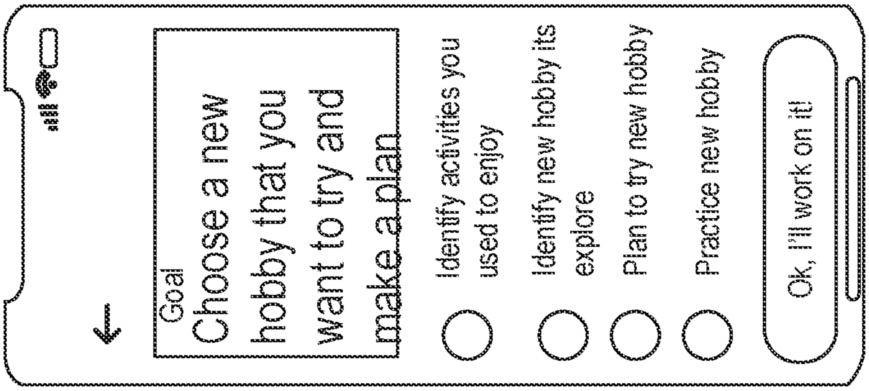
FIGS. 8A-L each depict examples of screenshots of prompts to build a user profile in relation to an endpoint to pursue a hobby at a first step of level 0, in accordance with an illustrative embodiment.
Figure 8B:
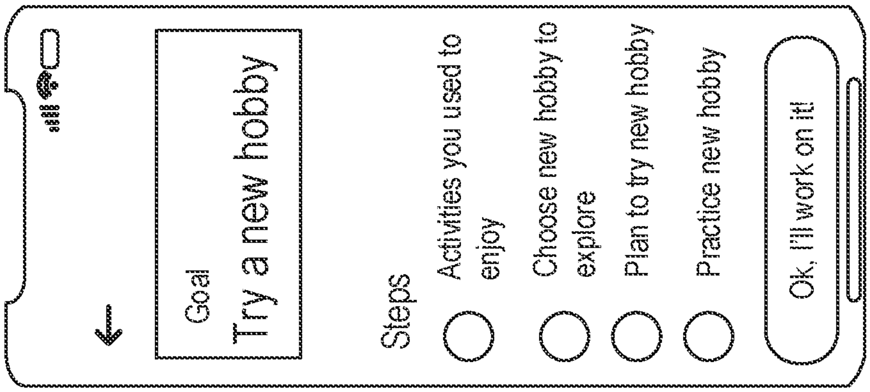
Figure 8C:
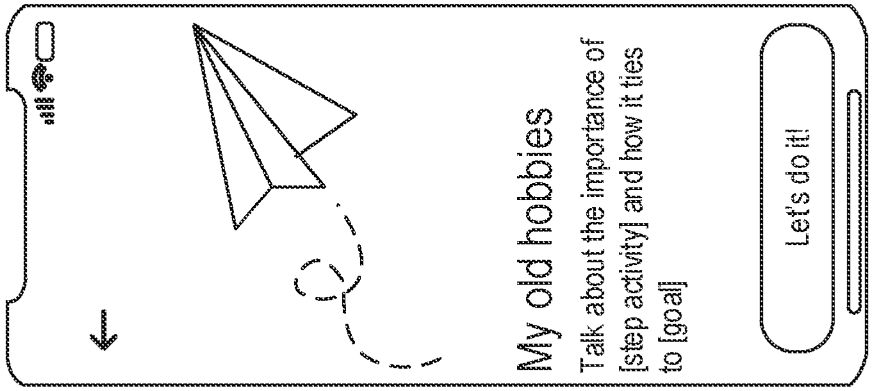
Figure 8D:
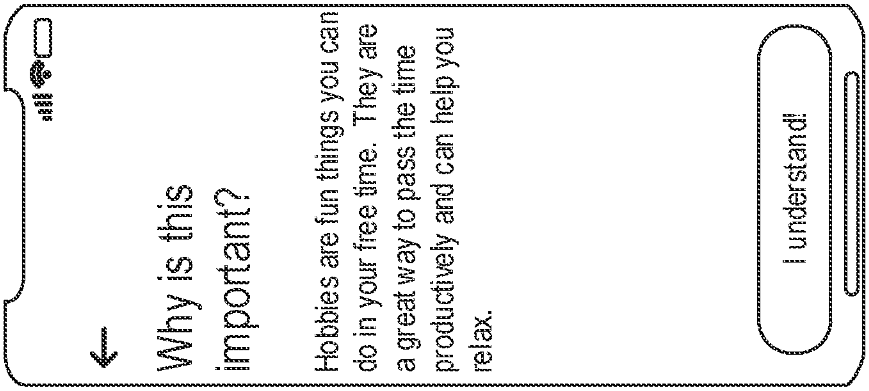
Figure 8E:
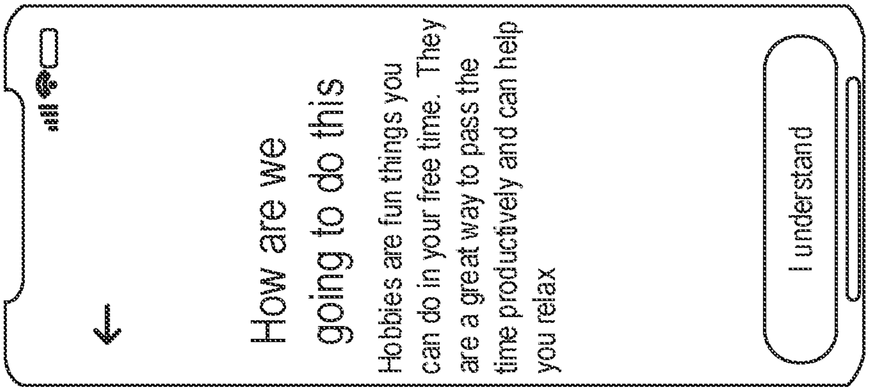
Figure 8F:
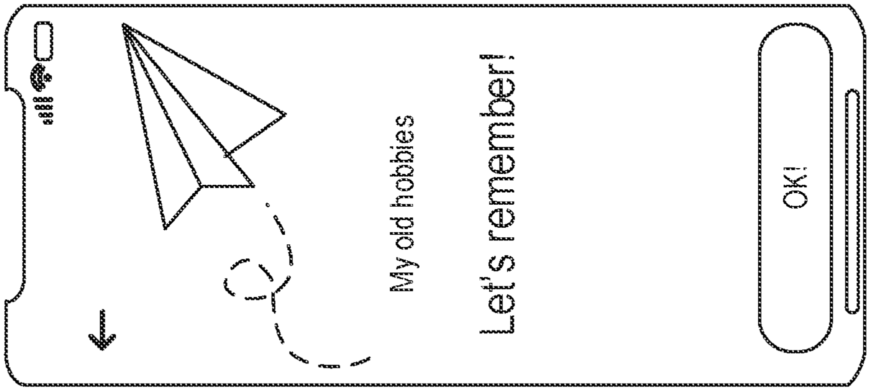
Figure 8G:
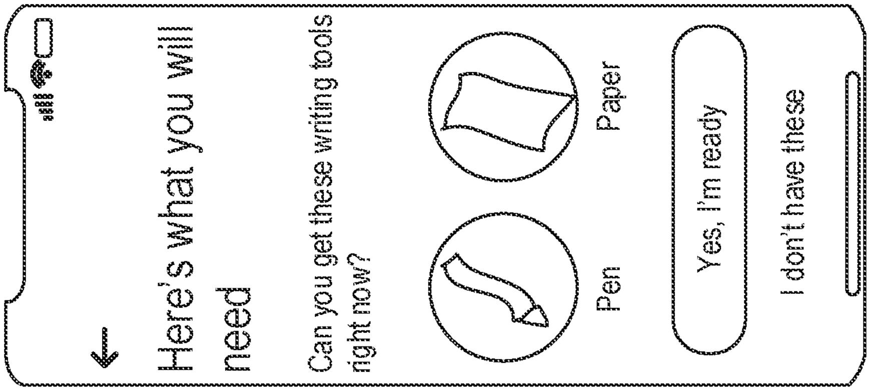
Figure 8H:
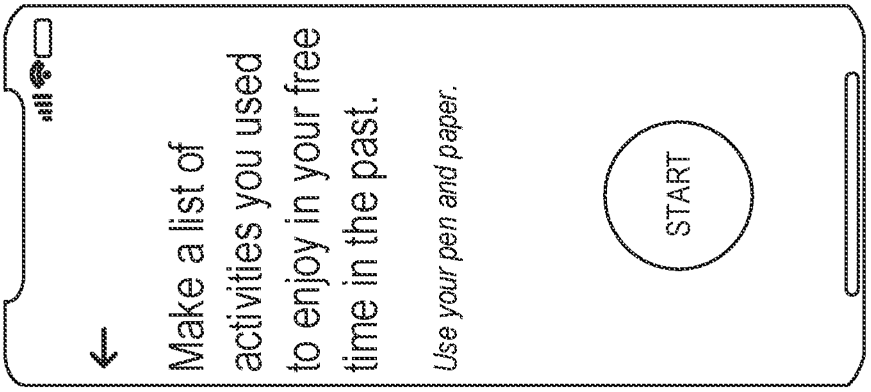
Figure 8I:
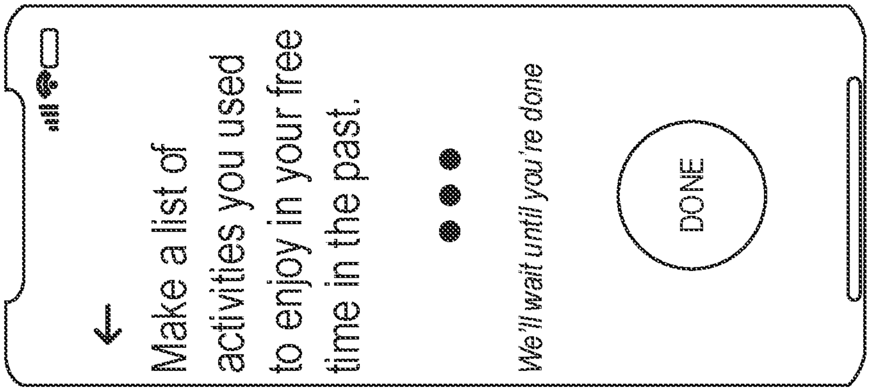
Figure 8J:
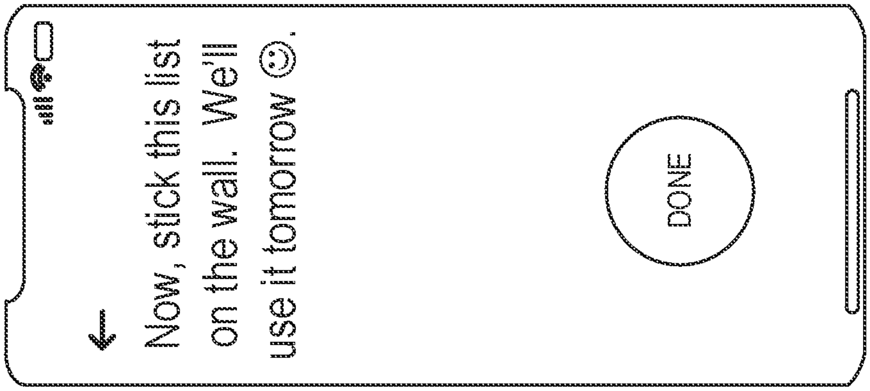
Figure 8K:
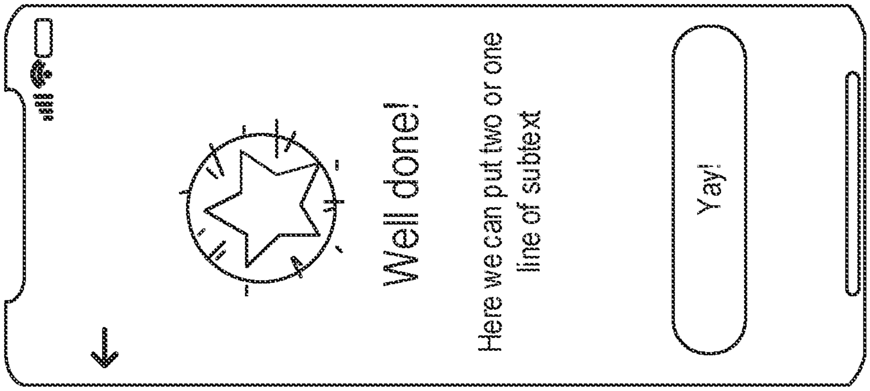
Figure 8L:
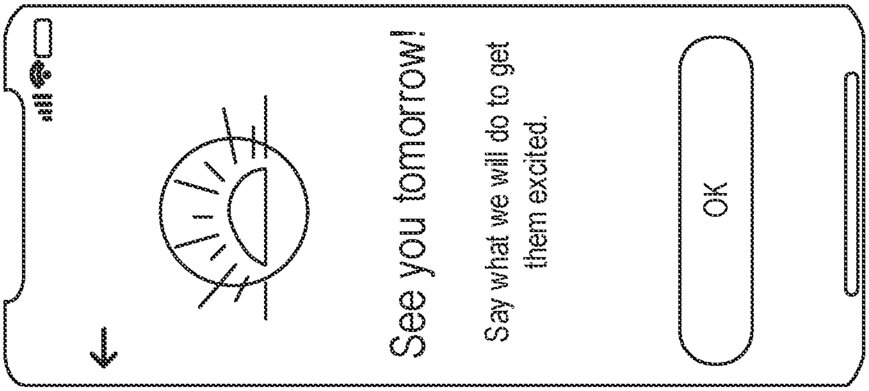
Figures 9A, 9B, 9C, 9D:
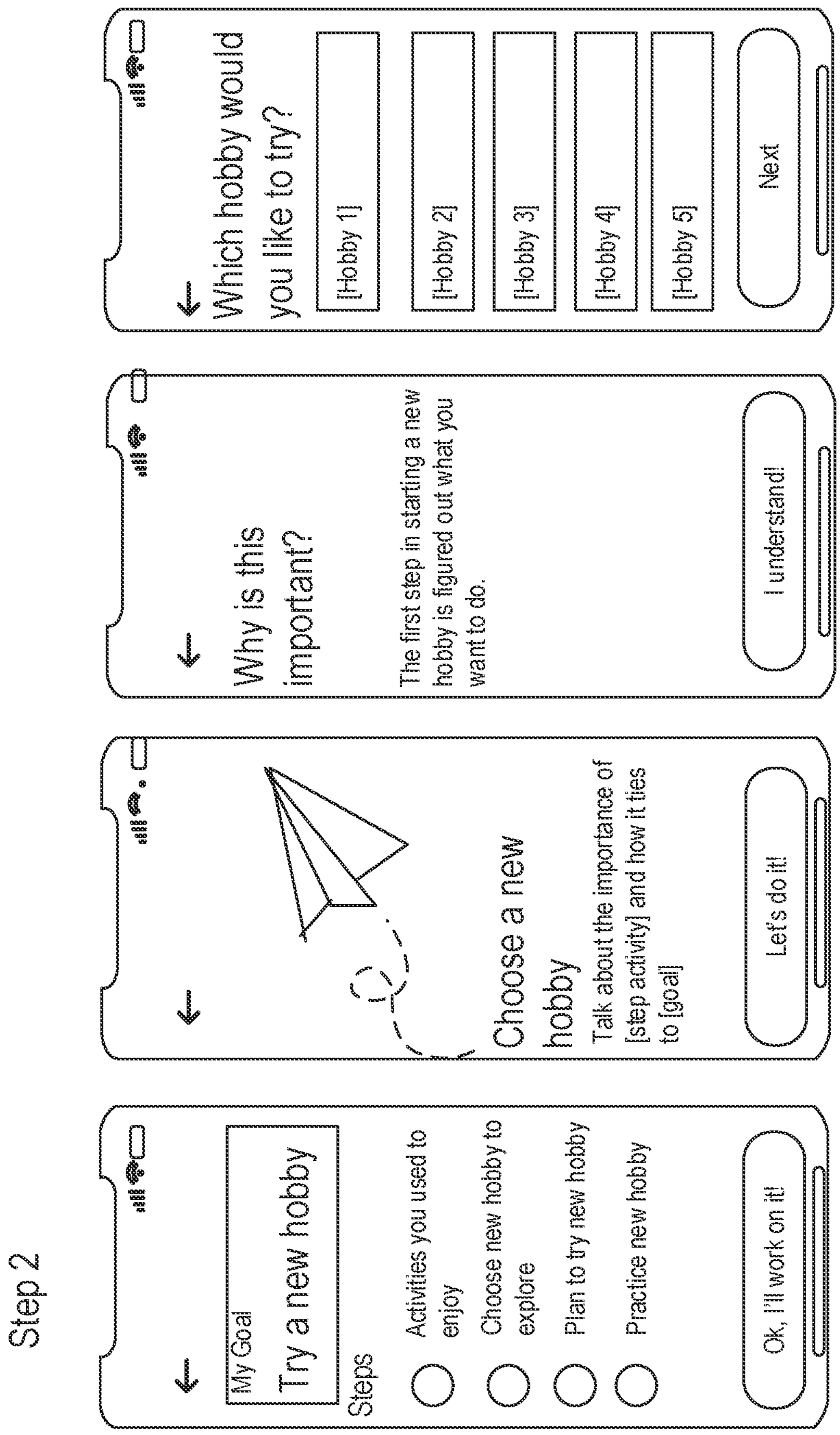
FIGS. 9A-L each depict examples of screenshots of prompts for a user to perform activities associated with an endpoint to pursue a hobby at a second step of a level 0, in accordance with an illustrative embodiment.
Figure 9E:
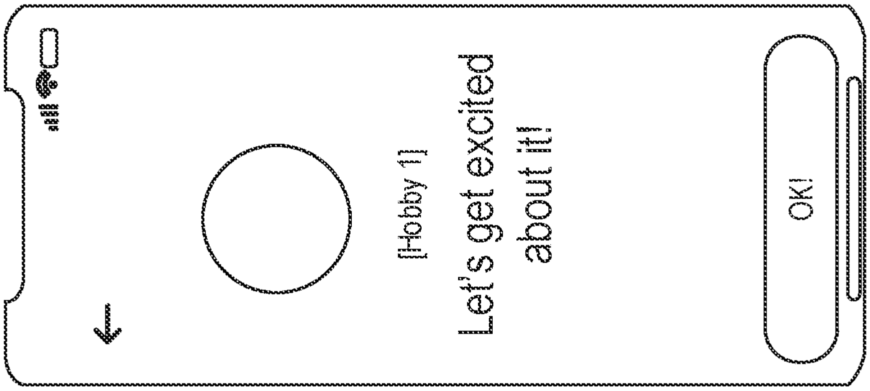
Figure 9F:
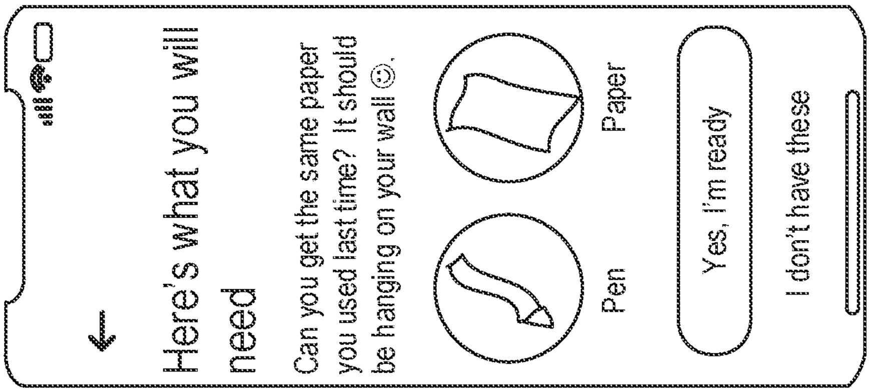
Figure 9G:
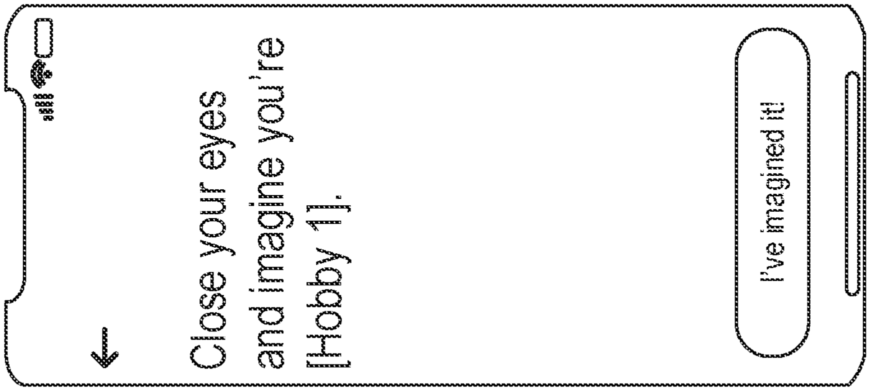
Figure 9H:
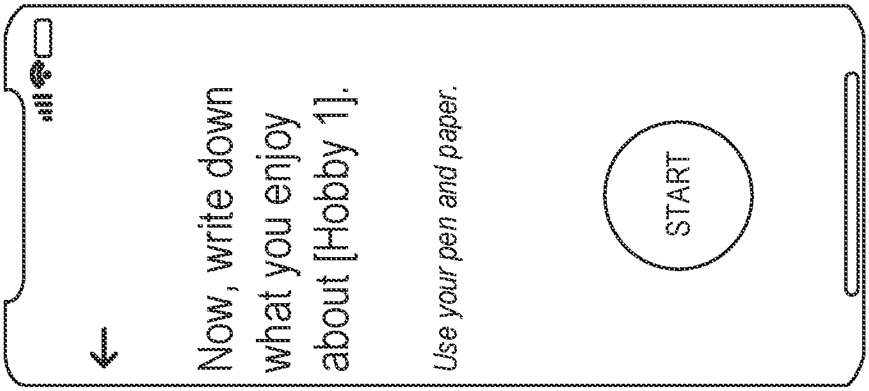
Figure 9I:
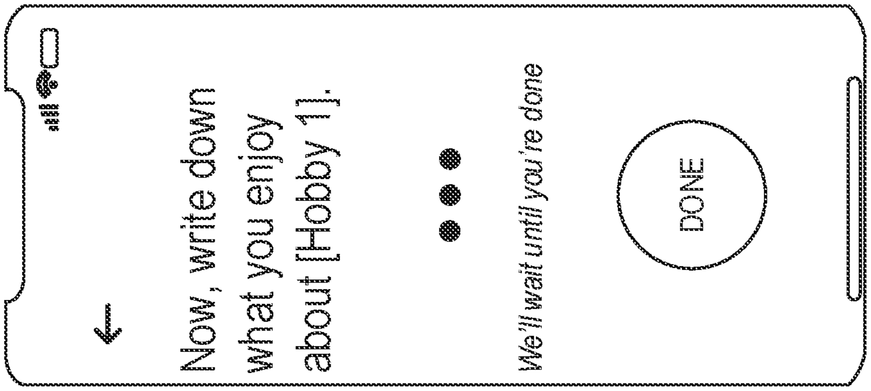
Figure 9J:
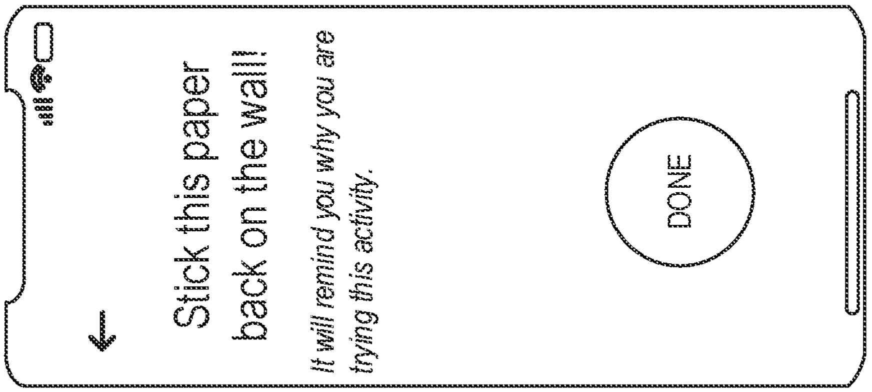
Figure 9K:
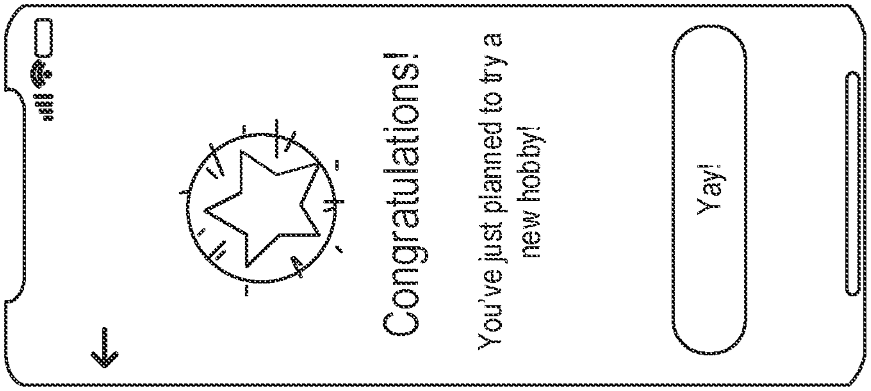
Figure 9L:
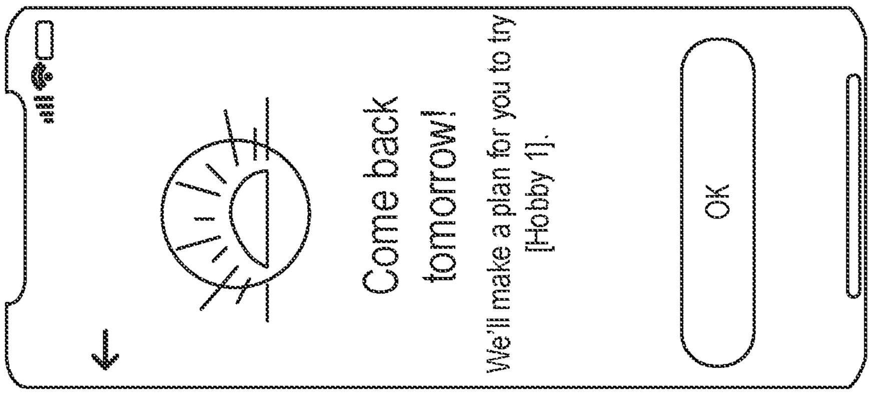
Figure 10A:
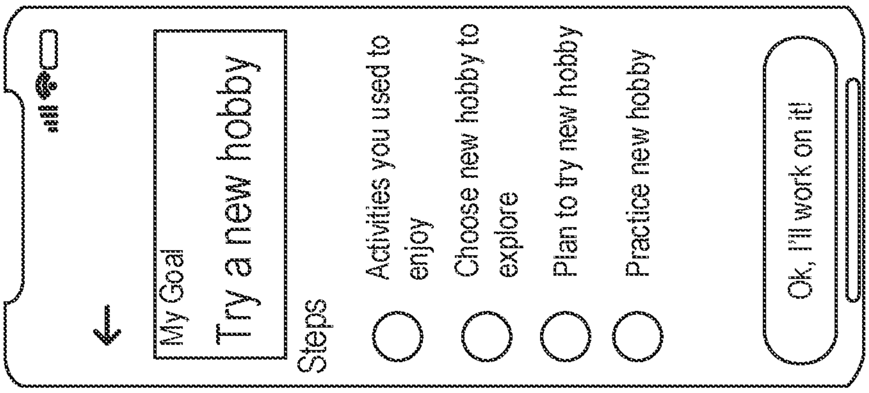
FIGS. 10A-J each depict examples of screenshots of prompts for a user to perform activities associated with an endpoint to pursue a hobby at a third step of a level 0, in accordance with an illustrative embodiment.
Figure 10B:
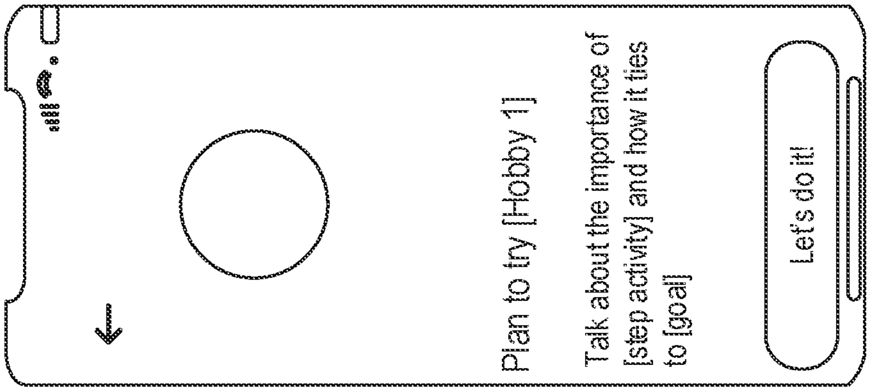
Figure 10C:
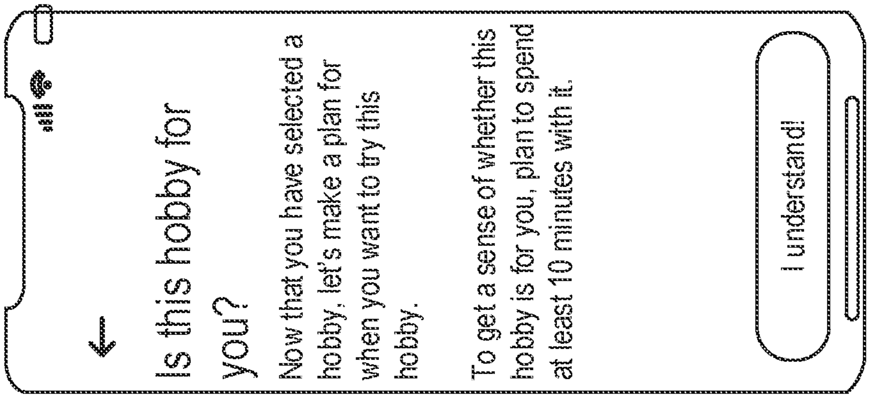
Figure 10D:
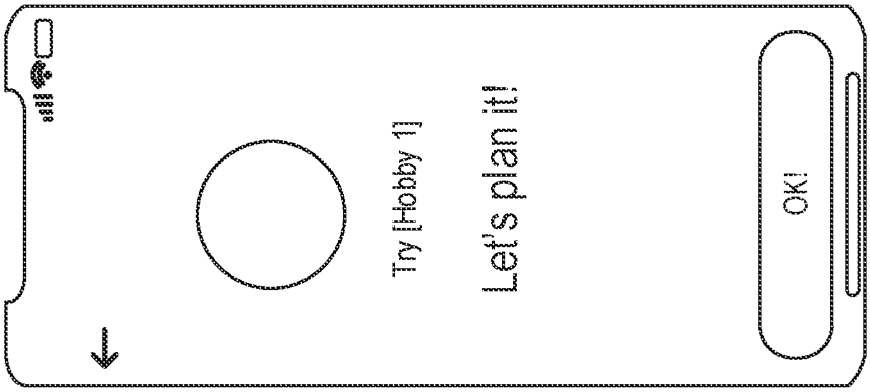
Figure 10E:
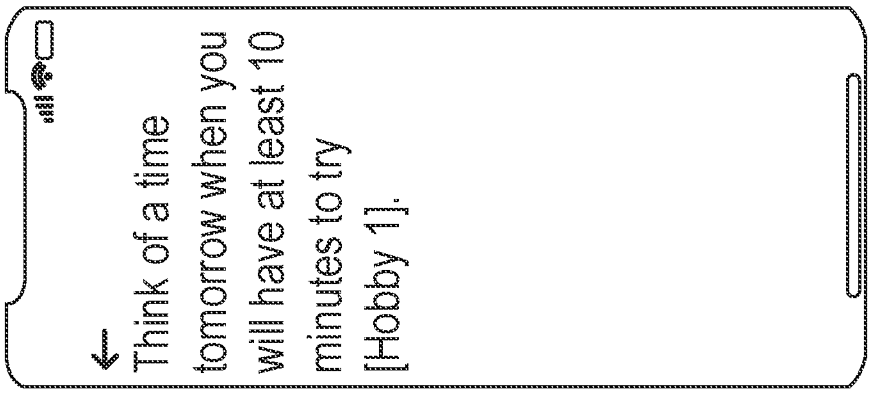
Figure 10F:
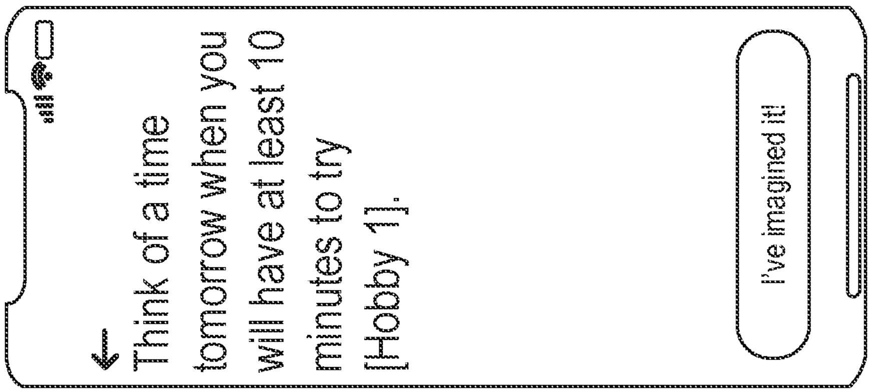
Figure 10G:
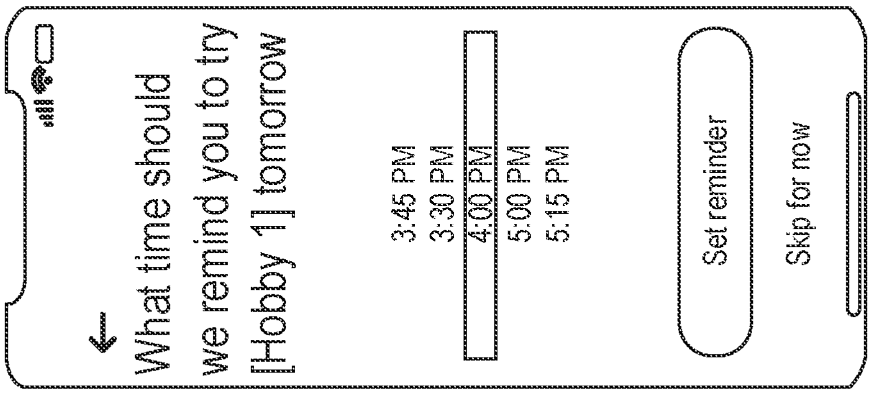
Figure 10H:
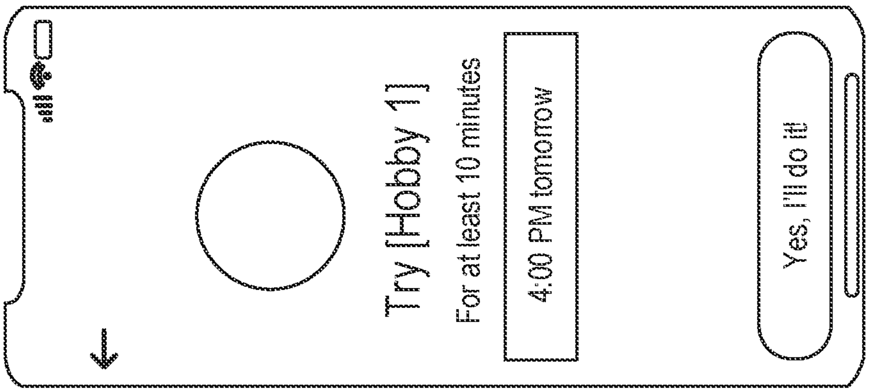
Figure 10I:
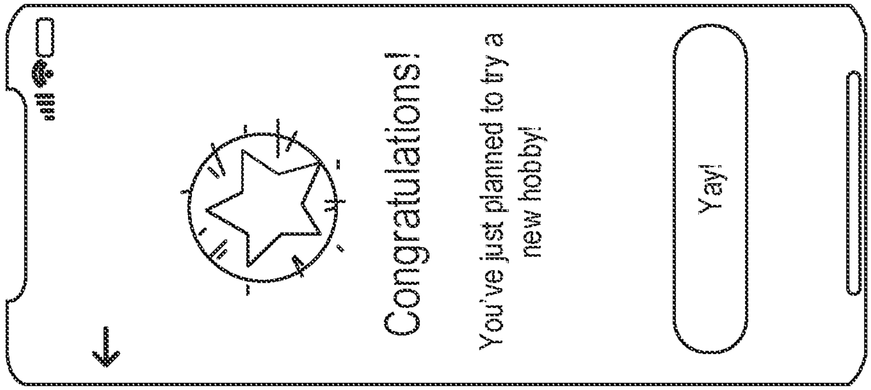
Figure 10J:
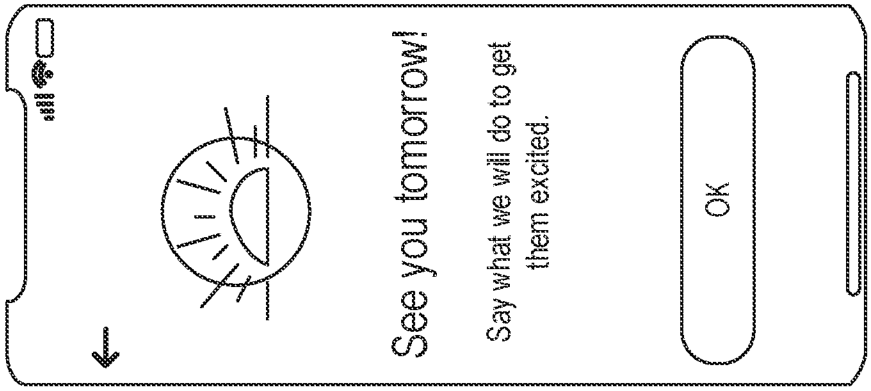
Figure 11A:
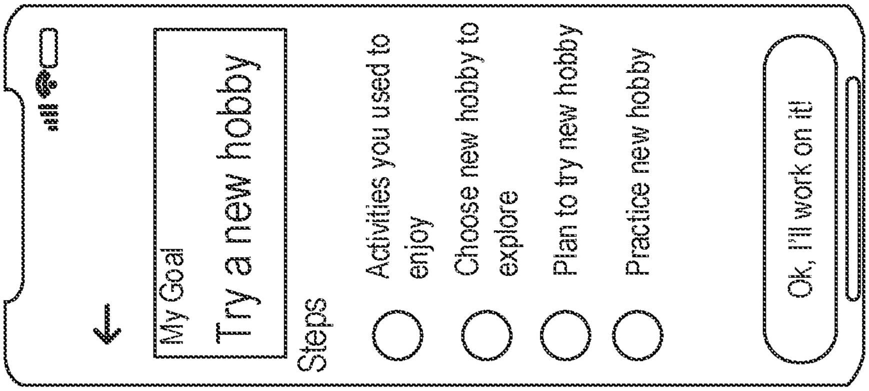
FIGS. 11A-G each depict examples of screenshots of prompts for a user to perform activities associated with an endpoint to pursue a hobby at a fourth step of a level 0, in accordance with an illustrative embodiment.
Figure 11B:
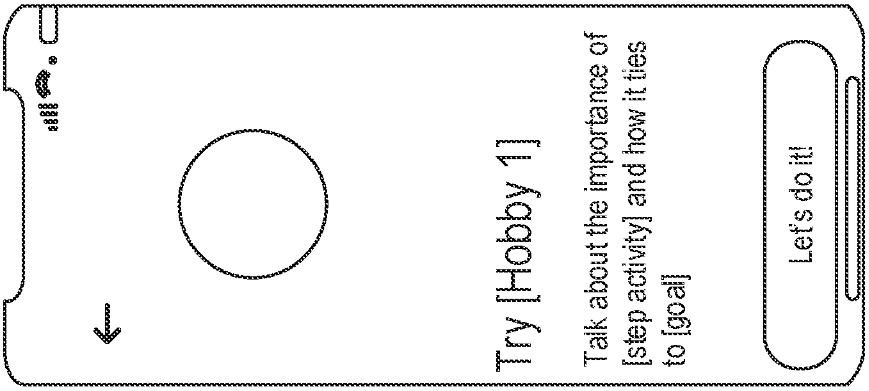
Figure 11C:
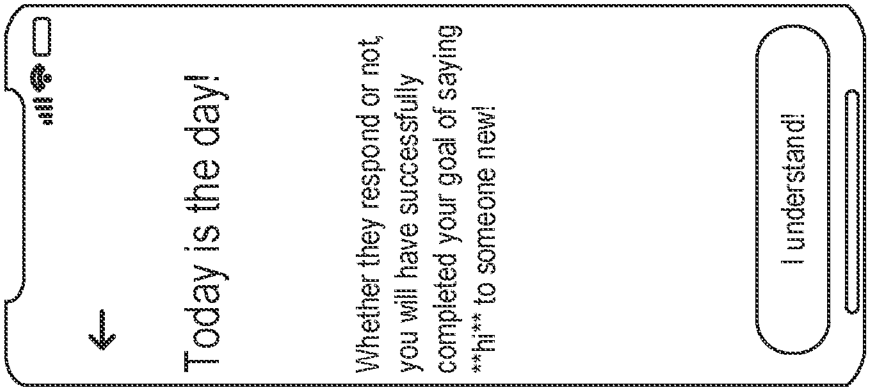
Figure 11D:
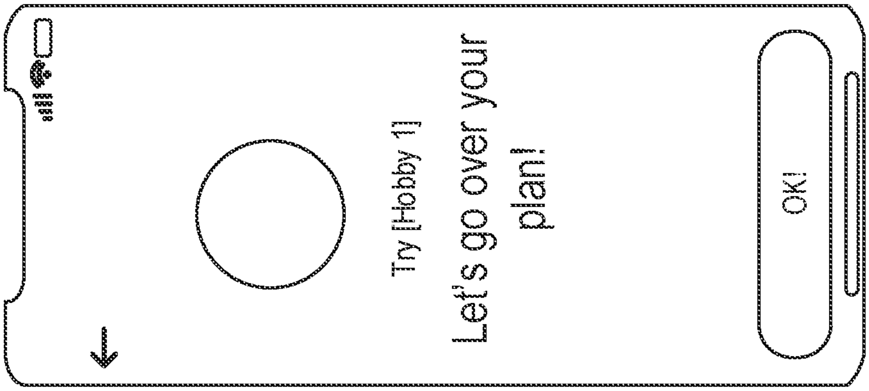
Figures 11E, 11F, 11G:
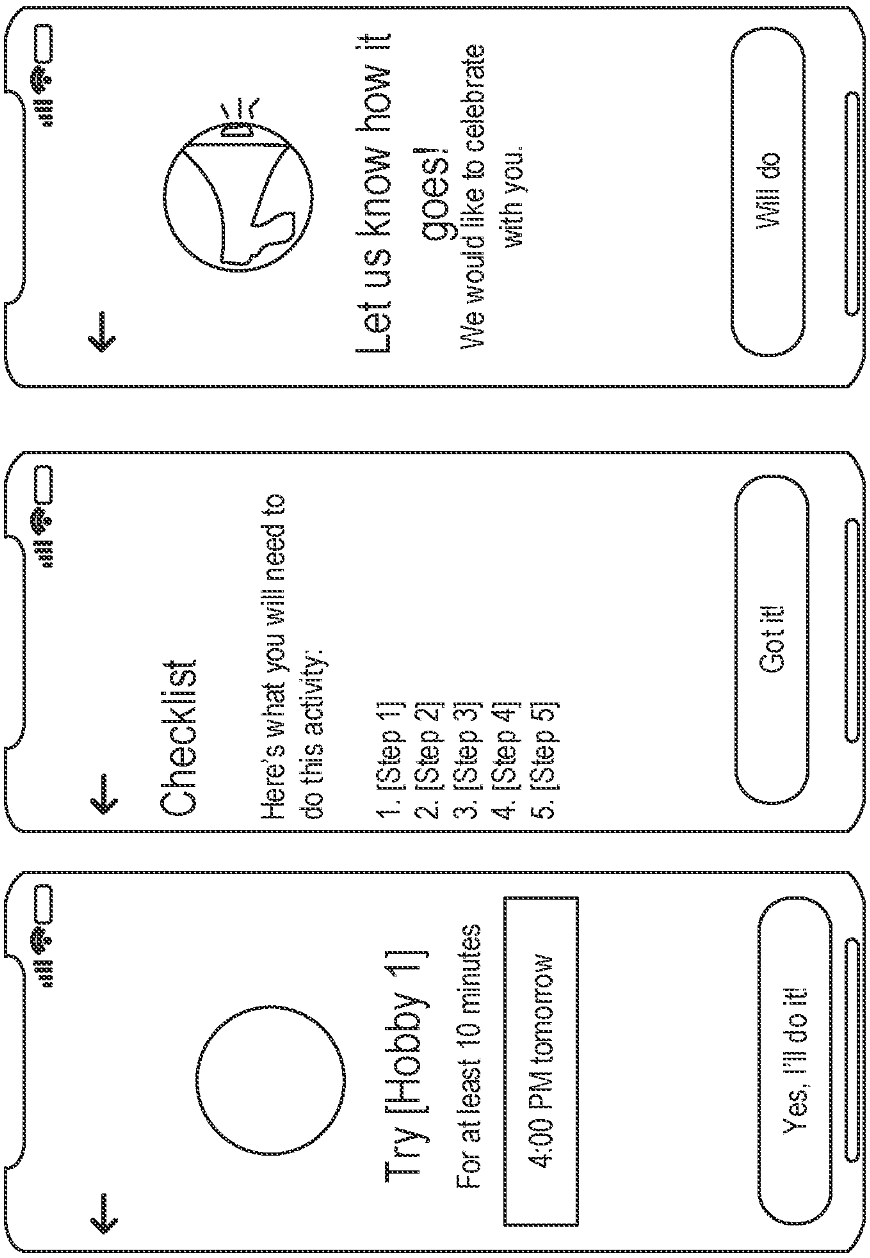
Figure 12A:
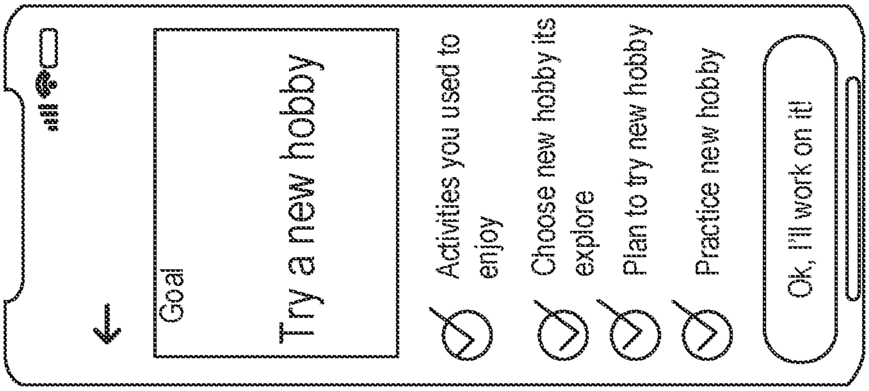
FIGS. 12A-D each depict examples of screenshots of prompts for a user to perform activities associated with an endpoint to pursue a hobby at a first step of a level 1, in accordance with an illustrative embodiment.
Figure 12B:
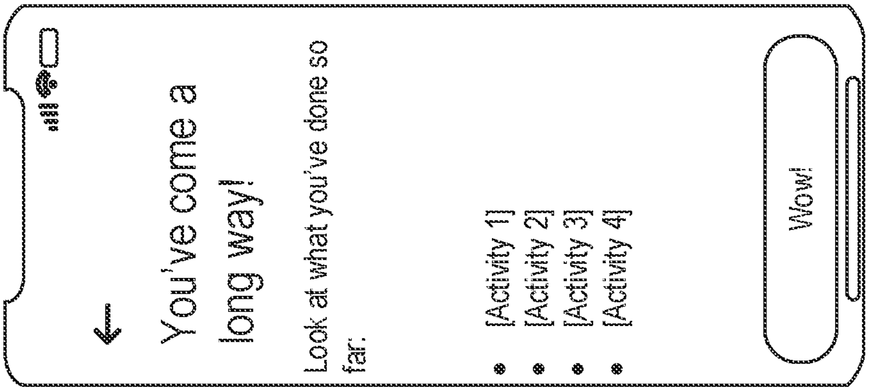
Figure 12C:
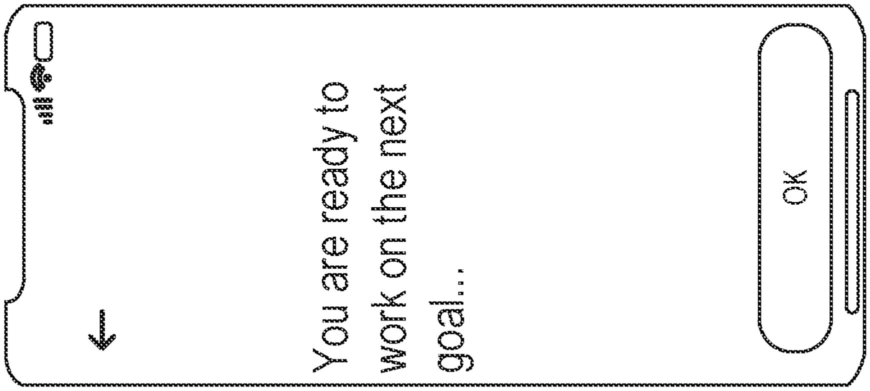
Figure 12D:
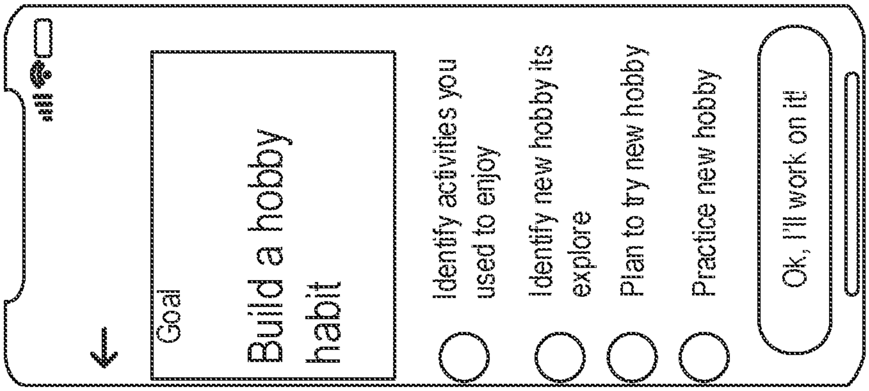
Figure 13A:
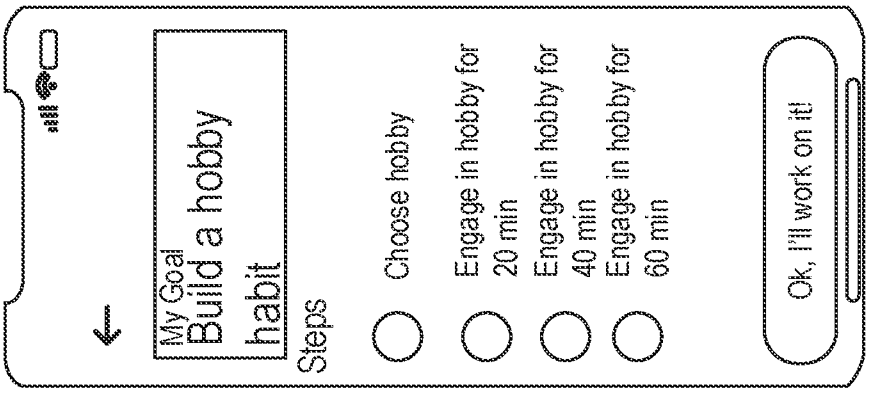
FIGS. 13A-K each depict examples of screenshots of prompts for a user to perform activities associated with an endpoint to pursue a hobby at a second step of a level 1, in accordance with an illustrative embodiment.
Figure 13B:
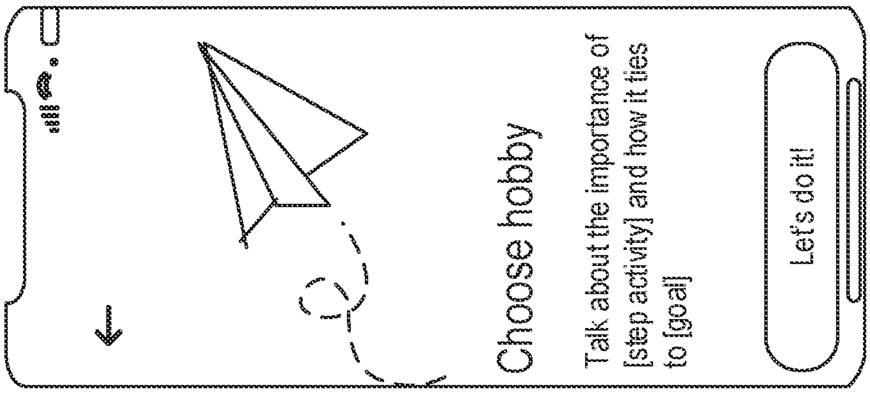
Figure 13C:
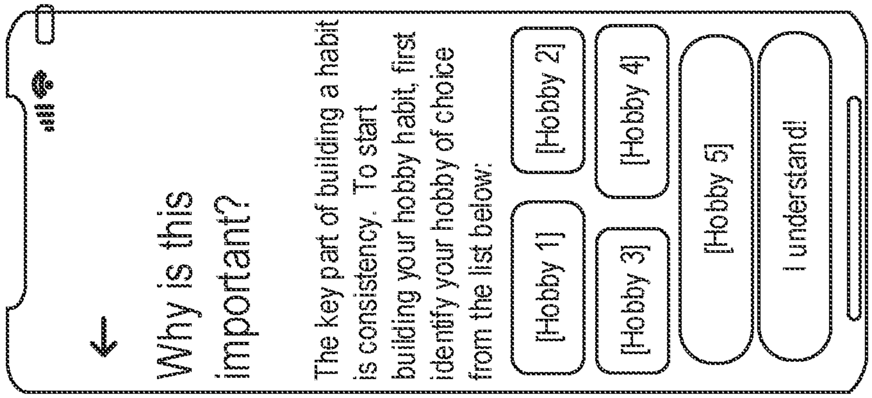
Figure 13D:
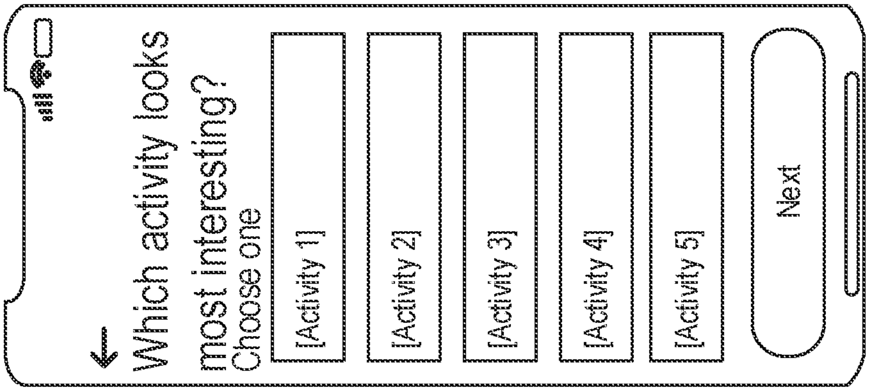
Figure 13E:
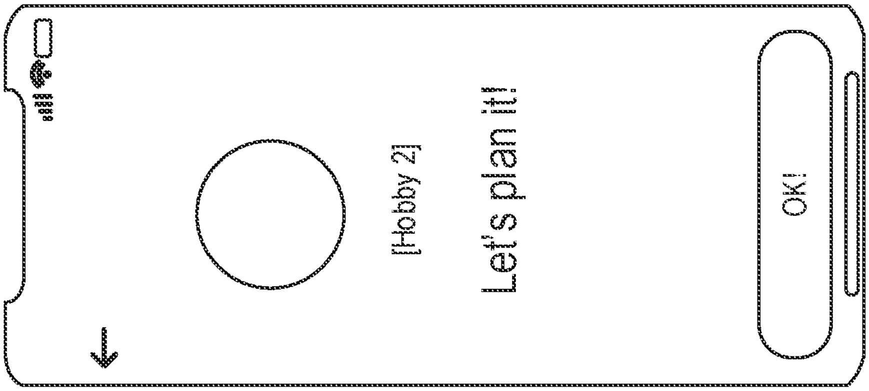
Figure 13F:
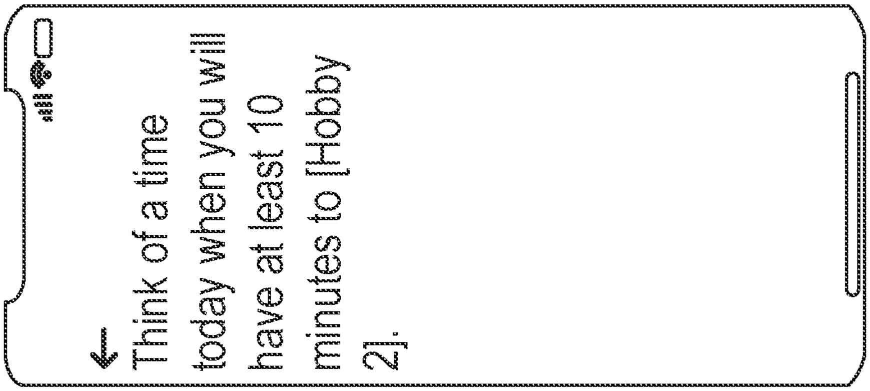
Figure 13G:
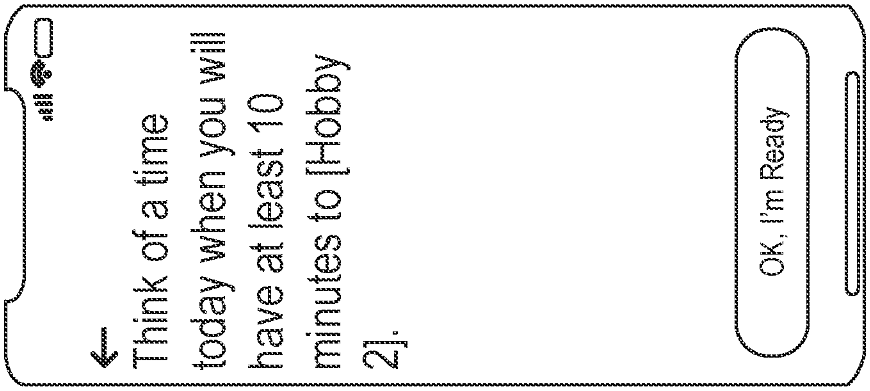
Figure 13H:
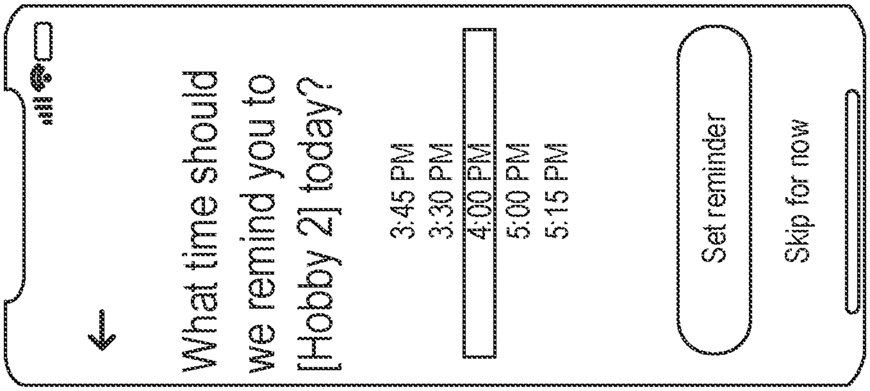
Figure 13I:
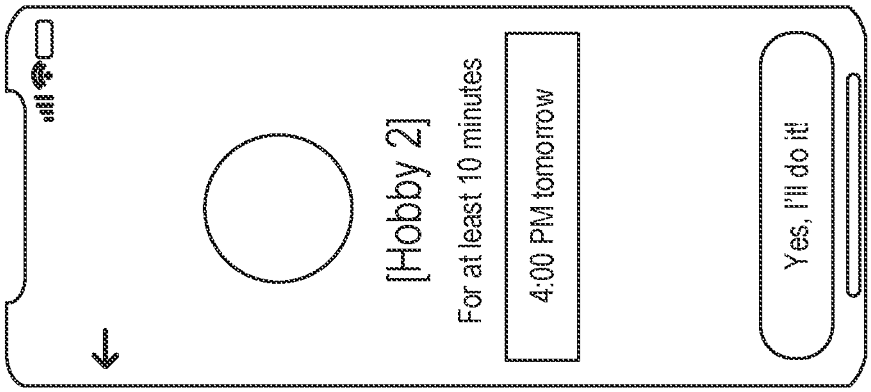
Figure 13J:
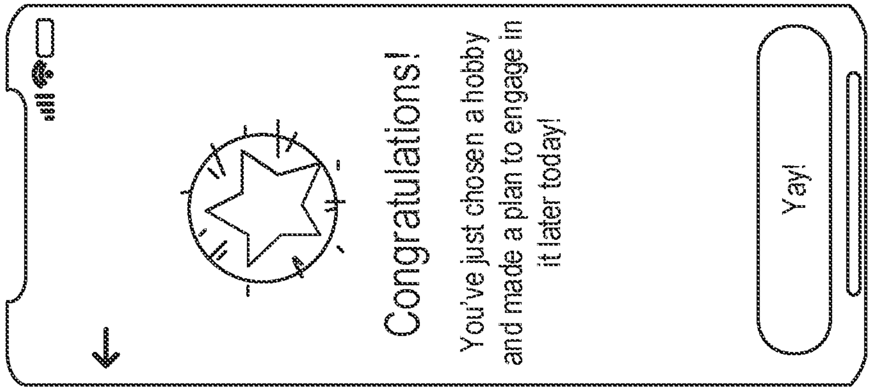
Figure 13K:
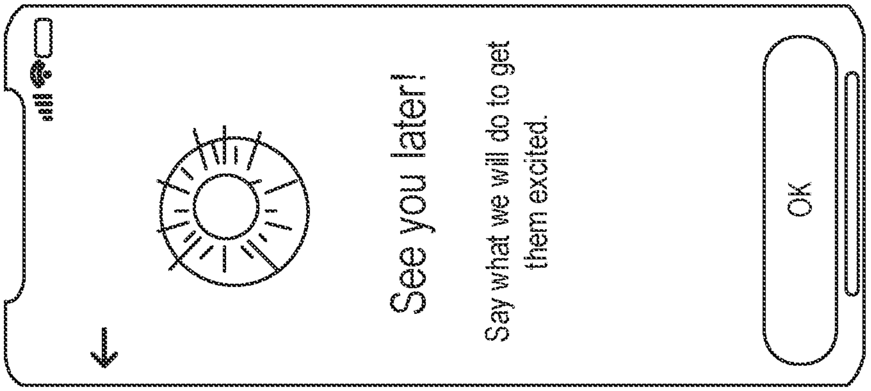
Figure 14A:
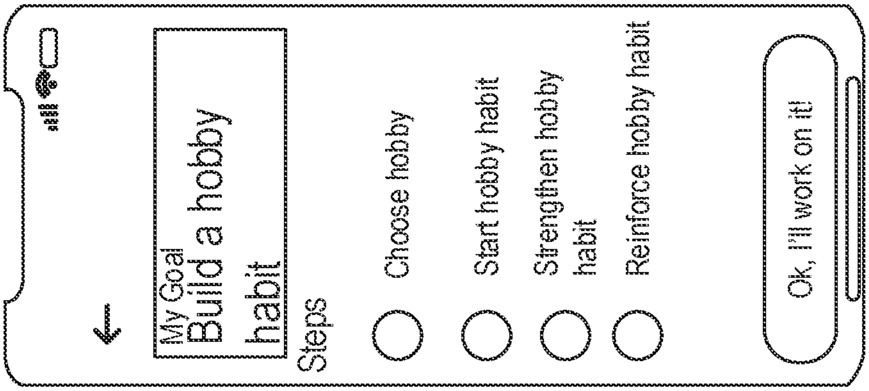
FIGS. 14A-J each depict examples of screenshots of prompts for a user to perform activities associated with an endpoint to pursue a hobby at a third step of a level 1, in accordance with an illustrative embodiment.
Figure 14B:
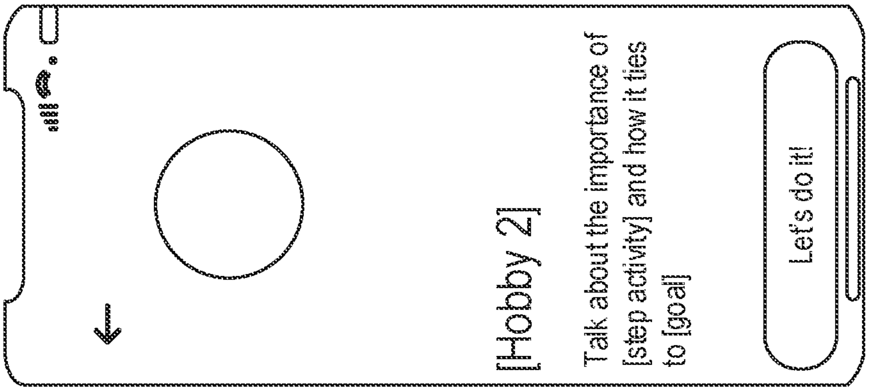
Figure 14C:
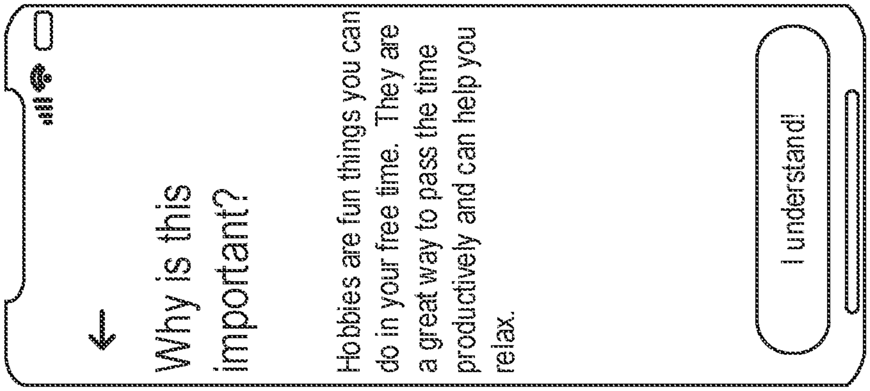
Figure 14D:
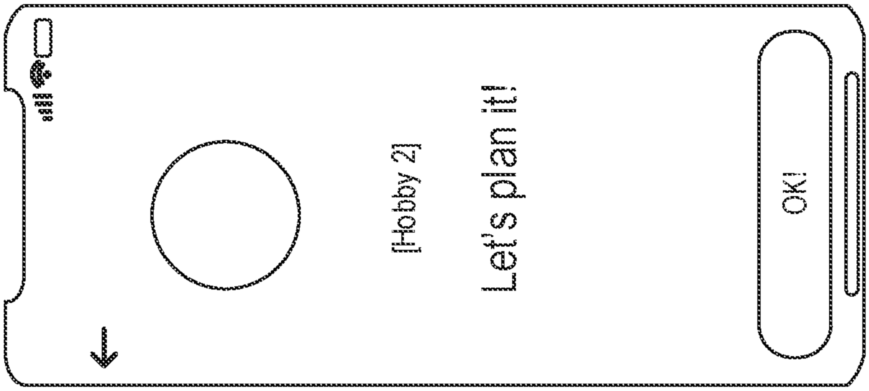
Figure 14E:
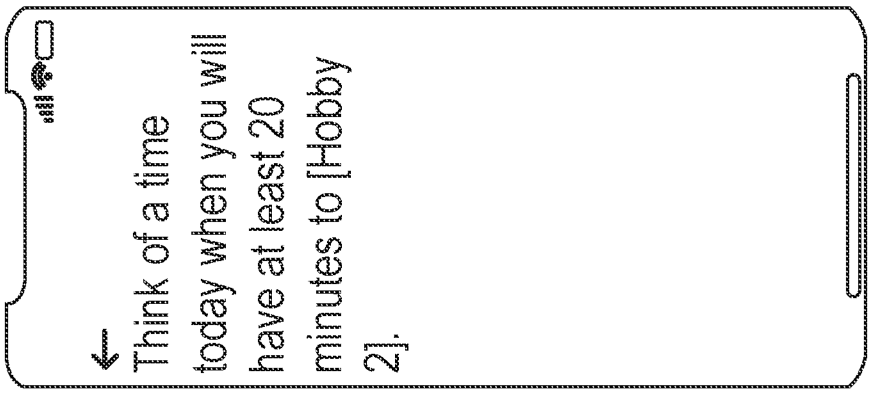
Figure 14F:
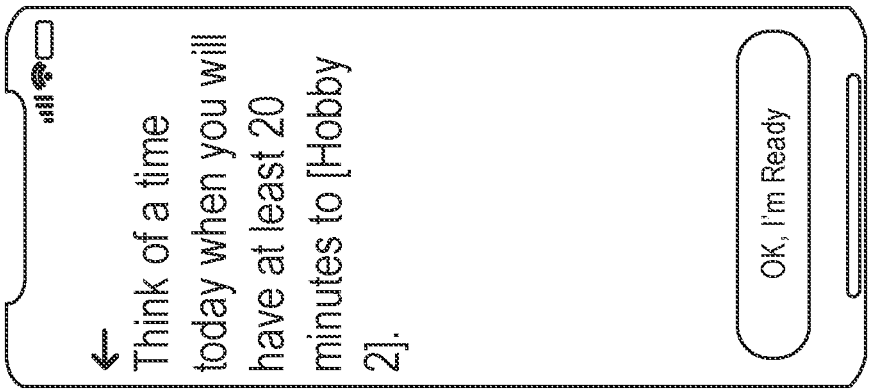
Figure 14G:
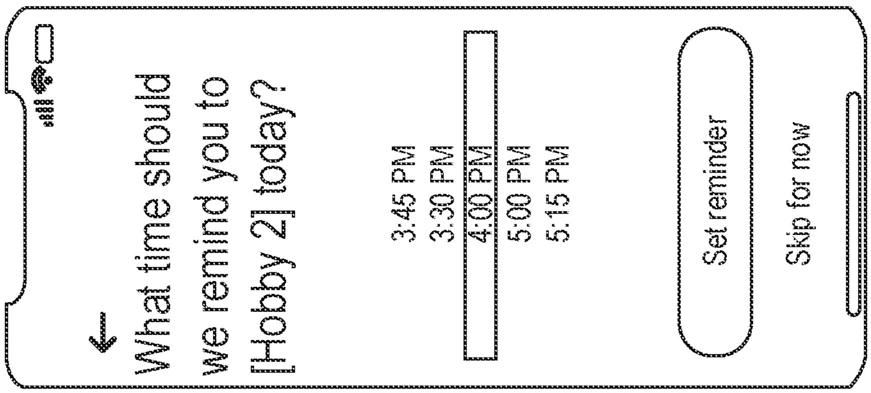
Figure 14H:
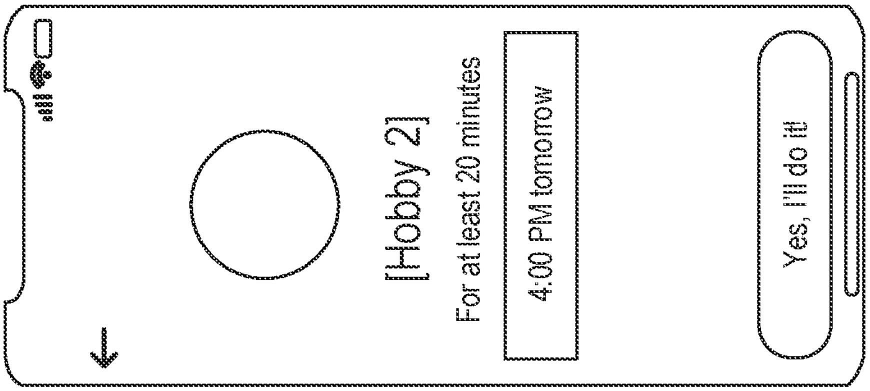
Figure 14J:
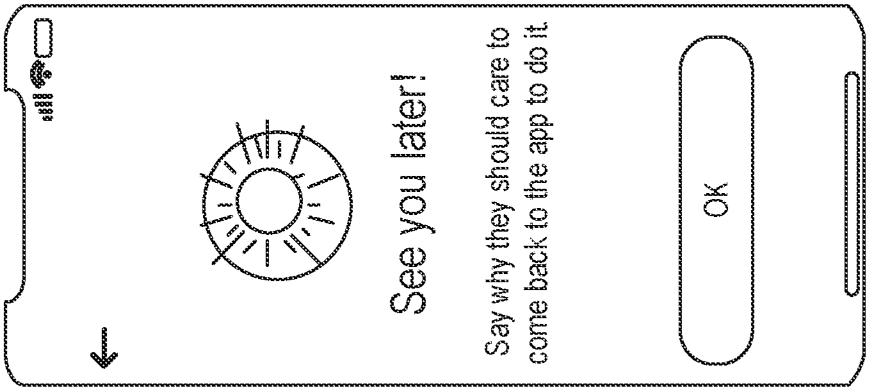
Figure 14I:
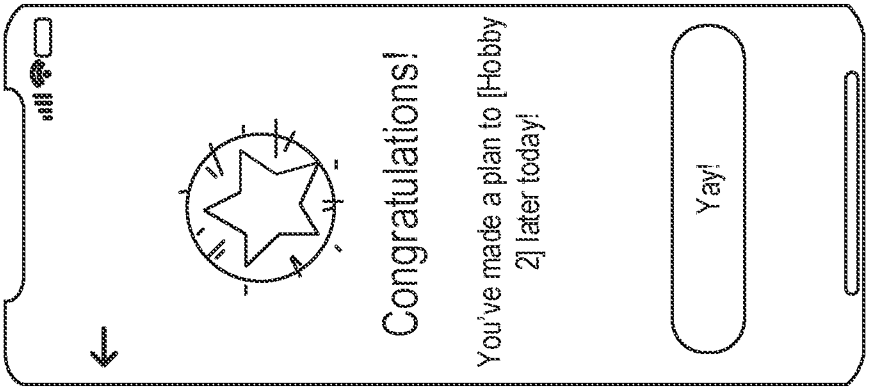
Figure 15A:
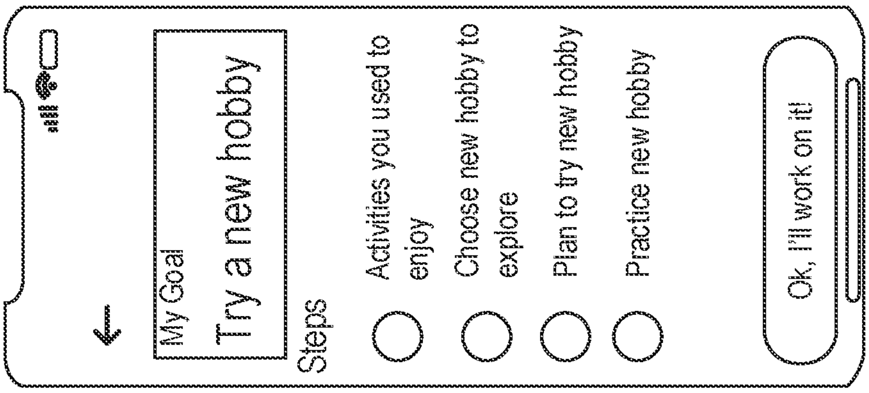
FIGS. 15A-J each depict examples of screenshots of prompts for a user to perform activities associated with an endpoint to pursue a hobby at a third step of a level 1, in accordance with an illustrative embodiment.
Figure 15B:
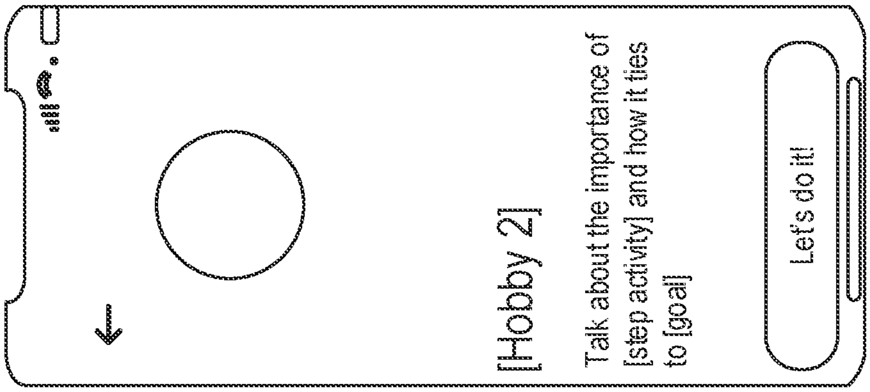
Figure 15C:
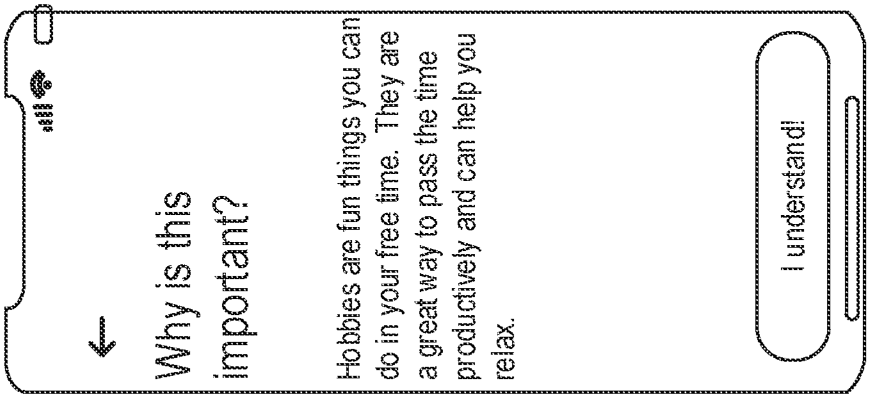
Figure 15D:
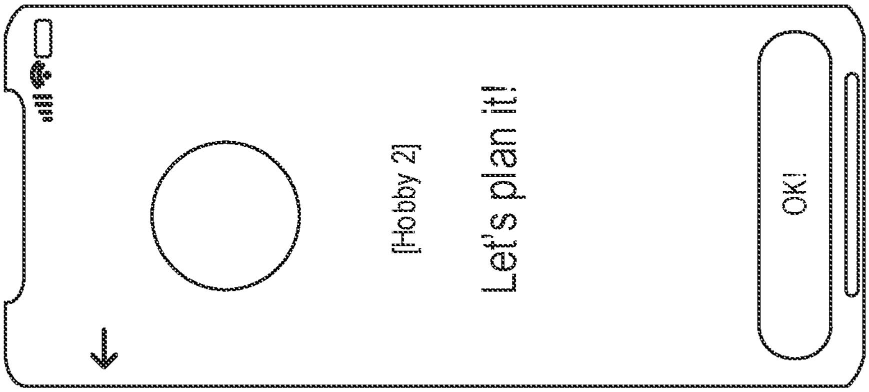
Figure 15E:
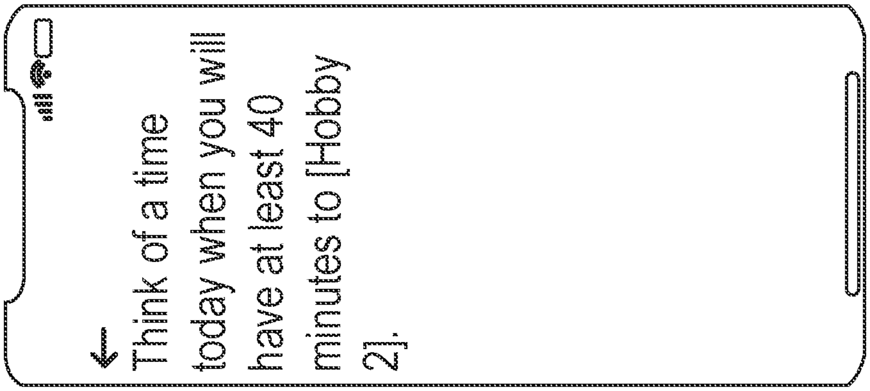
Figure 15F:
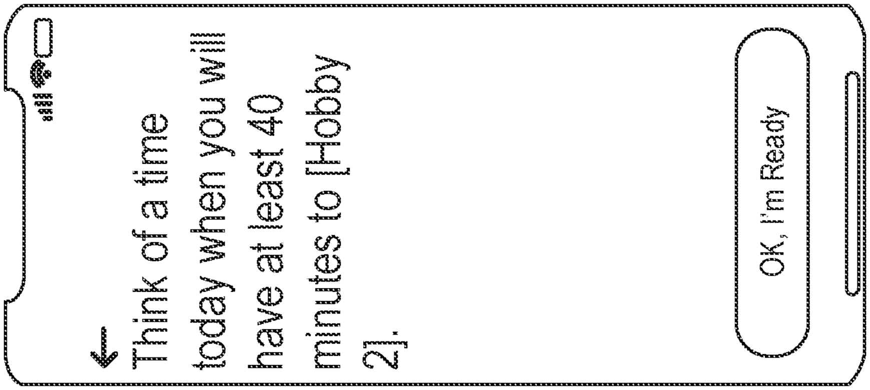
Figure 15G:
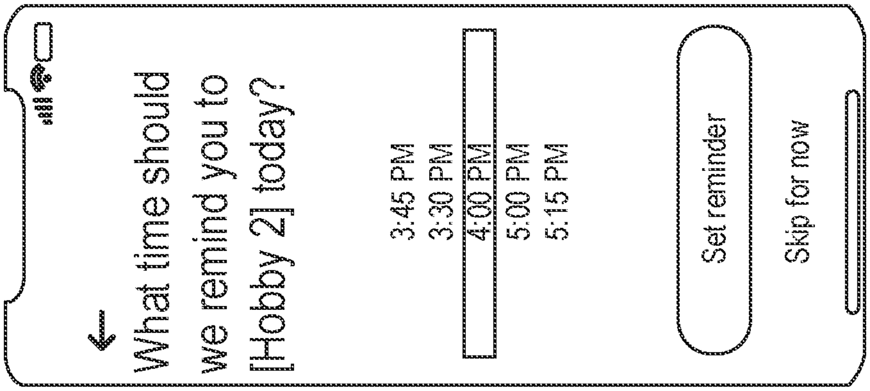
Figure 15H:
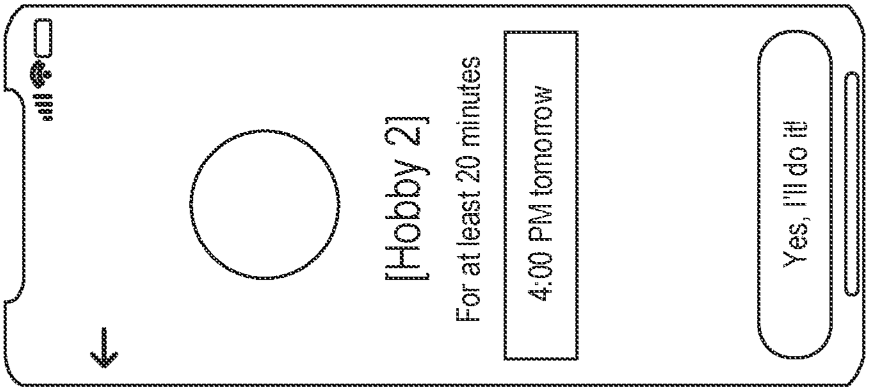
Figure 15I:
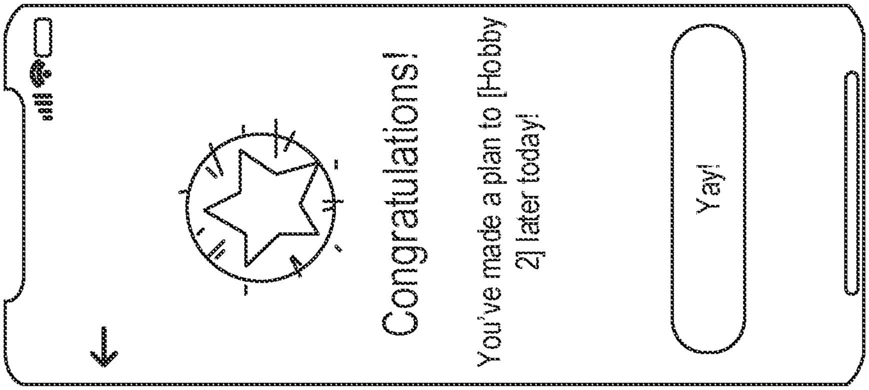
Figure 15J:
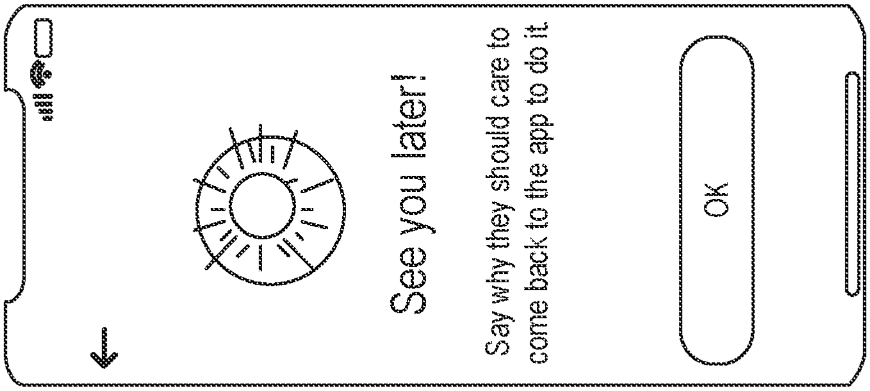
Figure 16A:
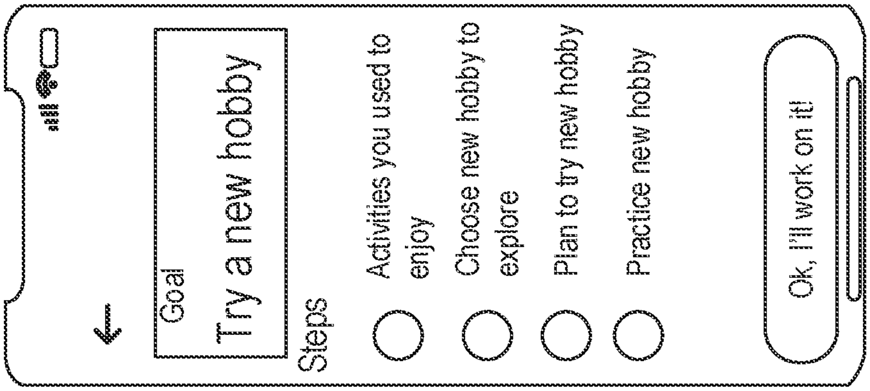
FIGS. 16A-J each depict examples of screenshots of prompts for a user to perform activities associated with an endpoint to pursue a hobby at a fourth step of a level 1, in accordance with an illustrative embodiment.
Figure 16B:
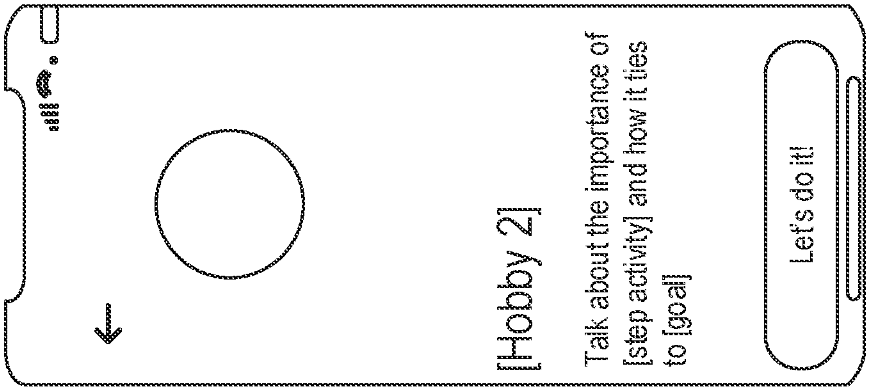
Figure 16C:
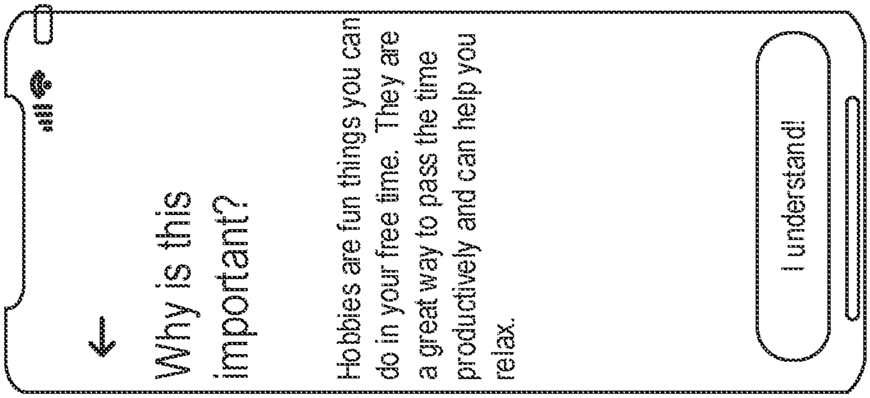
Figure 16D:
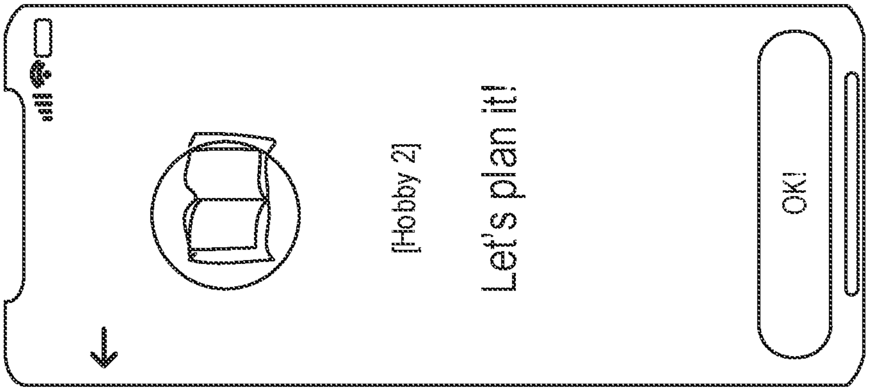
Figure 16E:
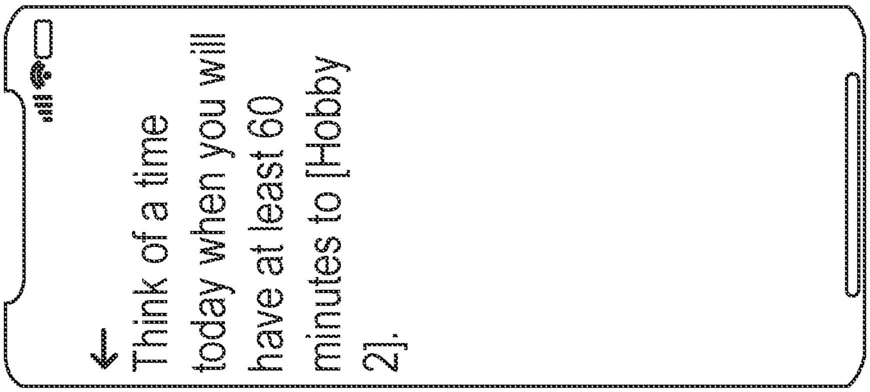
Figure 16F:
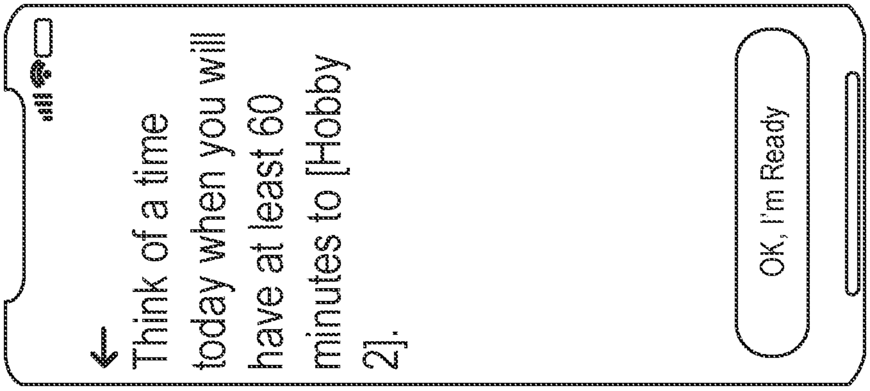
Figure 16G:
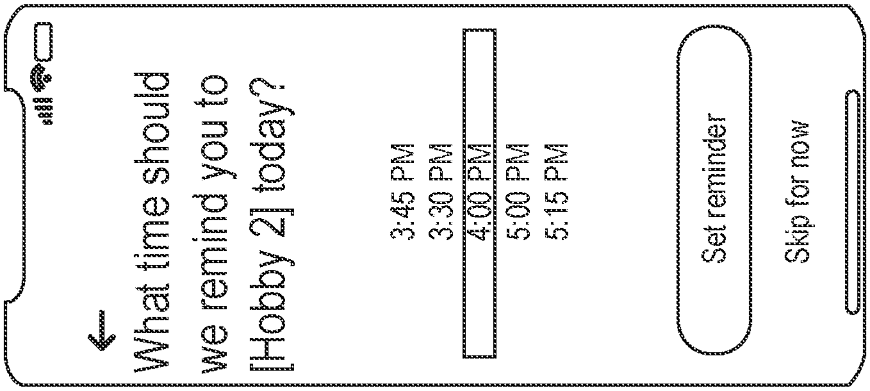
Figure 16H:
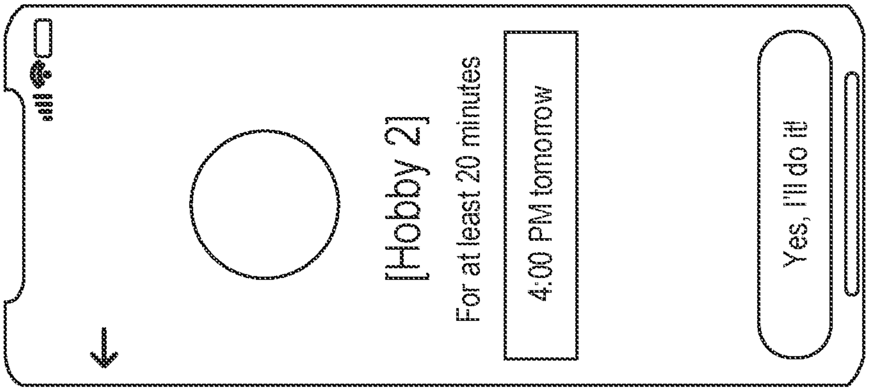
Figure 16I:
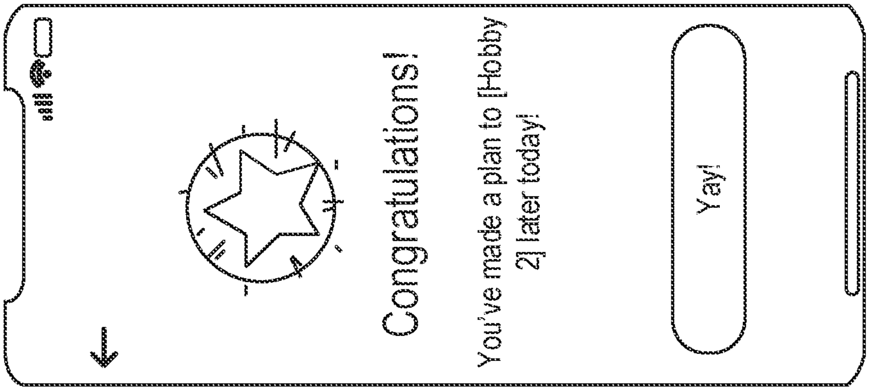
Figure 16J:
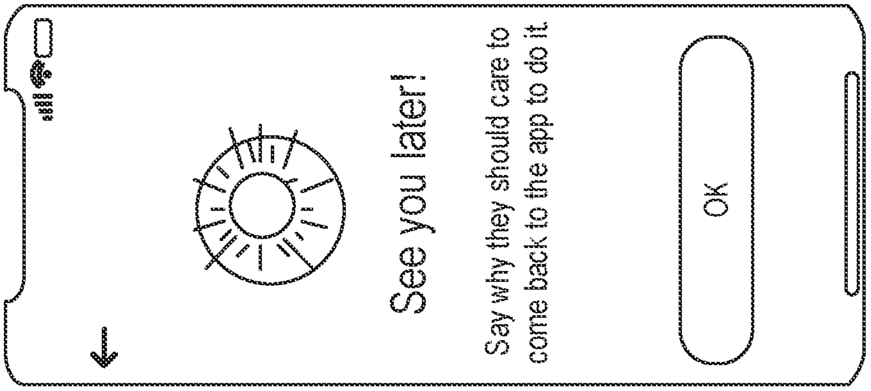
Figure 17B:
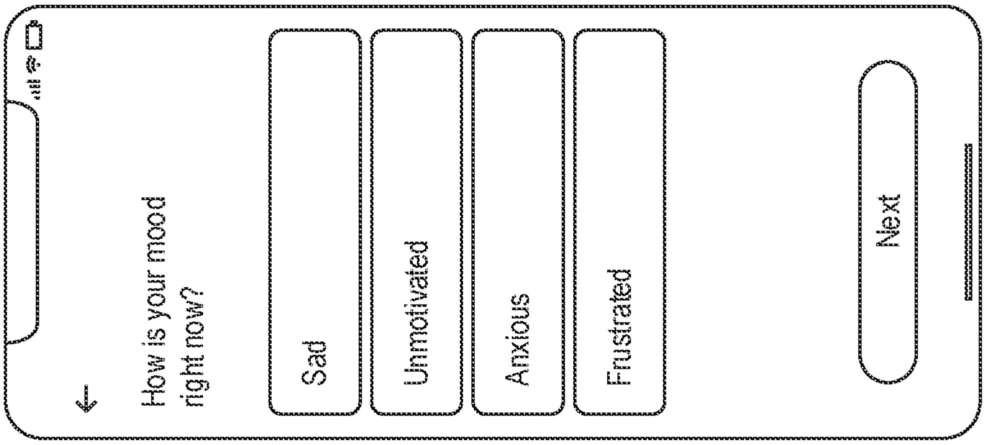
FIGS. 17A-G each depict examples of screenshots of prompts for a user to indicate a mood of the user used to select next endpoints, in accordance with an illustrative embodiment.
Figure 17A:
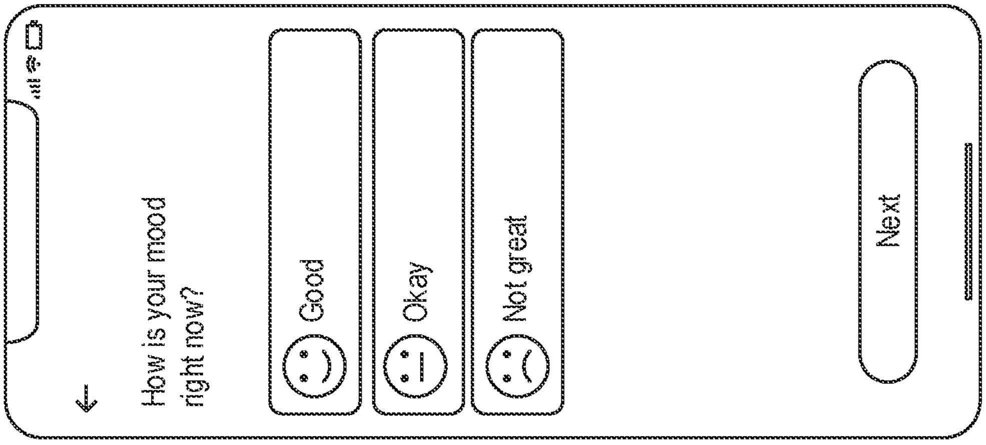
Figure 17C:
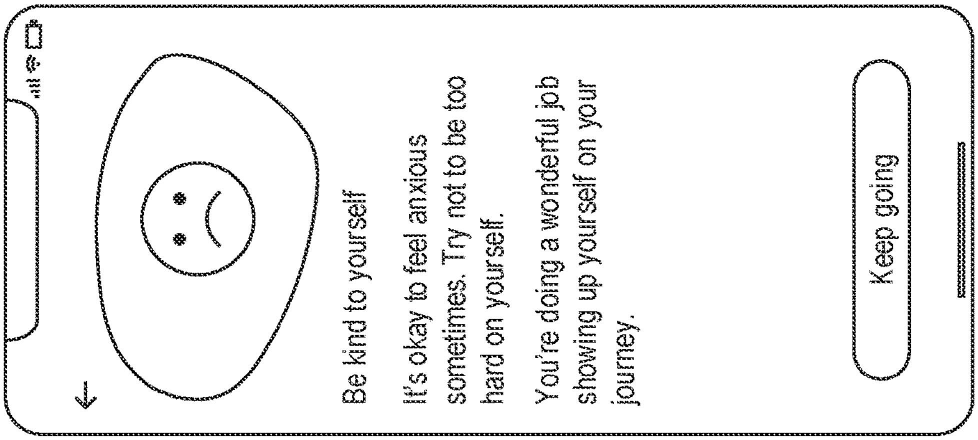
Figure 17D:
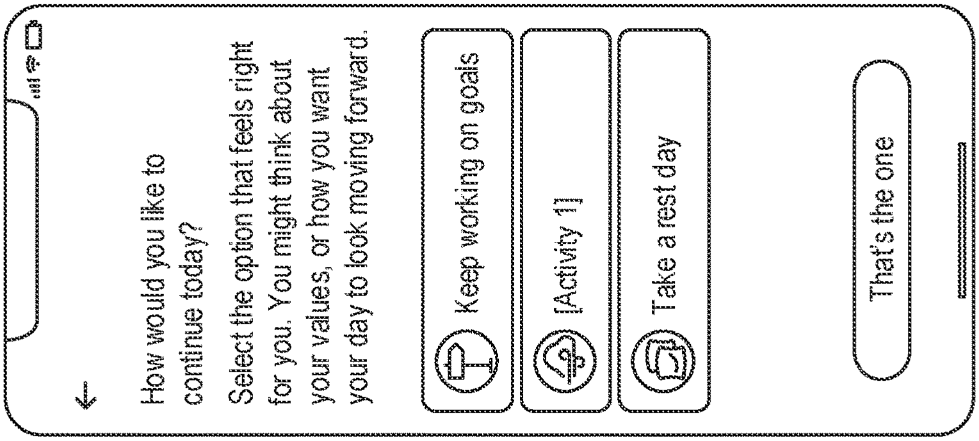
Figure 17E:
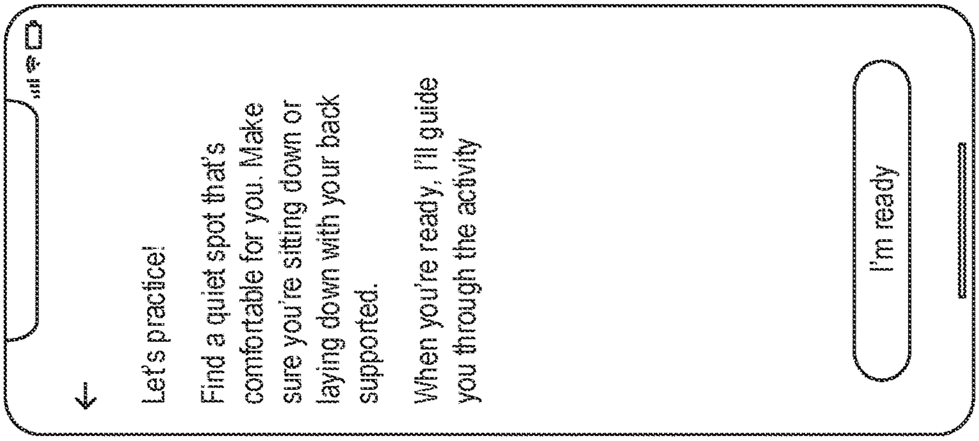
Figure 17F:
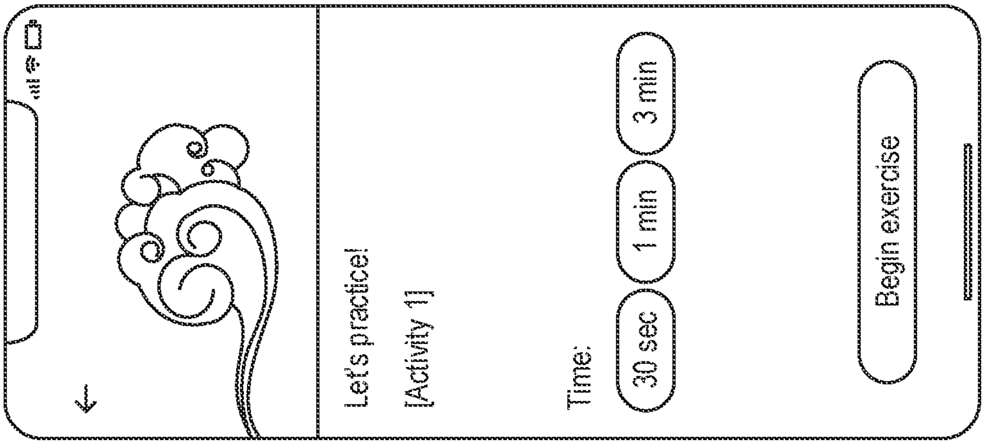
Figure 17G:
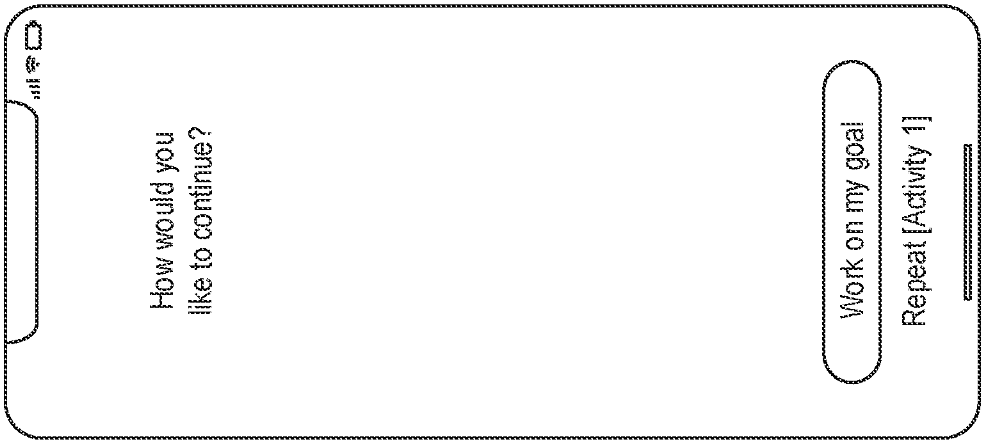

In some embodiments, the set of questions to be presented by the questionnaire prompt 224 may be in accordance with a questionnaire policy. The questionnaire policy may identify a rule for selecting questions depending on the responses to previous questions within the set. The responses to the questions may be used to generate the user profile 160 for the user 222. For example, the questionnaire may specify presentation of a subset of questions on frequency, duration, and level for the hobby of Hobby A, when the user 222 has responded a preference for Hobby A as the type of activity to be performed and recorded via the application 165. In some embodiments, the questionnaire may be a validated clinical assessment in relation to a physical or psychological (or mental) condition, such as: the Structured Clinical Interview for the Diagnostic and Statistical Manual of Mental Disorders (DSM) (SCID) to assess diagnoses from the DSM; Mini-international neuropsychiatric interview (MINI); the clinical assessment interview for negative symptoms (CAINS) scale, which assesses the motivation and pleasure domain of negative symptoms; and Hamilton Depression Rating Scale (HDRS), among others. Examples of the prompt 224 and the set of questions presented therein are shown herein in FIGS. 7A-F (related to physical activity of the user). In the depicted example, the questionnaire policy may specify that the prompt 224 is to present a question on how much time the user spent in performing a physical activity (FIG. 7B), when the answer to the previous question on whether the physical activity was performed is in the affirmative (FIG. 7A).

Using the responses to the questions presented via the prompt 224, the profile creator 170 may determine or generate one or more parameters 226A-N (hereinafter generally referred to as parameters 226). The parameter 226 may identify or include any number of factors to be used to select one or more configuration files 155 to be provided to the application 165. The parameters 226 may identify the endpoint to be achieved and the condition of the user 222 to be addressed. The parameters 226 may identify the state of the user 222 (e.g., mood, emotional, behavioral, physiological state). The parameters 226 may identify a type of activity, a frequency, duration, and time (e.g., day of week or time of day) for the routine, among others, as indicated by the user 222 via the prompt 224. In some embodiments, the parameters 226 may identify an identifier for the user device 110, a device type of the user device 110, an identifier for the application 165, and a location of the user 222, among others. With the generation, the profile creator 170 may include the one or more parameters 226 into the user profile 160. The inclusion of the user profile 160 may be in accordance with a template. The template may include fields in which to include or insert the values of the parameters 226. The profile creator 170 may send, transmit, or otherwise provide the user profile 160 to the application configuration service 105. The user profile 160 may be sent as part of a message to the application configuration service 105.

The profile assessor 130 executing on the application configuration service 105 may retrieve, receive, or otherwise identify the user profile 160 from the user device 110. In some embodiments, the profile assessor 130 may be executing on the user device 110 as part of the application 165, for example, to evaluate the user profile 160 generated by the profile creator 170 on the user device 110. Upon receipt from the user device 110, the profile assessor 130 may store and maintain the user profile 160 on the database 115. In some embodiments, the profile assessor 130 may fetch, retrieve, or otherwise identify the user profile 160 from the database 115. The user profile 160 associated with the user 222 of the user device 110 may be stored and maintained on the database 115. The user profile 160 maintained on the database 115 may be updated using instances of the user profile 160 received from the user device 110. With the identification, the profile assessor 130 may parse the user profile 160 to extract or identify the one or more parameters 226 in the user profile 160.

Using the parameters 226, the profile assessor 130 may calculate, determine, or generate one or more measures for the user 222 associated with the user profile 160. The measures derived from the parameters 226 of the user profile 160 may be used for selecting configuration files 155 to provide to the application 165. The generation of the measures may be in accordance with a function of the parameters 226. For example, the parameters 226 may include user responses to the questions depicted in FIGS. 7A-D, and may be related to physical activity, such as whether the user 222 had performed a physical activity and how much time the user 222 had spent in performing the physical activity. In this example, the profile assessor 130 may generate measures related to a physical activity for the user 222, such as a level of physical activity.

In some embodiments, the profile assessor 130 may calculate, determine, or otherwise generate at least one measure for the user profile 160 that may be based on the user responses to the clinical assessment questionnaire, such as SCID, MINI, CAINS, and HDRS, among others. The generation of the measure may be in accordance with a function for the clinical assessments. The measure may identify a characteristic of the condition, such as a severity of the condition. When determined prior to the performance of any activity, the measure may be determined as a baseline assessment measure for the user 222. When determined after one or more activities, the measure may be determined as an assessment measure for the user 222.

In some embodiments, the profile assessor 130 may generate the measure to identify a degree of a characteristic of the condition of the user 222. For example, the characteristics of the user 222 may include, for example, a severity of a behavioral condition, a physical condition, or a psychological (or mental) condition, among others. In some embodiments, the measure may identify a likelihood that the user 222 is to perform the type of activity when prompted via the application 165. For instance, the measure may indicate a likelihood that the user 222 will perform a hobby and another measure may indicate a likelihood that the user 222 will carry out an exercise when prompted via the user interface 190 of the application 165. In some embodiments, the measure may identify a predicted efficacy of the type of activity towards achieving one or more endpoints. For example, the measure may identify how effective performance of a run would be to addressing the user's condition related to improving diet, which the user has identified as a desired endpoint.

In addition, the profile assessor 130 may store and maintain the user profile 160 including the parameters 226 on the database 115. In some embodiments, the profile assessor 130 may store and maintain the measures derived from the parameters 226 in the database 115. In some embodiments, the profile assessor 130 may include the measures in the user profile 160. In some embodiments, the profile assessor 130 may generate an association between the measures and the user profile 160 using one or more data structures. With the generation, the profile assessor 130 may store and maintain the association on the database 115. In some embodiments, the profile assessor 130 may perform the functionalities described herein in conjunction with the profile creator 170, and vice-versa.

The configuration selector 135 executing on the application configuration service 105 may select, identify, or otherwise determine one or more endpoints to address the condition of the user 222. In general, the endpoints may correspond to an outcome or measure associated with addressing the condition of the user 222. The endpoint may correspond to a mark of completion of a defined set of activities aimed at addressing the condition of the user 222. For example, the endpoint may be associated with a set number of activities over a defined window of time (e.g., 4 activities per day), and the completion of the activities by the user 222 may correspond to an attainment of the endpoint. The endpoint may also correspond to a measured improvement to the condition of the user 222. For instance, the endpoint may be associated with a perceived decrease in a sense of pain (or other metric) associated with the condition of the user 222. The endpoints may be categorized into one or more classifications (sometimes referred herein as domains). For instance, one set of endpoints may be associated with a first classification and another set of endpoints may be associated with a different second classification. Each endpoint may be associated with a set number of activities to accomplish, for example, with four activities. Each domain may be associated with a set number of endpoints, for example, with four endpoints. Each domain may be associated with a set number of parameters indicated by the user 222, for example, with three aspirations.

To determine, the configuration selector 135 may determine the endpoint for the user 222 based on the condition to be addressed for the user 222. For instance, when the condition indicated by the user 222 is dieting, the configuration selector 135 may select one or more endpoints related to dieting. In some embodiments, the configuration selector 135 may determine the endpoint based on at least one activity (or type of activity) indicated by the user 222 towards achieving the endpoint. In some embodiments, the configuration selector 135 may determine the endpoint based on the parameters 226 of the user profile 160. For example, the configuration selector 135 may determine the endpoint using the type of activity, a frequency, duration, and time as identified by the user 222. In some embodiments, the configuration selector 135 may determine the endpoint based on the measure (e.g., baseline assessment metric for clinical assessment, likelihood that the user is perform the activity, or the predicted efficacy) from the clinical assessment.

In some embodiments, the configuration selector 135 may select or identify one or more activities associated with the endpoint to be performed by the user 222 via the application 165. The identification of the activities may be based on the parameters 226 as indicated by the user 222. For instance, the configuration selector 135 may identify the activities such as Activity D, Activity E, or Activity F when the user 222 indicates the desired types of activities. In some embodiments, the configuration selector 135 may be executing on the user device 110 as part of the application 165, for example, to identify the endpoints for the user 222 of the user device 110. The identification of the endpoints may be based on the parameters 226 of the user profile 160 and the selection criterion 210 for each endpoint. As discussed, the selection criterion 210 may specify parameters 226 for which the configuration file 155 associated with the endpoint is to be selected.

The configuration selector 135 may identify or select one or more configuration files 155 from the overall set of configuration files 155 to provide to the application 165 on the user device 110. Based on the endpoint (or activities towards achieving the endpoint), the configuration selector 135 may select the associated configuration file 155 for provision to the application 165. In some embodiments, the configuration selector 135 may select multiple configuration files 155 for at least one endpoint. For example, when the determined endpoint is for addressing smoking cessation, the configuration selector 135 may identify a set of configuration files 155 marked as addressing smoking cessation in the selection criterion 210. Conversely, for each routine identified as not to be included, the configuration selector 135 may refrain from selecting the associated configuration file 155 for provision to the application 165.

To select, the configuration selector 135 may identify the selection criterion 210 for each configuration files 155 from the database 115. In some embodiments, the configuration selector 135 may parse each configuration file 155 to extract or identify the selection criterion 210 for the corresponding endpoint. In some embodiments, the configuration selector 135 may identify the selection criterion 210 for the specified one or more activities. With the identification, the configuration selector 135 may compare the parameters 226 with the selection criterion 210 for the endpoint. When the parameters 226 match with the parameters specified by the selection criterion 210, the configuration selector 135 may select the configuration file 155. Otherwise, when the parameters 226 do not match with the parameters specified by the selection criterion 210, the configuration selector 135 may refrain from selecting the configuration file 155.

In some embodiments, the routine selector 315 may compare the measures derived from the parameters 226 with the selection criterion 210 for the routine to determine whether to select the given configuration file 155. When the determined measures satisfy (e.g., greater than or equal to, or within) the measures specified by the selection criterion 210, the routine selector 315 may select the configuration file 155 for provision. Otherwise, when the parameters 226 do not satisfy (e.g., less than or outside) the parameters specified by the selection criterion 210, the routine selector 315 may refrain from selecting the corresponding configuration file 155 for provision.

With the selection, the configuration selector 135 may relay, convey, or otherwise provide an identification of the selected configuration files 155 (or by extension, routines) to the profile assessor 130 to set or update the user profile 160. Stored in the database 115, the user profile 160 may be used to keep track of the routines and configuration files 155 provided to the user 222 and the progress of the user 222 in each routine using the state 204 and the level 208 of the routine logic 202. When storing the user profile 160 as part of the initial selection of the configuration file 155, the profile assessor 130 may identify the state 204 and the level 208 for each selected routine as in the initial state (e.g., the state 204A) and initial level (e.g., the level 208A) respectively. The profile assessor 130 may store and maintain the initial state 204 and the initial level 208 for each selected configuration file 155 in the user profile 160 on the database 115.

The configuration packager 140 executing on the application configuration service 105 may produce, output, or otherwise generate at least one package 228 using the selected configuration files 155. In some embodiments, the configuration packager 140 may be executed on the user device 110, for example, to generate the package 228 to be loaded by the application 165. The package 228 may include instructions for configuring, defining, or otherwise specifying various functionalities to be performed on the application 165. In general, the instructions in the package 228 may be in machine-readable code. The instructions for the package 228 may also define the routine logic 202, including the set of states, and the transitions 206, and the levels 208. In addition, the instructions for the package 228 may also define the user interface elements 195 for the outputs in the states 204 in the routine logic 202. Because the package 228 is generated separately from the application 165, which packages 228 the application 165 is to include may be readily interchanged, based on the condition of the user to be addressed. In generating, the configuration packager 140 may create a separate file in which to store the specifications for the package 228. The configuration packager 140 may parse the one or more configuration files 155 to read or identify the instructions in the original format.

Upon identification of the configuration file 155, the configuration packager 140 may generate or determine an equivalent instruction in an executable format for inclusion into the application 165. In some embodiments, the configuration packager 140 may compile the configuration file 155 to generate instructions in a lower-level language. When compiled, the instructions for the package 228 may be in a lower-level language, such as byte code, assembly, object code, or machine code, among others. In some embodiments, the configuration packager 140 may transpile the configuration file 155 to generate instructions in an intermediary-format to be added to the application 165. For example, the instructions may be in a similar-level language as the original of the configuration file 155, such as JavaScript or Typescript, among others. Upon generation, the configuration packager 140 may write the equivalent instruction into the file for the package 228, and may repeat until the end of the configuration file 155.

With the generation, the configuration packager 140 may provide the instructions for the package 228 to add or include to the application 165. In some embodiments, the configuration packager 140 may insert or inject the package 228 into the application 165, prior to provision to the user device 110. For example, the configuration packager 140 may inject the package 228 into the application 165 that already includes the other components, such as the behavior manager 175, the layout handler 180, and the event bus 185, among others. The configuration packager 140 may provide the application 165 containing the injected package 228 to the user device 110 via a digital distribution platform (e.g., application market or store). The user device 110 may request to download or retrieve the application 165 from the application configuration service 105 (or the digital distribution platform) for installation. Once received, the user device 110 may unpack and install the application 165 including the package 228.

The configuration packager 140 may send, transmit, or otherwise provide the instructions for the package 228 to add or include the application 165 that is installed on the user device 110. For example, the user device 110 may have previously installed the application 165 received from the application configuration service 105 (e.g., via the digital distribution platform). In some embodiments, the user device 110 may subsequently request for an update of the configuration of the application 165. In some embodiments, the configuration packager 140 may identify or determine that an update is to be provided to the application 165 through the configuration file 155. For instance, a system administrator of the application configuration service 1605 may direct that instances of the application 165 are to be updated. With the identification of the update, the configuration packager 140 in turn may provide the instructions for the package 228, without providing the other components of the application 165. Upon receipt, the user device 110 (or the application 165 itself) may update the already installed application 165 to include the package 228. In some embodiments, the received instructions for the package 228 may be in the intermediary format, and the application 165 may further compile the instructions to generate the lower-level format to run on the user device 110.

Figure 2C:
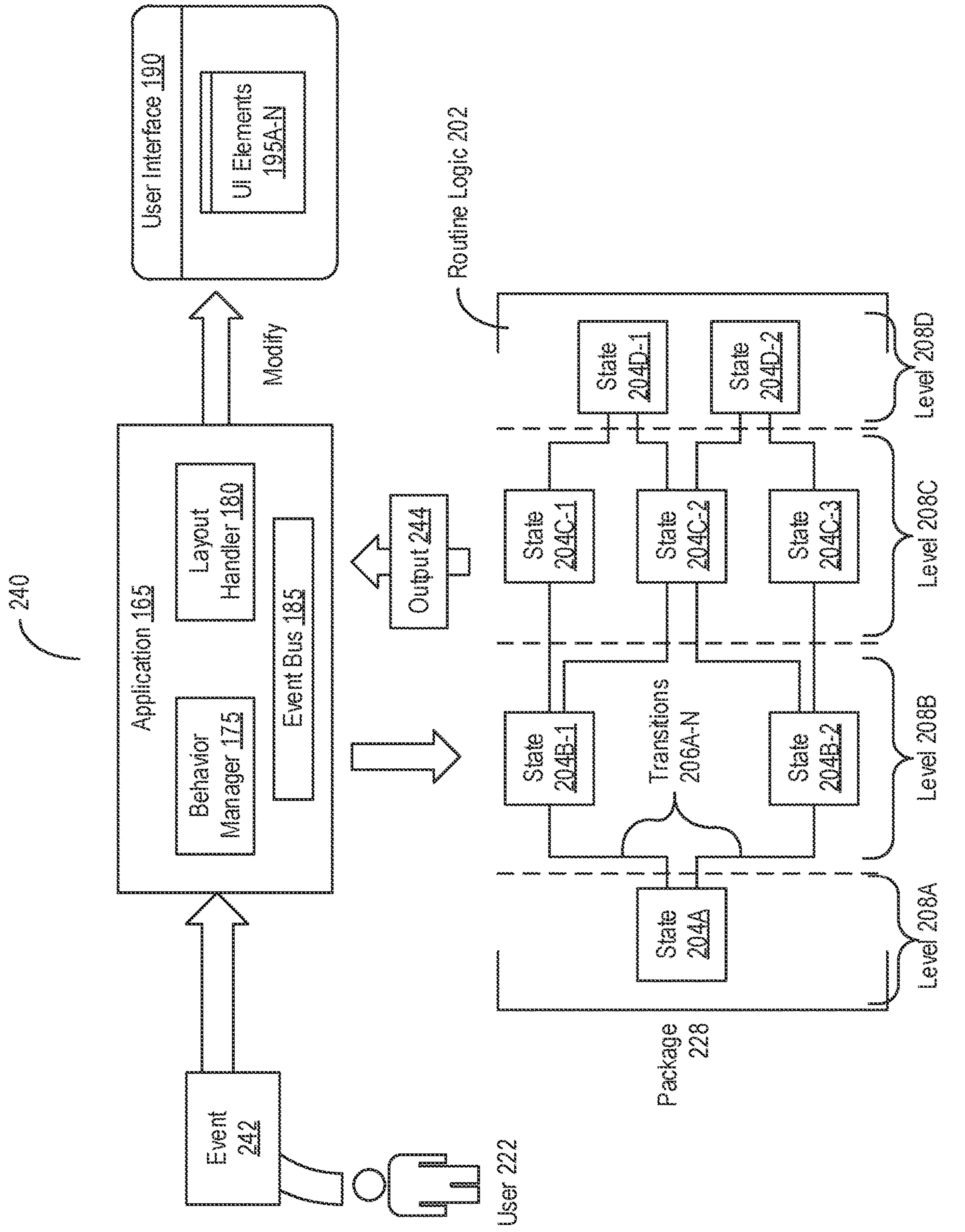
FIG. 2C depicts a block diagram of a process for handling configuration packages in the system for selecting configuration files, in accordance with an illustrative embodiment.

Referring now to FIG. 2C, depicted is a block diagram of a process 240 for handling configuration packages in the system 100 for selecting configuration files. The process 240 may include or correspond to the operations performed in the system 100 upon loading and running the routine logic 202 as defined in the package 228. Under the process 240, the application 165 (or an application services of the application 165) may perform initialization operations, such as starting the execution of the behavior manager 175, the layout handler 180, the event bus 185, and the user interface 190, among others. The application 165 may run various logic and operations defined for the application 165 outside of the package 228 received from the application configuration service 105. The application 165 may retrieve, identify or otherwise receive the package 228 from the application configuration service 105.

The behavior manager 175 of the application 165 executing on the user device 110 may parse the package 228 to read, load, and run the routine logic 202. As described above, the routine logic 202 may correspond to a set of activities to be performed, recorded, and logged by the user 222 via the application 165 on the user device 110. In some embodiments, the behavior manager 175 may parse multiple packages 228 to run multiple, corresponding routing logic 202. For each routine logic 202, the behavior manager 175 may keep track of the current state 204 of the routine logic 202. In some embodiments, the behavior manager 175 may use or maintain an identifier for the current state 204 for each routine logic 202 to keep track. In addition, the behavior manager 175 may keep track of the current level 208 for the user 222 as defined in the routine logic 202. In some embodiments, the behavior manager 175 may identify the current level 208 from the current state 204 at which the routine logic 202 is in. Upon initialization, the current state 204 of the routine logic 202 may correspond to the starting state 204 (e.g., state 204A in the depicted example). The current level 208 may correspond to the first level 208 (e.g., the level 208A in the depicted example).

In conjunction, the behavior manager 175 may monitor or listen for at least one event 242 on one or more of the user interface elements 195 in the user interface 190 via the event bus 185. The event 242 may correspond to activity performed by a user 222 of the application 165. For example, the user interface 190 may present a prompt for the user 222 to conduct Exercise B, and the user 222 may indicate the completion of the exercise via interaction with one of the user interface elements 195 on the user interface 190. The event 242 may thus correspond to a completion of the activity as specified by the state 204 in the routine logic 202.

In some embodiments, the behavior manager 175 may monitor or listen for the event 242 from another process of the application 165 or user device 110. The event 242 in this case may correspond to an occurrence of an action by a process of the application 165 or the user device 110 that was not triggered by an interaction from the user 222. For example, the behavior manager 175 may receive time elapsed from the presentation of the prompt to conduct the activity via a system timer on the user device 110. The behavior manager 175 may compare the elapsed time with the timespan specified by the state 204 within which to complete the activity. The behavior manager 175 may identify the exceeding of the specified time as the event 242.

In some embodiments, the behavior manager 175 may prompt the user 222 to select or identify whether to perform the activity presented in the prompt. For example, after receiving their activity prompt, the user 222 may select to either "do it now" or "do it later" to increase the likelihood of completion through multiple paths. The former option may allow the user 222 to indicate the user 222 is behaviorally activated. This may be a major benefit by being able to capture users when they are motivated, as compared to a different, more fixed setting that only permits the latter option. The latter option may reinforce the behavior to plan for an activity, select a time, and receive a reminder, and do the activity with the application 165 at a specified later time. When the identification is to perform the activity at a later time, the behavior manager 175 may store the indication, and may re-present the prompt for the activity at the specified time. Otherwise, when the indication is to perform the activity, the behavior manager 175 may proceed with further processing to load the routine logic 202 of the package 228.

Based on the detection of the event 242, the behavior manager 175 may determine or select at least one routine logic 202 in the corresponding package 228 to invoke. In some embodiments, the behavior manager 175 may convey or pass the detected event 242 to the package 228 via the event bus 185. The event bus 185 may correspond to an interface between the package 228 and the various components of the application 165, such as the behavior manager 175 and the layout handler 180, among others. By passing, the behavior manager 175 may check the detected event 242 against the event specified by the transitions 206 for the current state 204. As discussed above, the behavior manager 175 may keep track of the current state 204 and the current level 208 of each routine logic 202 in the respective package 228. In some embodiments, the behavior manager 175 may detect or receive the result of the checking of the detected event 242 via the event bus 185.

From the routine logic 202, the behavior manager 175 may identify the specified event for each transition 206 associated with the current state 204 to check against the detected event 242. When the detected event 242 does not correspond to the specification in any of the transitions 206 of the current state 204, the behavior manager 175 may maintain the routine logic 202 at the current state 204 and the current level 208. In some embodiments, the behavior manager 175 may also refrain from invoking the routine logic 202. The maintenance of the routine logic 202 at the current state 204 may correspond to the user 222 not having completed an activity of the routine set out for the routine logic 202 for any of the transitions 206 associated with the current state 204. The behavior manager 175 may continue to check the detected event 242 against the specifications of the routine logic 202 in other packages 228.

Conversely, when the detected event 242 corresponds to the specification in one of the transitions 206 of the current state 204, the behavior manager 175 may select the routine logic 202 to invoke. By invoking, the behavior manager 175 may update the current state 204 and the current level 208 of the routine logic 202 to the next state 204 in accordance with the transition 206. The updating of the routine logic 202 from the current state 204 to the next state 204 may correspond to the user 222 having completed (successfully or unsuccessfully) an activity of the routine set out for the routine logic 202 as identified for at least one of the transitions 206 associated with the current state 204. For example, the current state 204 may be updated from the initial state 204A to the state 204B-1 upon successful completion as specified by the respective transition 206. In contrast, the current state 204 may be transitioned from the initial state 204A to the state 204B-2, upon failure of completion as defined by the respective transition 206.

In addition, from invoking the routine logic 202 of the package 280, the behavior manager 175 may retrieve or identify an output 244 identified by the next state 204 of the routine logic 202. The output 244 may be produced or generated by the state 204 as specified in the routine logic 202 upon invocation. The output 244, as discussed above, may identify the user interface elements 195 to be presented via the user interface 190 of the application 165. In some embodiments, the output 244 may specify modifications to be applied to the user interface elements 195 of the user interface 190. The behavior manager 175 may convey or pass the output 244 to the layout handler 180 via the event bus 185.

Figure 2D:
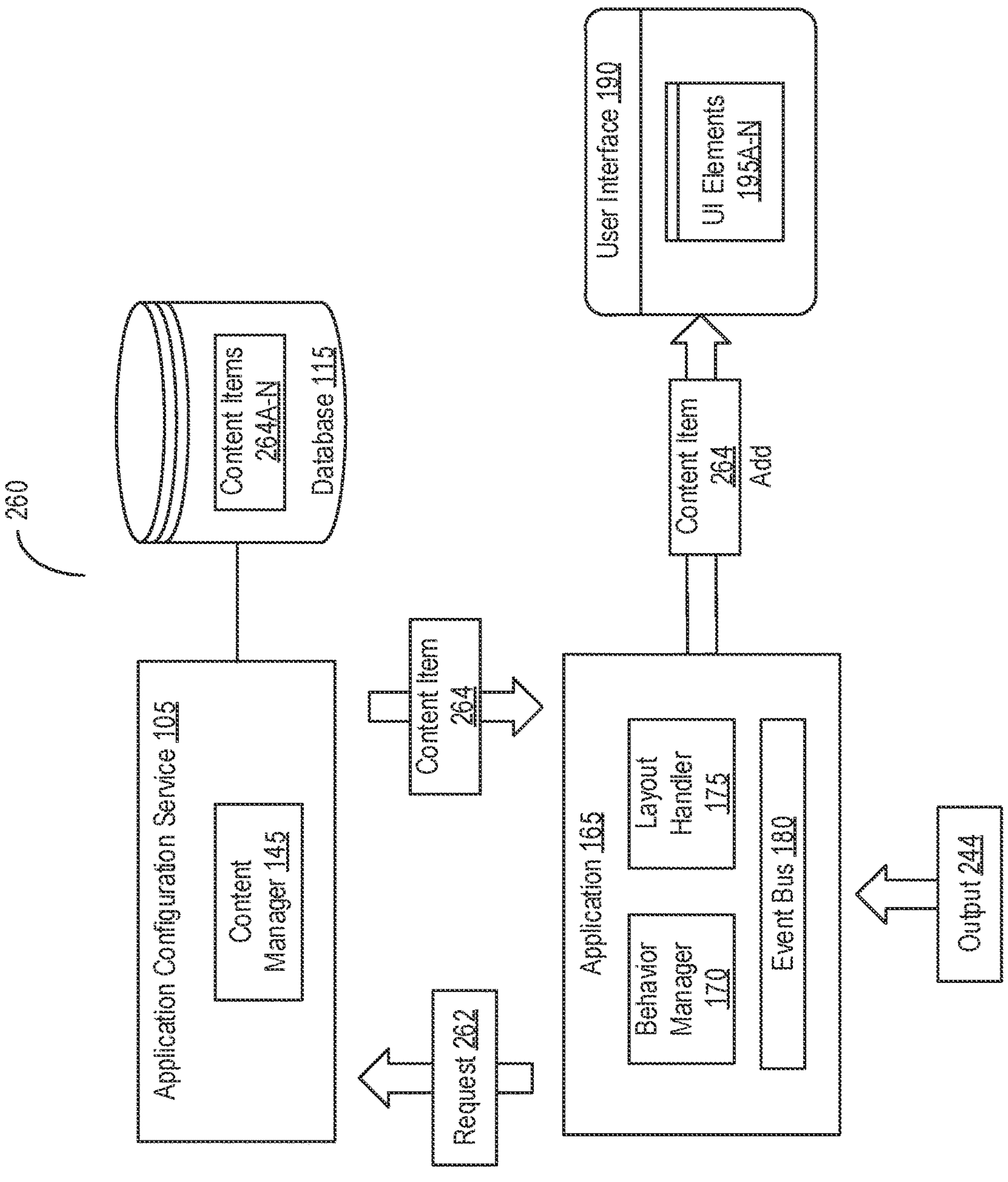
FIG. 2D depicts a block diagram of a process for modifying user interfaces in the system for selecting configuration files, in accordance with an illustrative embodiment.

Referring now to FIG. 2D, depicted is a block diagram of a process 260 for modifying user interfaces in the system 100 for selecting configuration files. The process 260 may include or correspond to the operations of the application configuration service 105 and application 165 upon invocation of one of the routine logic 202 defined in the packages 228. Under the process 260, the layout handler 180 of the application 165 executing on the user device 110 may update, change, or otherwise modify the user interface elements 195 of the user interface 190 in accordance with the output 244. By setting the user interface 190, the layout handler 180 may associate or bind the states 204 (and the level 208) in the routine logic 202 of the package 228 to the user interface elements 195 of the user interface 190. In some embodiments, the layout handler 180 in conjunction with the behavior manager 175 may maintain the association or binding of the states 204 (and the level 208) of the routine logic 202 and the user interface elements 195 of the user interface 190. For example, the layout handler 180 may keep track of a relationship between the state 204 (and the level 208) of the most recently invoked routine logic 202 and the user interface elements 195 rendered or presented via the user interface 190.

In modifying, the layout handler 180 may determine whether to send a request 262 for content to the application configuration service 105 or to another remote service (e.g., associated with the developer of configuration file 155). In some embodiments, the layout handler 180 may be executed on the user device 110, for example, to identify content to be presented through the user interface 190. The output 244 may rely on at least one content item 264A-N (hereinafter generally referred to as content item 264). The content item 264 may be stored and maintained on a database (e.g., the database 115 as depicted), and may include images, videos, and other objects to be provided during the runtime of the application 165. If the output 244 does not specify for the retrieval of the content item 264, the layout handler 180 may refrain from transmitting the request 262 for content to the application configuration service 105. The layout handler 180 may also continue to modify the user interface elements 195 of the user interface 190 in accordance with the output 244. On the other hand, if the output 244 specifies for the retrieval of the content, the layout handler 180 may determine to send the request 262 for content to the application configuration service 105. The layout handler 180 may generate the request 262 for content to include at least one identifier referencing the content item 264 to be retrieved from the application configuration service 105. The identifiers may be specified by the output 244 from the now-current state 204 of the routine logic 202.

The content manager 145 executing on the application configuration service 105 may retrieve, identify, or otherwise receive the request 262 for content from the user device 110. In some embodiments, the content manager 145 may reside on a remote service separate from the application configuration service 105. The content manager 145 may parse the request 262 to identify the content item 264 to be provided to the user device 110 for presentation on the user interface 190. In some embodiments, the content manager 145 may use the identifier in the request 262 to access the database 115 to retrieve, fetch, or identify the content item 264 referenced by the identifier. The content item 264 may be information in a visual or audio medium, and may include an image, a video, an audio, or any other object to be presented on the user interface 190. For example, the content item 264 may include an audio to be played in conjunction with Exercise C for the endpoint associated with the invoked routine logic 202. With the identification, the content manager 145 may send, return, or otherwise provide the content item 264 to the user device 110.

The layout handler 180 may in turn retrieve, identify, or receive the content item 264 from the application configuration service 105 (or the remote service). Upon receipt, the layout handler 180 may insert, add, or otherwise include the content item 264 in the user interface 190. The layout handler 180 may include the content item 264 in one or more of the user interface elements 195 for presentation as specified in the output 244 from the routine logic 202. Concurrently, the layout handler 180 may modify the user interface elements 195 of the user interface 190 in accordance with the output 244. For example, the layout handler 180 may instantiate the user interface elements 195, set the color and other visual characteristics of the individual user interface elements 195 themselves, set the font and size of the text in the individual user interface elements 195, and assign the placement of the user interface elements 195 within the display of the user device 110.

In some embodiments, the layout handler 180 may generate or determine a render instructions using the output 244 specified by the routine logic 202. The output 244 may identify a set of instructions (e.g., in an original or lower-level format) corresponding to the respective user interface elements 195 to be included in the user interface 190. The render instructions may be in the form of a display list or render tree. Upon identification, the layout handler 180 may parse the instructions in the output 244 corresponding to the set of user interface elements 195. For each instruction, the layout handler 180 may generate an equivalent entry (e.g., a render tree node) to include in the render instructions. With the generation, the layout handler 180 may present the user interface elements 195 for the user interface 190 in accordance with the render instructions.

Examples of the content items 264 to be presented as user interface elements 195 on the user interface 190 are depicted in FIGS. 8A-L (level 1 for trying new hobbies, with selection of old hobbies), 9A-L (level 2 for trying new hobbies), 10A-J (level 3 for trying new hobbies), 11A-G (level 4 for trying new hobbies), 12A-D (level 1 for building a habit), 13A-K (level 2 for building a habit), 14A-J (level 2 for building a habit), 15A-J (level 3 for trying a new habit), and 16A-J (level 4 for a new habit). Similar to the questionnaire prompt 224, the content items 264 may also include prompts for questions to be responded by the user 222. Each question in depicted example may correspond to at least one content item 264, and may be associated with a transition 206 from one state 204 to another state 204. The user 222 may be presented with the depicted prompts upon interacting with the buttons, triggering the transitions 206 from one state 204 to another state 204.

Figure 2E:
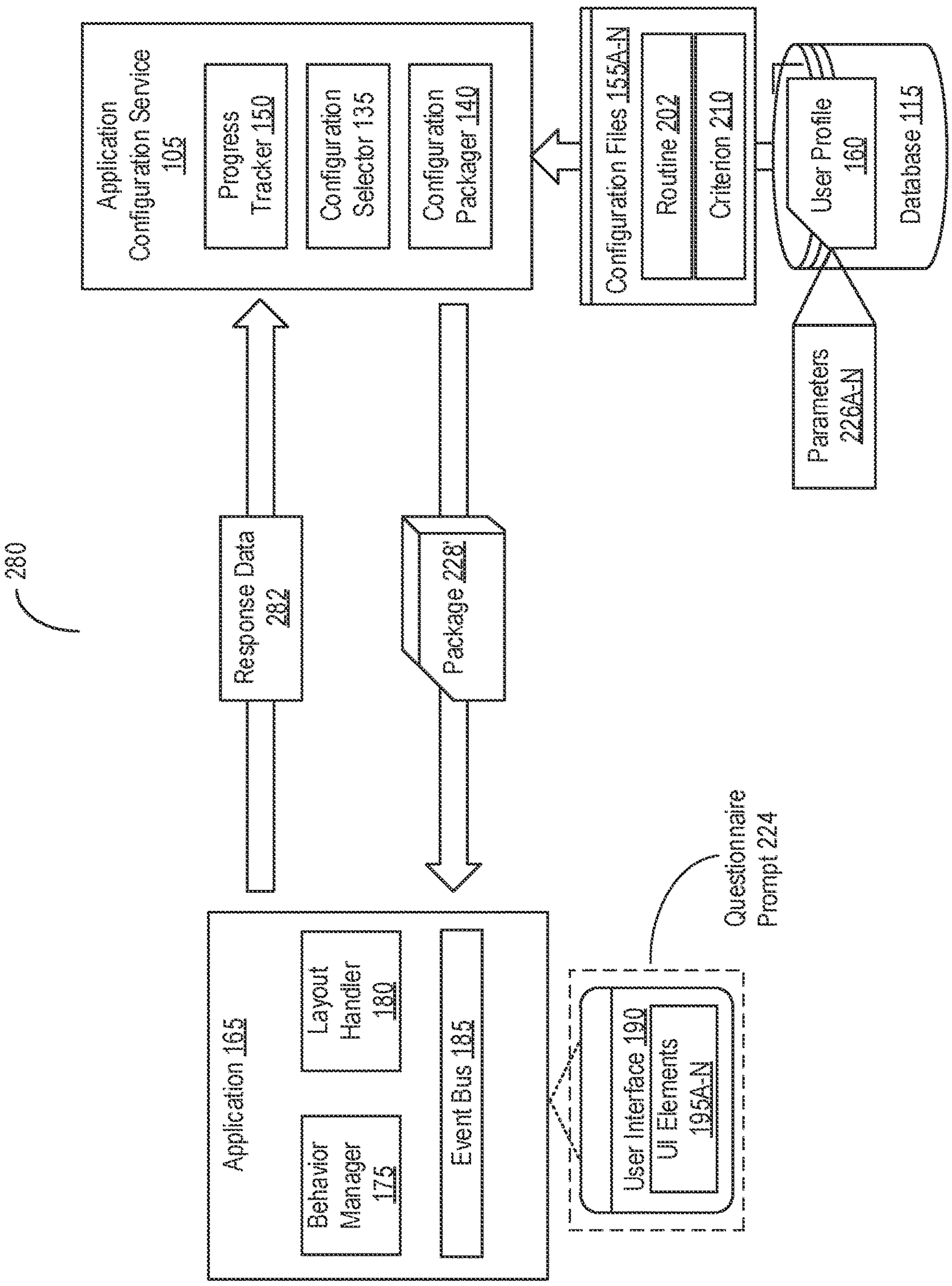
FIG. 2E depicts a block diagram of a process for assessing response data to provide configuration files in the system for selecting configuration files, in accordance with an illustrative embodiment.

Referring now to FIG. 2E, depicted is a block diagram of a process for assessing response data to provide configuration files in the system 100 for selecting configuration files. The process 280 may include or correspond to operations in the system 100 to evaluate responses and provide new packages. Under the process 280, the behavior manager 175 may send, transmit, or provide at least one response data 282 (sometimes referred to as a record entry) to the application configuration service 105. Upon detection of one or more events 242, the behavior manager 175 may write or generate the response data 282. The response data 282 may identify or include various events 242 in accordance with the set of activities as defined in the package 228 provided to the user device 110. For example, the information included in the response data 282 may include or identify: the current state 204 and current level 208 of each routine logic 202; an update to the state 204 or the level 208 in the routine logic 202; an indication of completion or failure to complete the routine associated with a routine logic 202; the detected events 242, a timestamp at which each event 242 is detected, an identifier for the user 222, and an identifier for the user device 110, among others. With the generation, the behavior manager 175 may send the response data 282 to the application configuration service 105.

In some embodiments, the behavior manager 175 may call or invoke the profile creator 170 to aggregate, collect, or otherwise receive additional responses from the user 222 via the questionnaire prompt 224. The prompt 224 may be presented at a defined time, such as at the beginning of a day, an end of a day, once every 4-6 hours, once every week, or once a month, among others. For example, the user 222 may interact with a user interface element 195 to present the prompt 224 to present the set of questions. As described previously, the questions may inquire the user 222 to indicate a desired endpoint to achieve, a condition to be addressed, preferences for performance of activities or routines, such as type of routine, frequency, duration, day of week, and time of day, among others. The questions may also be part of a clinical assessment interview as discussed above. The behavior manager 175 may receive the responses by the user 222 to the set of questions via the prompt 224 in a similar manner as discussed above. Upon receipt, the behavior manager 175 may include the responses from the user 222 into the response data 282.

In some embodiments, the behavior manager 175 may determine or identify at least one state of the user 222 (e.g., a mood, emotional, behavioral, or physiological state) from the responses from the user 222 via the questionnaire prompt 224. Examples of the questionnaire prompt 224 for mood are depicted in FIGS. 17A-G. The mood check-in as depicted in the example may support the user 222 to increase likelihood of performing the activity (e.g., when prompted or at a later time). The check-in may also allow for the user 222 to build trust in performing the activities through the application 165 to meet the user 222 at their emotional state and towards achieving the endpoint. The prompts 224 in the depicted example may allow the user 222 to indicate the user's mood (sometimes referred herein as emotional state), such as happiness, sadness, anger, fear, disgust, surprise, or excitement, among others. The response may be used to select configuration files 155 to provide targeted mitigations. Other states may include behavioral state (e.g., at rest, eating, working, studying, at leisure, interacting, playing, or exploring) or physiological state (e.g., resting, active, stressed, or intense), among others. The behavior manager 175 may invoke the profile creator 170 to present the questionnaire prompt 224 via the user interface elements 195 of the user interface 190 to prompt the user 222 to indicate the state. The questionnaire prompt 224 may be presented to the user 222 at a defined time (e.g., once every 4-6 hours, once a day in the evening, or once a week). Through the questionnaire prompt 224, the behavior manager 175 may receive the response indicating the state of the user 222. With receipt, the behavior manager 175 may include the responses from the user 222 into the response data 282.

Figure 18A:
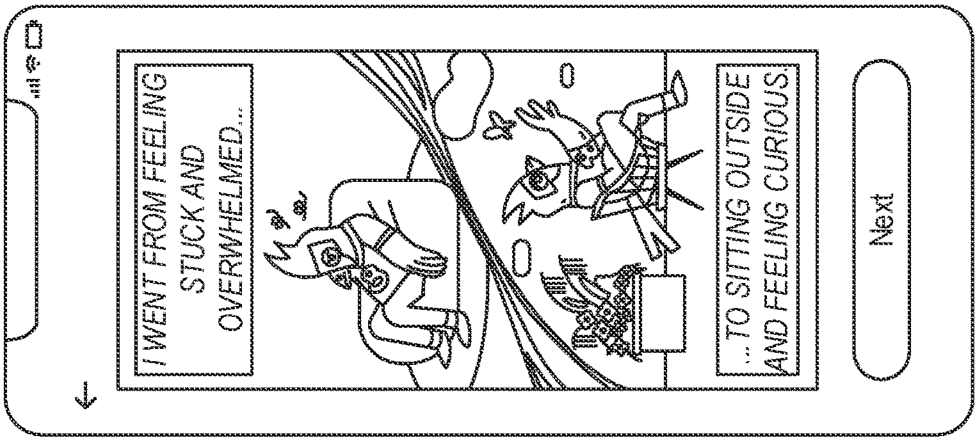
FIGS. 18A-C each depict examples of screenshots of prompts for user to input personal values subsequent, in accordance with an illustrative embodiment.
Figure 18B:
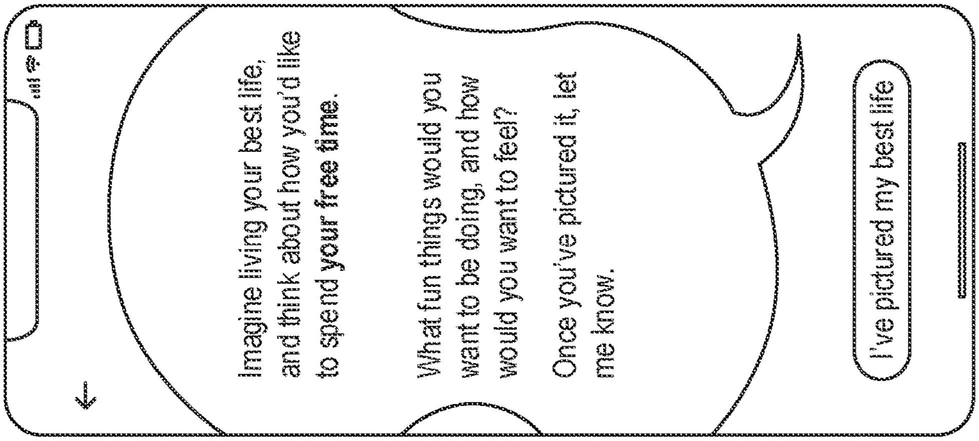
Figure 18C:
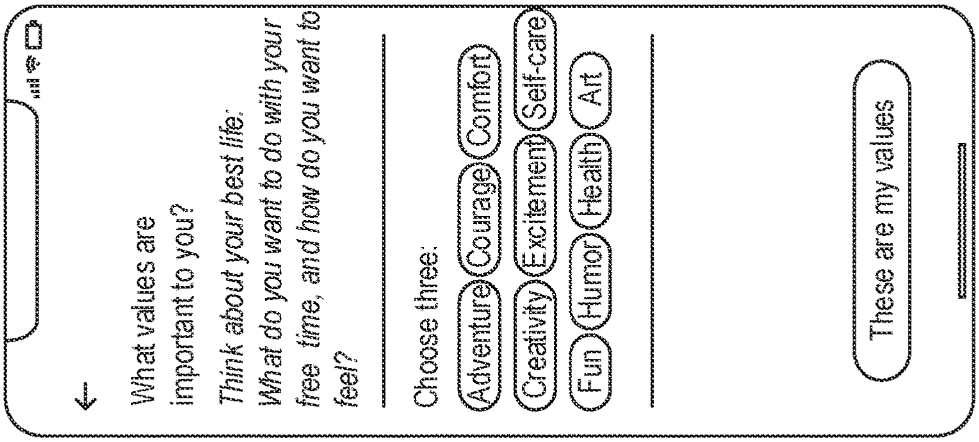
Figure 19A:
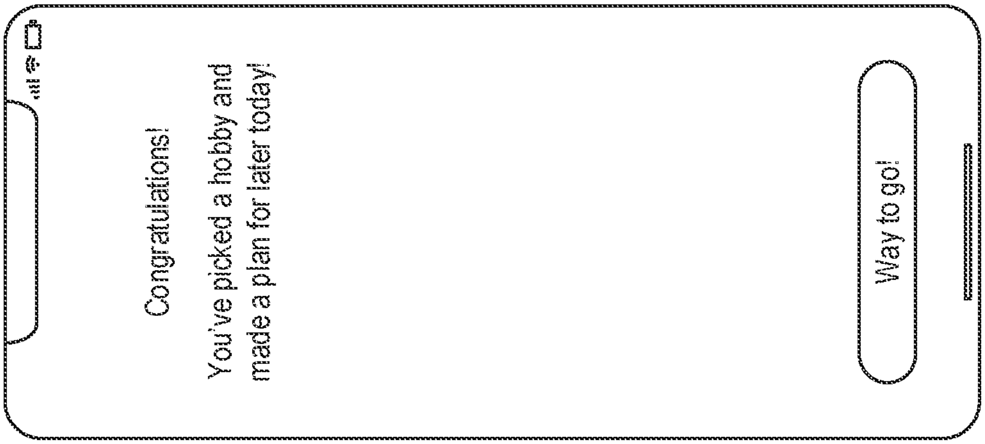
FIGS. 19A-D each depict examples of screenshots of prompts for presenting pre-activity and post-activity assessments, in accordance with an illustrative embodiment.
Figure 19B:
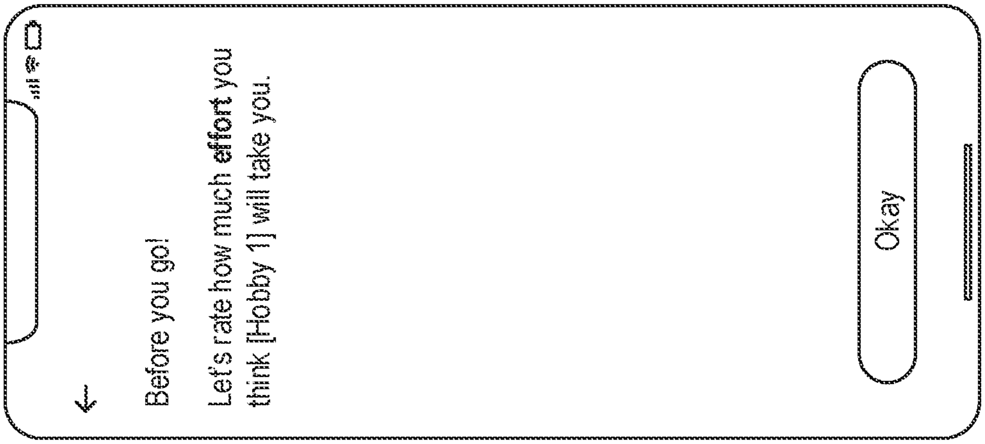
Figure 19C:
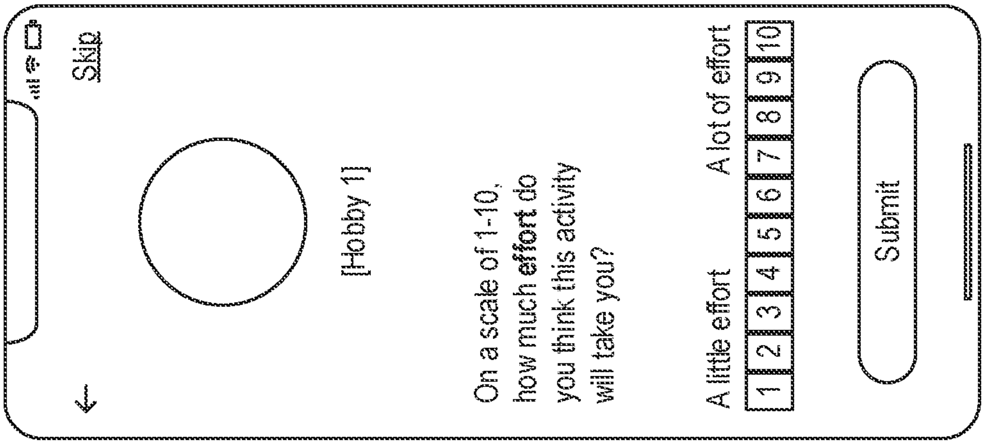
Figure 19D:
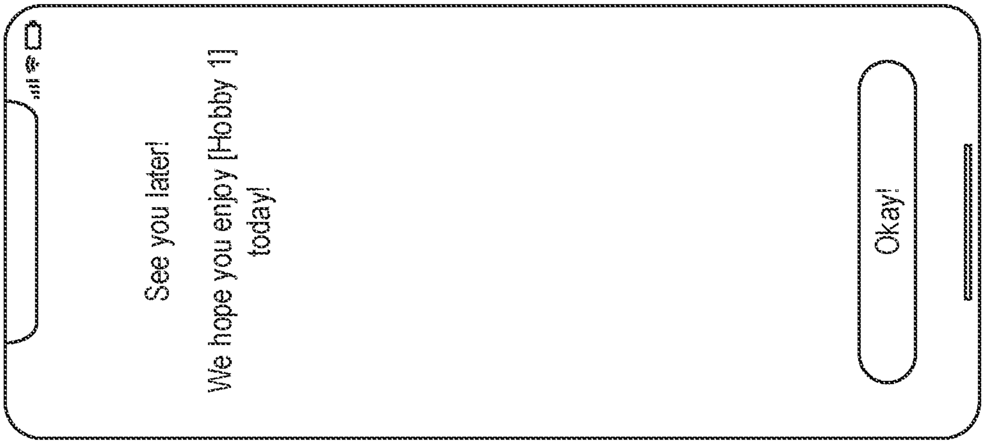

In some embodiments, the behavior manager 175 may determine or identify one or more personal values of the user 222 from the responses of the user 222 in response to the prompt 224. Examples of the questionnaire prompt 224 for personal values are depicted in FIGS. 18A-C. In the depicted examples, the interface in FIG. 18A may provide a scenario to the user 222 to consider, the interface in FIG. 18B may provide the user 222 an opportunity to explore values or biases for a goal or endpoint in mind, and the prompt in FIG. 18C may allow the user 222 to input one or more personal values to resurface throughout the session. The personal values may identify characteristics of activities that the user 222 desires to perform or endpoints that the user 222 identifies as objectives in performing the activities. The questionnaire prompt 224 may be presented to the user 222 at a defined time (e.g., check-in once every 4-6 hours, once a day in the evening, or once a week). Through the questionnaire prompt 224, the behavior manager 175 may receive the response indicating the one or more personal values. With receipt, the behavior manager 175 may include the responses from the user 222 into the response data 282.

In some embodiments, while running the routine logic 202 of the configuration file 155, the behavior manager 175 may determine, obtain, or otherwise identify a rating associated with the activity prior to performance. To identify, the behavior manager 175 may present the prompt 224 to indicate the rating associated with the activity prior to the performance of the activity. In addition, the behavior manager 175 may determine, obtain, or otherwise identify a rating associated with the activity subsequent to the performance via the application 165. To identify, the behavior manager 175 may present the prompt 224 to indicate the rating associated with the activity subsequent to the performance of the activity. The ratings may be obtained from the responses of the user 222 in response to one or more prompts 224 for indicating the ratings. The rating prior to performance may indicate a self-assessed value for expectation by the user 222 at addressing the condition or toward achieving the endpoint by performing the activity identified in the prompt 224. The rating subsequent to performance may identify a self-assessed value for an experience by the user 222 at addressing the condition or toward achieving the endpoint subsequent to performing the activity identified in the prompt 224.

Regarding the ratings, the application 165 through the configuration file 155 may provide lesson content explaining the connection between thoughts, emotions, and behavior to inform the user 222 about the premise of cognitive restructuring and how the activities address the condition. With the configuration files 155, the application 165 may provide one or more interactive activities to help the user 222 understand thought patterns that contribute to defeatist beliefs associated with negative symptoms.

For example, in an orientation Phase, after the user 222 is introduced to the pre and post-activity survey concept, the behavior manager 175 surveys the user a given number of times (e.g., 4 times). Before the user 222 starts an activity, the behavior manager 175 may prompt the user 222 with an anticipatory question regarding their activity to select from a scale of 1 to 10. After the user 222 completes an activity, the behavior manager 175 may prompt the user 222 a reflection question regarding their activity to select from a scale of 1 to 10. In the active phase, the behavior manager 175 may prompt the user 222 before and after each activity with the survey. Before the user 222 starts an activity, the behavior manager 175 may prompt the user 222 with an anticipatory question regarding their activity to select from a scale of 1 to 10. After the user 222 completes an activity, the behavior manager 222 may prompt the user 222 with a reflection question regarding their activity to select from a scale of 1 to 10.

Examples of the questionnaire prompt 224 for self-assessed ratings for pre and post-activity are depicted in FIGS. 19A-D. In the depicted example, the prompts may encourage users to practice noticing their expectations with each activity. The question in the prompt 224 may be a pre/post activity question and the response data may be used to reflect back a user's own indications to combat defeatist beliefs and show growth. These self-assessments by the user 222 may be used to reflect shifts in perception. Showing improvements may be a powerful driver of trust, leading to a change in user perception that may motivate users 222 to more closely adhere to the digital therapeutic provided through the configuration files 255. After performing the activity, the user 222 may be prompted to reflect on the experience from performing the activity. The user 222 may be shown pre and post activity responses to encourage adherence and continued performance of the activities presented via the application 165. Through the questionnaire prompt 224, the behavior manager 175 may receive the response indicating the ratings. With receipt, the behavior manager 175 may include the responses from the user 222 into the response data 282.

The progress tracker 150 executing on the application configuration service 105 may change, modify, or otherwise update the user profile 160 maintained on the database 115, using the response data 282. As discussed previously, the user profile 160 maintained on the database 115 may be used to keep track of the progress of the user 222 with each routine provided via the package 228. The progress tracker 150 may retrieve, identify, or otherwise receive the response data 282 from the user device 110. Upon receipt, the progress tracker 150 may parse the response data 282 to extract or identify the information included therein. In some embodiments, the progress tracker 150 may store and maintain the response data 282 (e.g., including the indication of the state of the user 222, one or more personal values, or ratings) on the database 115. The progress tracker 150 may use a log record associated with the user profile 160 or the user 222 to store the response data 282 on the database 115. The log record may be a data structure associated with the user profile 160.

Based on the information parsed from the response data 282, the progress tracker 150 may set, update, or otherwise modify the user profile 160. Using the identifier for the user 222 from the response data 282, the progress tracker 150 may identify the user profile 160 associated with the user 222. From the user profile 160, the progress tracker 150 may identify a currently recorded level 208 of the user 222. The level 208 may correspond to a stage or a progression towards achieving a given endpoint, a set of activities, or addressing of the condition, among others. For each configuration file 155 selected for the user 222, the user profile 160 may identify the current state 204 and the current level 208 in the routine logic 202.

With the identification, the progress tracker 150 may determine whether there is a transition from the current level 208 to a next level 208 based on the response data 282. From the response data 282, the progress tracker 150 may extract or identify the level 208 of the user 222. In some embodiments, the progress tracker 150 may determine whether to transition the level 208 for the user 222 towards achieving the endpoint. When the user 222 has accomplished the endpoint or the activity, the level 208 indicated in the response data 282 may be higher than the level 208 currently identified in the user profile 160. When the user 222 has not accomplished the endpoint or the activity, the level 208 indicated in the response data 282 may be the same or lower than the level 208 currently identified in the user profile 160. In some embodiments, the progress tracker 150 may determine the new state 204 and the level 208 in accordance with the routine logic 202 of the configuration file 155 selected for the user 222 using the one or more interactions as identified in the response data 282. The new level 208 may be towards achieving a different endpoint than the previous level 208 as indicated in the user profile 160.

The progress tracker 150 may compare the level 208 from the user profile 160 with the level 208 identified in the response data 282 to determine whether there is a transition. If the levels are not different, the progress tracker 150 may determine that there is no transition from the current level 208 for the user 222. If the levels are different, the progress tracker 150 may determine that there is a transition between the current level 208 to the next level 208. The progress tracker 150 may set the state 204 and the level 208 in the user profile 160 to the state 204 and the level 208 respectively as identified in the response data 282. In some embodiments, the progress tracker 150 may determine or identify the transition as to a higher or lower level based on the identified levels 208. When the current level 208 is lower than the level 208 identified from the response data 282, the progress tracker 150 may determine the transition as to a higher level. Conversely, when the current level 208 is higher than the indicated level 208, the progress tracker 150 may determine the transition as to a lower level.

In addition, the progress tracker 150 may set, update, or otherwise modify the parameters 226 in the user profile 160 using the information from the response data 282. As discussed previously, the parameters 226 may identify: the endpoint to be achieved and the condition of the user 222 to be addressed; the state of the user 222; a type of routine; a frequency; duration; and time (e.g., day of week or time of day) for the routine, among others. In some embodiments, the progress tracker 150 may adjust, set, or change the frequency and duration based on the indication of success or failure of the routine selected for the user 222 or update in the state 204 or the level 208. For example, the progress tracker 150 may increase the frequency or duration for the routine, when the response data 282 indicates successful completion of the routine. Conversely, the progress tracker 150 may decrease the frequency or duration for the routine, when the response data 282 indicates failure to complete the routine.

In some embodiments, the progress tracker 150 may identify or determine at least one progression metric with respect to the personal values based on the response data 282. The response data 282 may identify the performance of the activity towards achieving the endpoint, such as the one or more interactions with the content items presented via the user interface 190 of the application 165. The progression metric may identify or correspond to a measure of improvement or degradation with respect to satisfying the personal values from performing the activities specified by the configuration file 155. For instance, for a personal value of excitement, the progress tracker 150 may determine a relatively higher progression metric when the response data 228 indicates that the user is satisfied with the activities performed. With the determination, the progress tracker 150 may transmit, send, or otherwise provide a connection between the progression metrics and the personal values for presentation via the user interface 190 of the application 165. For example, the connection may be presented as part of the prompt 224 or on the user interface 190 subsequent to the presentation of the prompt 224. In some embodiments, the progress tracker 150 may provide the progression metrics as part of the subsequent package to be provided to the application 165. The progress metrics may be presented to the user 222 to encourage reflection and drive perception of progress.

In some embodiments, the progress tracker 150 may compare the ratings obtained prior to the performance of the activity and subsequent to the performance of the activity as identified in the response data 282. Based on the comparison, the progress tracker 150 may calculate, generate, or otherwise determine a metric identifying a difference between the two ratings. With the determination, the progress tracker 150 may transmit, send, or otherwise provide a comparison (or the difference metric, or both) between the ratings for presentation via the application 165. For example, the comparison may be presented as part of the prompt 224 or on the user interface 190 subsequent to the presentation of the prompt 224. The presentation of the comparison may be to reinforce the user 222 to the concept of experimentation in performing the activity regardless of the anticipated outcome. The presentation of the pre and post activity assessments may also challenge pre-conceptions and defeatist views to the user 222 with evidence of the user's own experiences that progressed differently from expectation. In some embodiments, the progress tracker 150 may provide the comparison or the difference metric as part of the subsequent package to be provided to the application 165.

With the updating of the user profile 160, the progress tracker 150 may modify, set, or change the endpoint to be achieved. In some embodiments, the progress tracker 150 may modify, set, or change the condition of the user 222 based on the information parsed from the response data 282. The information may include the responses received via the prompt 224. The progress tracker 150 may replace, change, or otherwise set the endpoint or the condition of the user 222 indicated in the user profile 160 with the endpoint or the condition respectively as indicated in the response data 282. The changing of the endpoint and the condition may result in the changing of the parameters 226 in the user profile 160. In some embodiments, the progress tracker 150 may calculate, determine, or generate new measures based on the updated parameters 226. The generation of the measures using the parameters 226 may be performed in a similar manner as discussed above. For example, the progress tracker 150 may use a function to calculate values for the characteristic of the user 222 and the likelihood that the user 222 will perform a given routine, among others. Upon generation, the progress tracker 150 may store and maintain the new measures with the user profile 160 on the database 115.

The configuration selector 135 may select, identify, or otherwise determine one or more new endpoints for the user 222. The identification of the endpoints (and activities associated with the endpoint) may be in a similar manner as discussed above, and may be based on the parameters 226 of the user profile 160 and the selection criterion 210. For example, the change to the user profile 160 may include the update in the state 204 or the level 208 or the indication of successful completion or the increase in the duration or the frequency for the routine. In this case, the configuration selector 135 may select a next endpoint, with activities of an increased duration and frequency. In contrast, the change to the user profile 160 may include the update in the state 204 or the level 208 or the indication of a failure to complete or decrease in the duration or the frequency for the routine. In this scenario, the configuration selector 135 may select the routine with a decreased duration and frequency. Continuing on, the change to the user profile 160 may include a modification in the endpoint or the condition of the user 222. Based on this change, the configuration selector 135 may select activities for the new endpoint or condition.

In some embodiments, the configuration selector 135 may select the new endpoints (or activities) for the user 222 using information derived from the response data 282 received via the prompt 224. The information may include those generated by the progress tracker 150 from the response data 282. In some embodiments, the configuration selector 135 may identify or select the new endpoint based on the state of the user 222 (e.g., mood, emotional, behavioral, or physiological state) as indicated in the response data 282. For example, when the state of the user 222 indicates a sadness state, the configuration selector 135 may select an endpoint with the aim of soothing the user 222 while performing activities to address the condition of the user 222. In some embodiments, the configuration selector 135 may identify or select the new endpoint based on the personal values as identified by the user 222. For instance, the configuration selector 135 may select an endpoint aimed at providing activities related to adventure, self-care, or art as indicated in the response data 282.

With the determination of the new endpoints, the configuration selector 135 may select one or more configuration files 155 from the overall set of configuration files 155 to provide to the application 165. The selection of the configuration files 155 may be in a similar manner as discussed previously, using the newly selected endpoint or activities. In some embodiments, the configuration selector 135 may select one or more configuration files 155 based on the transition in levels 208. Using the selected configuration files 155, the configuration packager 140 may generate at least one new package 228'. The package 228' may be generated in a similar fashion as detailed above, and may include instructions for configuring functionalities to be performed on the application 165 in accordance with the routine logic 202 as defined by the configuration file 155. Upon generation, the configuration packager 140 may provide the package 228' with the newly selected configuration file 155 to the application 165. In turn, the application 165 may receive and load the package 228'. Using the package 228', the application 165 may repeat the operations as described above.

By selecting and providing configuration files 155 in this manner, the application configuration service 105 may configure the functionalities of the application 165 customized to the responses indicated by the user 222. The configuration files 155 may provide a greater range of experiences to the user 222 and a sequence of content via the content items 264 adapted to the state and interactions from the user 222 in accordance with the routine logic 202. The configuration files 155 thus may improve the quality of human-computer interaction (HCI) between the user 222 and the application 165. In the context of digital therapeutics, the configuration file 155 and the content items 264 identified therein may lead to higher user engagement with the application 165. With higher likelihood of interactivity, the digital therapeutic provided by the application 165 may have higher efficacy in addressing the condition and increased adherence of the user 222 with the digital therapeutic. The configuration files 155 may also decrease the consumption of computing resources (e.g., on both the user device 110 and the application configuration service 105) that would have otherwise been used to provide and load irrelevant content on the application 165. Furthermore, the configuration files 155 may also reduce resorting to having to update the application 165 itself to provide additional functionality, further saving computing resources. The configuration files 155 (and by extension the packages 228) may reduce the expenditure of network bandwidth from back-and-forth communications associated with requesting and retrieving the content.

Figure 3:
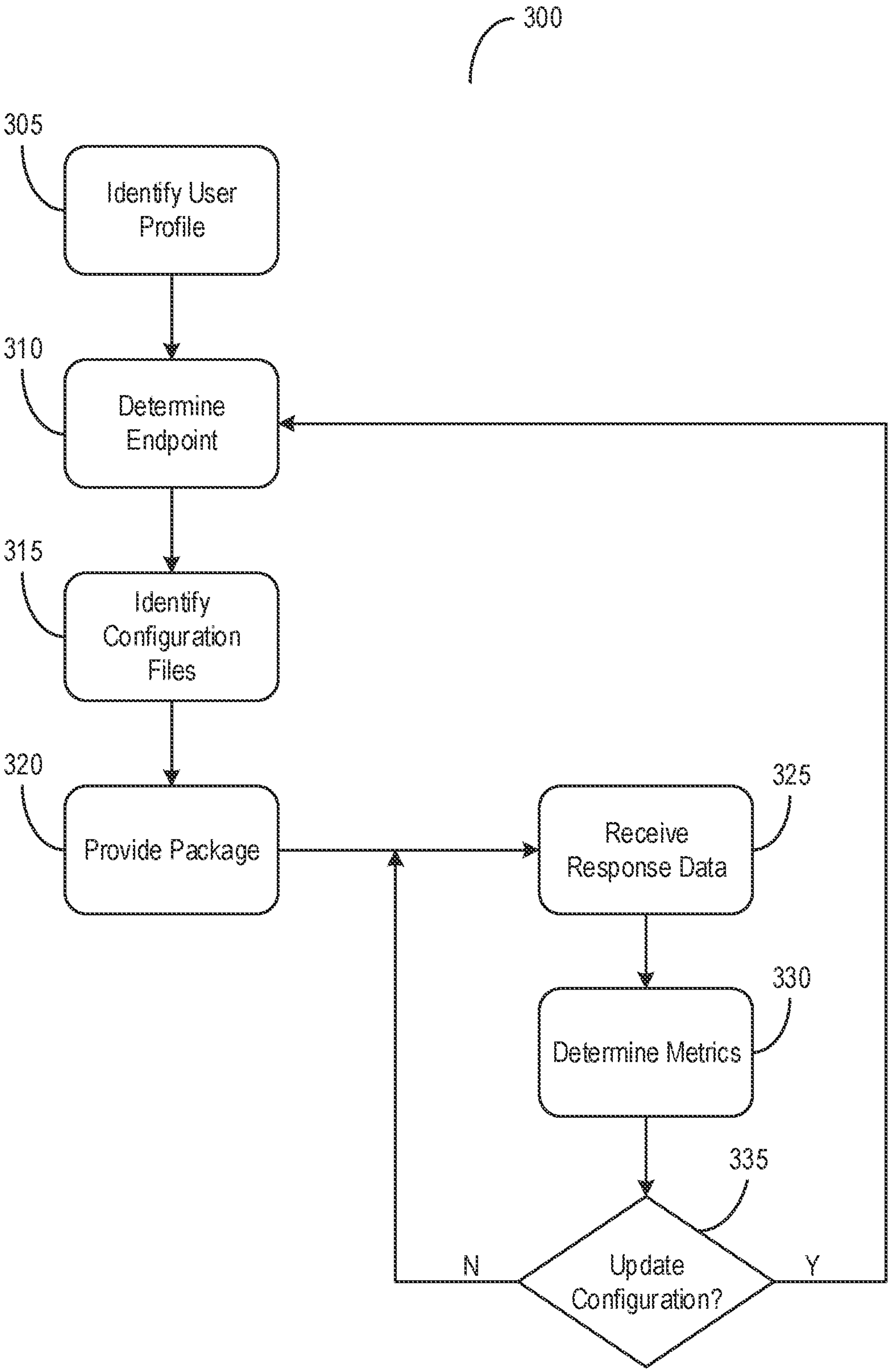
FIG. 3 depicts a flow diagram of a method of selecting configuration files for applications, in accordance with an illustrative embodiment.

Referring now to FIG. 3, depicted is a flow diagram of a method 300 of selecting configuration files for applications. The functionalities of method 300 may be implemented by using or performed by any of the components discussed herein in conjunction with FIGS. 1-2E, such as the application configuration service 105 and the user device 110, or FIG. 17, such as the computing system 1700. In overview, a server may identify a user profile (305). The server may determine an endpoint for the user (310). The server may identify configuration files (315). The server may provide a package (320). The server may receive response data (325). The server may determine metrics (330). The server may determine whether to update the configuration (335). If the determination is to update, the server may select new endpoints and repeat the functionalities from (310). Otherwise, if the determination is not to update, the server may wait for additional response data and repeat the functionalities from (325).

Figure 4:
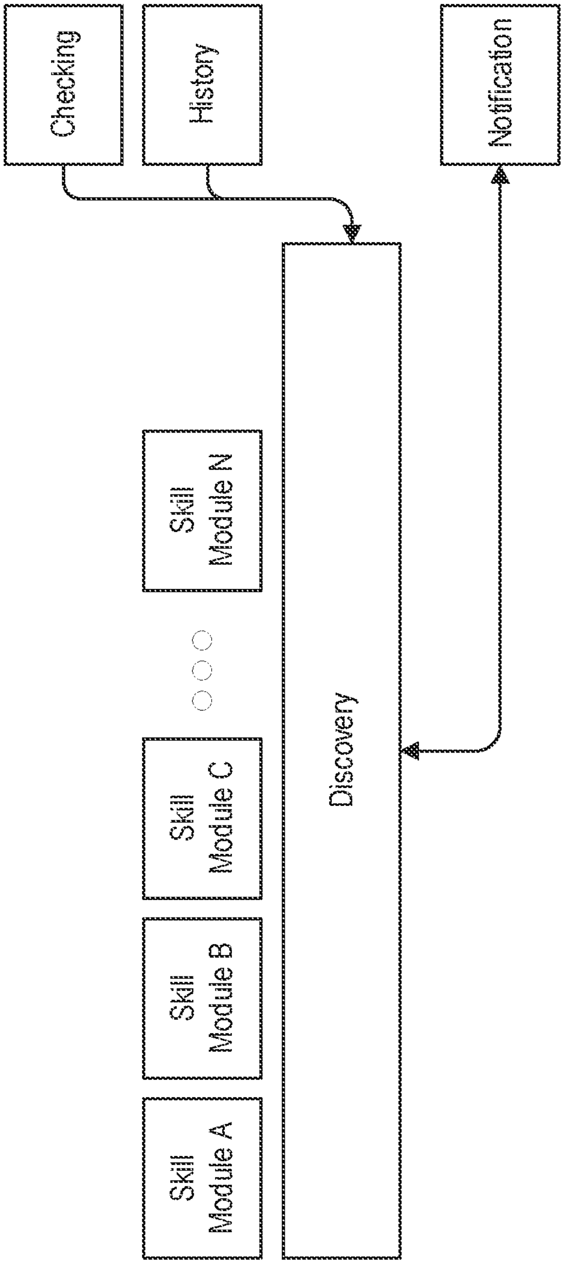
FIG. 4 depicts a block diagram of an architecture for a system for adaptive goal setting for selecting configuration files, in accordance with an illustrative embodiment.

Referring now to FIG. 4, depicted is a block diagram of an architecture for a system for adaptive goal setting for selecting configuration files. The architecture may be implemented using the components of the system 100, such as the application configuration service 105 and the application 165 on the user device 110. As depicted, the architecture may partition the adaptive goal setting (AGS) into three parts. First, the discovery component may select a skill (e.g., the endpoint) to be provided to the user. The selection may be based in part on user history. Second, the skills may be organized in corresponding modules A, B, C, N (e.g., in the form of the configuration files 155) for the user. All the logic for the skill may be included into the module, which may be self-contained, such that each time the module runs, the behavior of the module may be new and unique. Third, the notification component may be used to remind and encourage the user to perform the skills as organized in the modules. Subsequently, the discovery component may perform a check on the user to determine whether the user completed the skill modules. Based on the determination, the discovery component may select new skill modules, and the functionalities of the architecture may be repeated again.

Figure 5A:
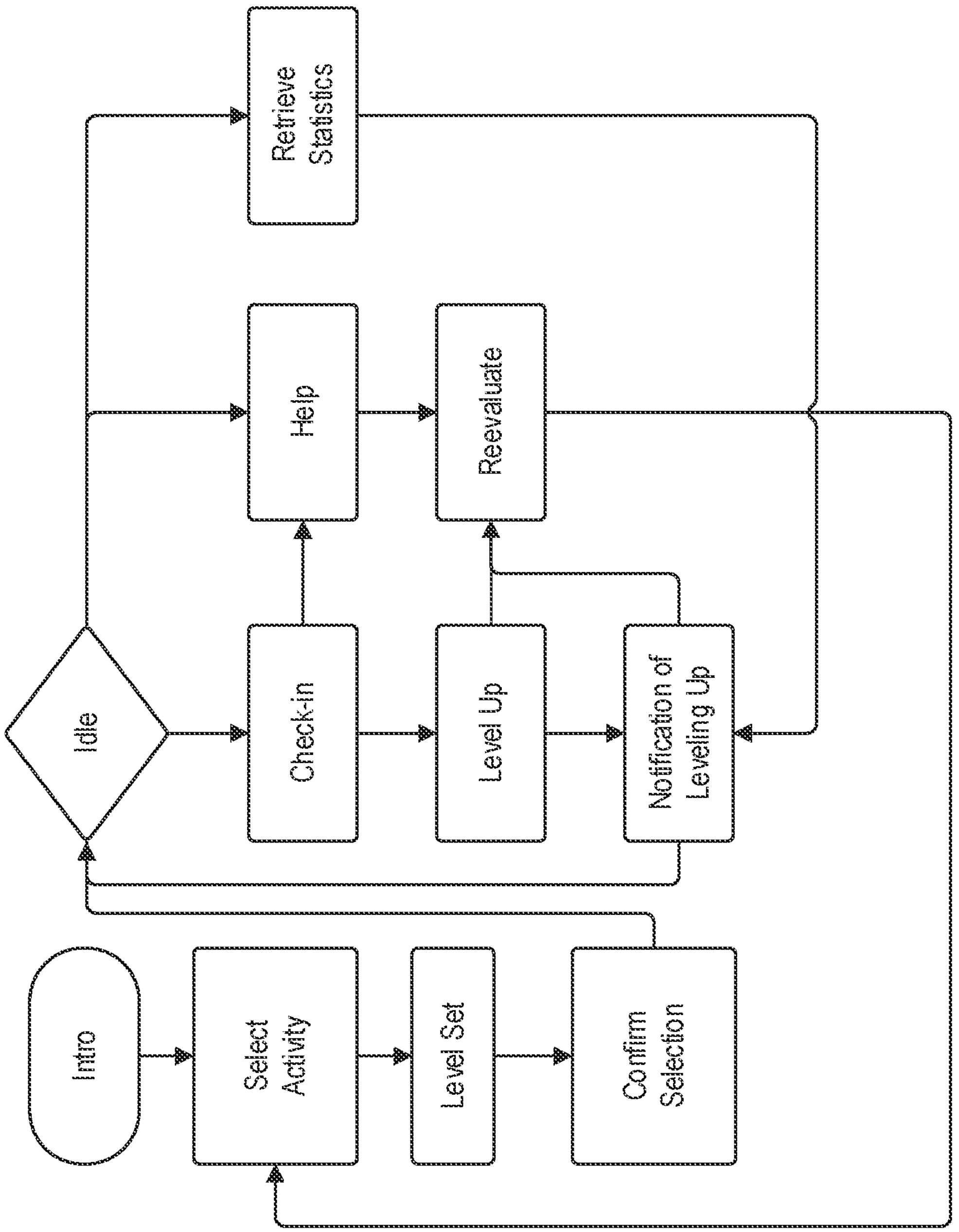
FIG. 5A depicts a flow diagram of a method of performing adaptive goal setting in selecting configuration files, in accordance with an illustrative embodiment.

Referring now to FIG. 5A, depicted is a flow diagram of a method of performing adaptive goal setting in selecting configuration files. The method may be performed or implemented using the components of the system 100, such as the application configuration service 105 and the user device 110. For example, at least one configuration file 155 may be used to define and carry out at least a portion of the depicted method. As illustrated, a system may present an introduction to a user. From the introduction, the system may receive selection of activities by the user. The system may set a level for the activities of the user. The user may confirm the selection of the level and the activities via interaction. The system may monitor user interactions to determine whether the user is idle. When idle, the system may check-in with the user to prompt the user to perform the activity. Upon completion, the system may update a level of the user, and proceed to notify the user of the update to the change in the level and perform a re-evaluation of the user. The system may also present a help prompt to instruct the user how to perform the activity. Depending on the results, the system may further perform a re-evaluation. In the meanwhile, the system may also retrieve statistics on the user with respect to the activities.

Figure 5B:
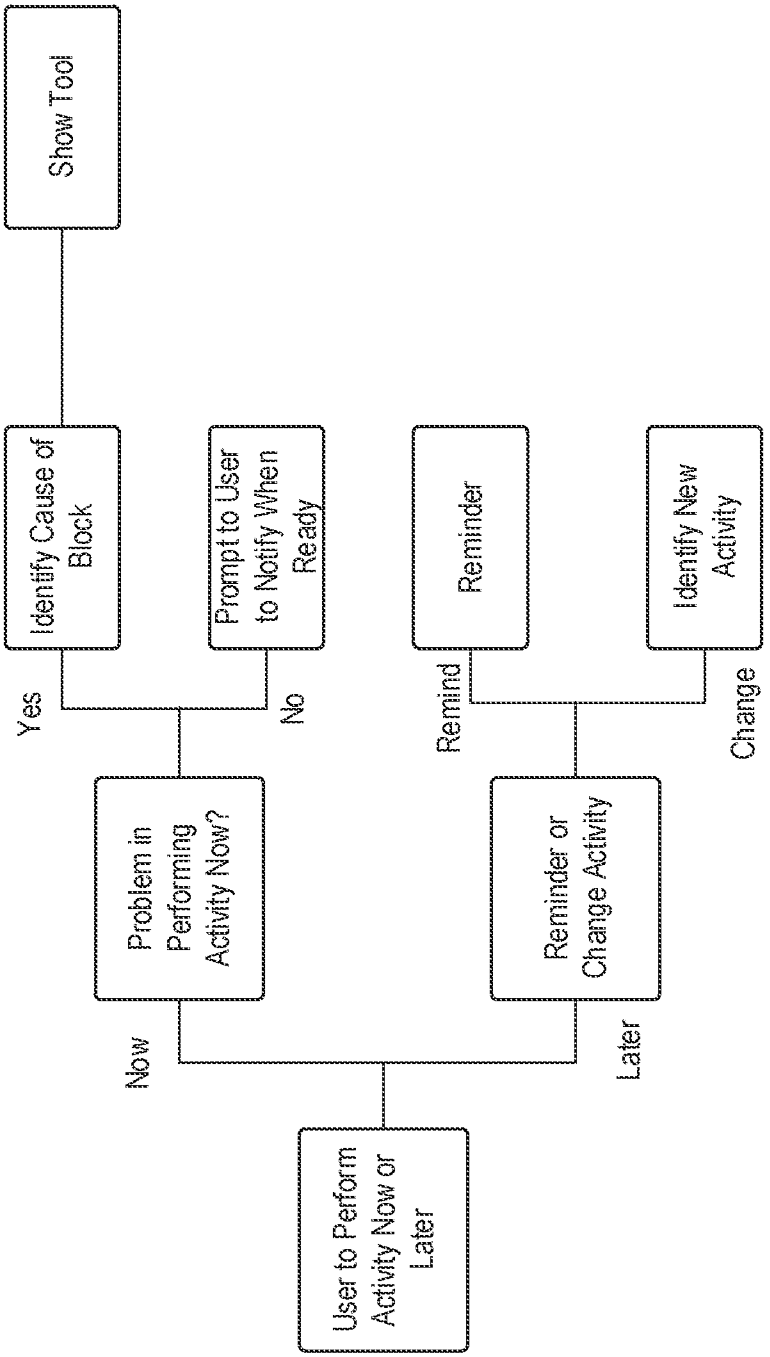
FIG. 5B depicts a flow diagram of a method of performing activities in accordance with the configuration files, in accordance with an illustrative embodiment.

Referring now to FIG. 5B, depicted is a flow diagram of a method of performing activities in accordance with the configuration files. The method may be performed or implemented using the components of the system 100, such as the application configuration service 105 and the user device 110. For example, at least one configuration file 155 may be used to define and carry out at least a portion of the depicted method. As illustrated, the system may determine whether the user is to perform an activity now (e.g., within a time window from the current time) or later (e.g., outside the time window from the current time). If the activity is to be performed now, the system may determine whether there is a problem in performing the activity now. If yes, the system may identify a cause of the blockage or hindrance and may show a tool (e.g., a user interface) to address the issue. On the other hand, if the activity is determined to be performed at a later point, the system may determine whether to provide a reminder or to change the activity. When the determination is to remind, the system may present a reminder. When the determination is to change, the system may identify a new activity.

B. Network and Computing Environment

Figure 20:
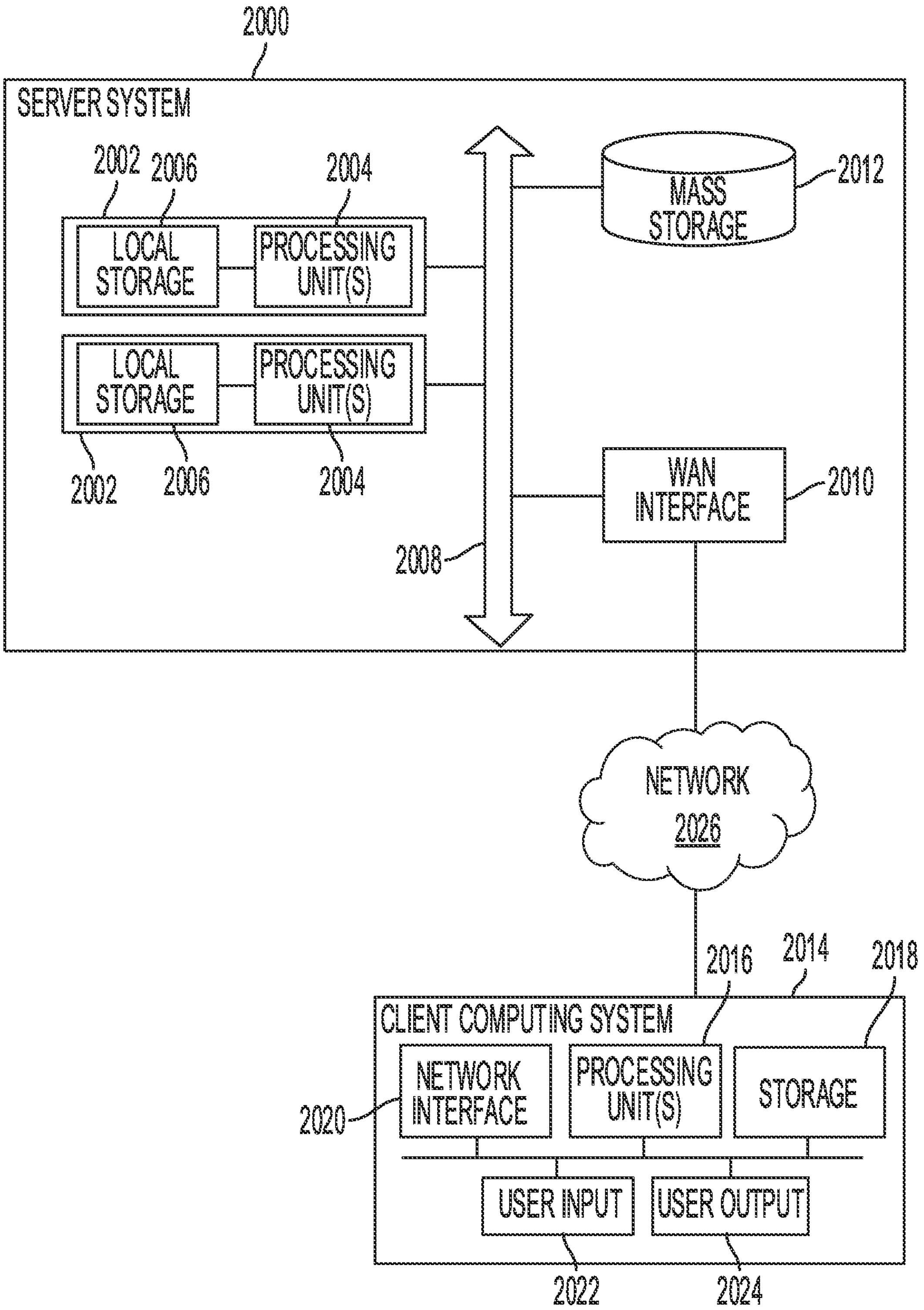
FIG. 20 is a block diagram of a server system and a client computer system in accordance with an illustrative embodiment.

Various operations described herein can be implemented on computer systems. FIG. 20 shows a simplified block diagram of a representative server system 2000, client computer system 2014, and network 2026 usable to implement certain embodiments of the present disclosure. In various embodiments, server system 2000 or similar systems can implement services or servers described herein or portions thereof. Client computer system 2014 or similar systems can implement clients described herein. The system 100 described herein can be similar to the server system 2000. Server system 2000 can have a modular design that incorporates a number of modules 2002 (e.g., blades in a blade server embodiment); while two modules 2002 are shown, any number can be provided. Each module 2002 can include processing unit(s) 2004 and local storage 2006.

Processing unit(s) 2004 can include a single processor, which can have one or more cores, or multiple processors. In some embodiments, processing unit(s) 2004 can include a general-purpose primary processor as well as one or more special-purpose co-processors such as graphics processors, digital signal processors, or the like. In some embodiments, some or all processing units 2004 can be implemented using customized circuits, such as application specific integrated circuits (ASICs) or field programmable gate arrays (FP- GAs). In some embodiments, such integrated circuits execute instructions that are stored on the circuit itself. In other embodiments, processing unit(s) 2004 can execute instructions stored in local storage 2006. Any type of processors in any combination can be included in processing unit(s) 2004.

Local storage 2006 can include volatile storage media (e.g., DRAM, SRAM, SDRAM, or the like) and/or non-volatile storage media (e.g., magnetic or optical disk, flash memory, or the like). Storage media incorporated in local storage 2006 can be fixed, removable, or upgradeable as desired. Local storage 2006 can be physically or logically divided into various subunits such as a system memory, a read-only memory (ROM), and a permanent storage device. The system memory can be a read-and-write memory device or a volatile read-and-write memory, such as dynamic random-access memory. The system memory can store some or all of the instructions and data that processing unit(s) 2004 need at runtime. The ROM can store static data and instructions that are needed by processing unit(s) 2004. The permanent storage device can be a non-volatile read-and-write memory device that can store instructions and data even when module 2002 is powered down. The term "storage medium" as used herein includes any medium in which data can be stored indefinitely (subject to overwriting, electrical disturbance, power loss, or the like) and does not include carrier waves and transitory electronic signals propagating wirelessly or over wired connections.

In some embodiments, local storage 2006 can store one or more software programs to be executed by processing unit(s) 2004, such as an operating system and/or programs implementing various server functions such as functions of the system 100 or any other system described herein, or any other server(s) associated with system 100 or any other system described herein.

"Software" refers generally to sequences of instructions that, when executed by processing unit(s) 2004, cause server system 2000 (or portions thereof) to perform various operations, thus defining one or more specific machine embodiments that execute and perform the operations of the software programs. The instructions can be stored as firmware residing in read-only memory and/or program code stored in non-volatile storage media that can be read into volatile working memory for execution by processing unit(s) 2004. Software can be implemented as a single program or a collection of separate programs or program modules that interact as desired. From local storage 2006 (or non-local storage described below), processing unit(s) 2004 can retrieve program instructions to execute and data to process in order to execute various operations described above.

In some server systems 2000, multiple modules 2002 can be interconnected via a bus or other interconnect 2008, forming a local area network that supports communication between modules 2002 and other components of server system 2000. Interconnect 2008 can be implemented using various technologies including server racks, hubs, routers, etc.

A wide area network (WAN) interface 2010 can provide data communication capability between the local area network (e.g., through the interconnect 2008) and the network 2026, such as the Internet. Other technologies can be used to communicatively couple the server system 2010 with the network 2026, including wired (e.g., Ethernet, IEEE 802.3 standards) and/or wireless technologies (e.g., Wi-Fi, IEEE 802.11 standards).

In some embodiments, local storage 2006 is intended to provide working memory for processing unit(s) 2004, providing fast access to programs and/or data to be processed while reducing traffic on interconnect 2008. Storage for larger quantities of data can be provided on the local area network by one or more mass storage subsystems 2012 that can be connected to interconnect 2008. Mass storage subsystem 2012 can be based on magnetic, optical, semiconductor, or other data storage media. Direct attached storage, storage area networks, network-attached storage, and the like can be used. Any data stores or other collections of data described herein as being produced, consumed, or maintained by a service or server can be stored in mass storage subsystem 2012. In some embodiments, additional data storage resources may be accessible via WAN interface 2010 (potentially with increased latency).

Server system 2000 can operate in response to requests received via WAN interface 2010. For example, one of modules 2002 can implement a supervisory function and assign discrete tasks to other modules 2002 in response to received requests. Work allocation techniques can be used. As requests are processed, results can be returned to the requester via WAN interface 2010. Such operation can generally be automated. Further, in some embodiments, WAN interface 2010 can connect multiple server systems 2000 to each other, providing scalable systems capable of managing high volumes of activity. Other techniques for managing server systems and server farms (collections of server systems that cooperate) can be used, including dynamic resource allocation and reallocation.

Server system 2000 can interact with various user-owned or user-operated devices via a wide-area network such as the Internet. An example of a user-operated device is shown in FIG. 20 as client computing system 2014. Client computing system 2014 can be implemented, for example, as a consumer device such as a smartphone, other mobile phone, tablet computer, wearable computing device (e.g., smart watch, eyeglasses), desktop computer, laptop computer, and so on.

For example, client computing system 2014 can communicate via WAN interface 2010. Client computing system 2014 can include computer components such as processing unit(s) 2016, storage device 2018, network interface 2020, user input device 2022, and user output device 2024. Client computing system 2014 can be a computing device implemented in a variety of form factors, such as a desktop computer, laptop computer, tablet computer, smartphone, other mobile computing device, wearable computing device, or the like.

Processor 2016 and storage device 2018 can be similar to processing unit(s) 2004 and local storage 2006 described above. Suitable devices can be selected based on the demands to be placed on client computing systems; for example, client computing system 2014 can be implemented as a "thin" client with limited processing capability or as a high-powered computing device. Client computing system 2014 can be provisioned with program code executable by processing unit(s) 2016 to enable various interactions with server system 2000.

Network interface 2020 can provide a connection to the network 2026, such as a wide area network (e.g., the Internet) to which WAN interface 2010 of server system 2000 is also connected. In various embodiments, network interface 2020 can include a wired interface (e.g., Ethernet) and/or a wireless interface implementing various RF data communication standards such as Wi-Fi, Bluetooth, or cellular data network standards (e.g., 3G, 4G, 5G, 20G, LTE, etc.).

User input device 2022 can include any device (or devices) via which a user can provide signals to client computing system 2014; client computing system 2014 can interpret the signals as indicative of particular user requests or information. In various embodiments, user input device 2022 can include any or all of a keyboard, touch pad, touch screen, mouse or other pointing device, scroll wheel, click wheel, dial, button, switch, keypad, microphone, and so on.

User output device 2024 can include any device via which client computing system 2014 can provide information to a user. For example, user output device 2024 can include display-to-display images generated by or delivered to client computing system 2014. The display can incorporate various image generation technologies, e.g., a liquid crystal display (LCD), light-emitting diode (LED) including organic light-emitting diodes (OLED), projection system, cathode ray tube (CRT), or the like, together with supporting electronics (e.g., digital-to-analog or analog-to-digital converters, signal processors, or the like). Some embodiments can include a device such as a touchscreen that function as both input and output device. In some embodiments, other user output devices 2024 can be provided in addition to or instead of a display. Examples include indicator lights, speakers, tactile "display" devices, printers, and so on.

Some embodiments include electronic components, such as microprocessors, storage and memory that store computer program instructions in a computer readable storage medium. Many of the features described in this specification can be implemented as processes that are specified as a set of program instructions encoded on a computer readable storage medium. When these program instructions are executed by one or more processing units, they cause the processing unit(s) to perform various operations indicated in the program instructions. Examples of program instructions or computer code include machine code, such as is produced by a compiler, and files including higher-level code that are executed by a computer, an electronic component, or a microprocessor using an interpreter. Through suitable programming, processing unit(s) 2004 and 2016 can provide various functionality for server system 2000 and client computing system 2014, including any of the functionality described herein as being performed by a server or client, or other functionality.

It will be appreciated that server system 2000 and client computing system 2014 are illustrative and that variations and modifications are possible. Computer systems used in connection with embodiments of the present disclosure can have other capabilities not specifically described here. Further, while server system 2000 and client computing system 2014 are described with reference to particular blocks, it is to be understood that these blocks are defined for convenience of description and are not intended to imply a particular physical arrangement of component parts. For instance, different blocks can be but need not be located in the same facility, in the same server rack, or on the same motherboard. Further, the blocks need not correspond to physically distinct components. Blocks can be configured to perform various operations, e.g., by programming a processor or providing appropriate control circuitry, and various blocks might or might not be reconfigurable depending on how the initial configuration is obtained. Embodiments of the present disclosure can be realized in a variety of apparatus including electronic devices implemented using any combination of circuitry and software.

While the disclosure has been described with respect to specific embodiments, one skilled in the art will recognize that numerous modifications are possible. Embodiments of the disclosure can be realized using a variety of computer systems and communication technologies including but not limited to specific examples described herein. Embodiments of the present disclosure can be realized using any combination of dedicated components and/or programmable processors and/or other programmable devices. The various processes described herein can be implemented on the same processor or different processors in any combination. Where components are described as being configured to perform certain operations, such configuration can be accomplished; e.g., by designing electronic circuits to perform the operation, by programming programmable electronic circuits (such as microprocessors) to perform the operation, or any combination thereof. Further, while the embodiments described above may make reference to specific hardware and software components, those skilled in the art will appreciate that different combinations of hardware and/or software components may also be used and that particular operations described as being implemented in hardware might also be implemented in software or vice versa.

Computer programs incorporating various features of the present disclosure may be encoded and stored on various computer readable storage media; suitable media include magnetic disk or tape, optical storage media such as compact disk (CD) or digital versatile disk (DVD), flash memory, and other non-transitory media. Computer readable media encoded with the program code may be packaged with a compatible electronic device, or the program code may be provided separately from electronic devices (e.g., via Internet download or as a separately packaged computer-readable storage medium).

Thus, although the disclosure has been described with respect to specific embodiments, it will be appreciated that the disclosure is intended to cover all modifications and equivalents within the scope of the following claims.

What is claimed is:

1. A method of selecting configuration files for applications, comprising:

maintaining, by a computing system, a plurality of configuration files for an application to address a condition in a user, each of the plurality of configuration files comprising respective instructions including a respective logic to define placement of a respective set of content items associated with one or more elements of a graphical user interface of the application, the respective logic comprising:

(i) a plurality of states, each state of the plurality of states identifying at least one of the respective set of content items associated with the one or more elements of the graphical user interface to prompt users to perform at least one of a plurality of activities via the application towards achieving a respective endpoint of a plurality of endpoints, and (ii) a plurality of events, each event of the plurality of events identifying a respective interaction to be detected via an event bus of the application to change from a first state to a second state among the plurality of states;

determining, by the computing system, an endpoint of the plurality of endpoints associated with addressing the condition in the user, using one or more parameters associated with the user;

selecting, by the computing system, based on the endpoint for the user, from the plurality of configuration files, a configuration file comprising instructions including a logic to define placement of a set of content items associated with the one or more elements of the graphical user interface for an activity of the plurality of activities to be performed by the user;

generating, by the computing system and based on the configuration file, at least one package comprising machine-executable code;

transmitting, by the computing system, the at least one package to the application;

parsing, by the application, the at least one package to invoke the logic of the configuration file to cause the application to display a selectable first element on the graphical user interface;

automatically inserting, by the application, in accordance with one or more criteria, a selectable second element onto the graphical user interface, wherein a selection of the selectable second element by the user causes display of at least one of the set of content items;

monitoring, via the event bus, one or more interactions by the user in accordance with the logic;

updating, by the computing system, based on a transition from the first state to the second state and based on the one or more interactions, the logic of the configuration file to define placement of the set of content items as one or more elements of the graphical user interface of the application; and responsive to updating the configuration file, causing, by the computing system, placement of at least one of the set of content items corresponding to the second state associated with one or more elements of the graphical user interface corresponding to the endpoint.

2. The method of claim 1, further comprising:

receiving, by the computing system, from the application, response data identifying one or more interactions by the user with the set of content items presented via the application towards achieving the endpoint;

determining, by the computing system, a second endpoint of the plurality of endpoints based on the response data for the endpoint; and selecting, by the computing system, from the plurality of configuration files, a second configuration file based on the second endpoint to provide to the application.

3. The method of claim 1, further comprising:

identifying, by the computing system, from a profile of the user, a first level of a plurality of levels towards achieving the endpoint;

determining, by the computing system, a transition from the first level to a second level, based on response data identifying one or more interactions by the user with the set of content items presented via the application; and selecting, by the computing system, from the plurality of configuration files, a second configuration file based on the transition to the second level.

4. The method of claim 3, wherein determining the transition further comprises determining, based on a performance of the activity of the user towards achieving the endpoint, whether to transition to the first level or the second level of the plurality of levels towards achieving a second endpoint.

5. The method of claim 1, wherein each of the plurality of configuration files identifies a respective criterion defining a first measure of the user to select a corresponding configuration file identifying the set of content items to prompt users to perform the activity, and further comprising:

determining, by the computing system, a second measure based on a profile of the user, the second measure identifying at least one of: (i) a likelihood that the user is to perform the activity or (ii) a predicted efficacy of the activity on the user towards achieving the endpoint; and identifying, by the computing system, from the plurality of activities, the activity based on a comparison of the first measure with the second measure.

6. The method of claim 1, further comprising:

receiving, by the computing system, from the application, a response identifying a mood of the user in response to presentation of a prompt via the application at a defined time, and identifying, by the computing system, from the plurality of activities, the activity based on the mood of the user indicated in the response.

7. The method of claim 1, further comprising:

receiving, by the computing system, from the application, a response identifying a plurality of personal values of the user, and identifying, by the computing system, from the plurality of activities, the activity based on the plurality of personal values associated with the user identified in the response.

8. The method of claim 7, further comprising:

determining, by the computing system, a progression metric based on performance of the activity towards achieving the endpoint; and presenting, by the computing system, via the application, a connection between the progression metric and the plurality of personal values associated with the user.

9. The method of claim 1, further comprising:

presenting, by the computing system, via the application, a prompt for the user to indicate a first rating associated with the activity prior to performance of the activity via the application; and storing, by the computing system, a response identifying the first rating associated with the activity from the application.

10. The method of claim 9, further comprising:

presenting, by the computing system, via the application, a prompt for the user to indicate a second rating associated with the activity subsequent to performance of the activity via the application; and presenting, by the computing system, via the application, a comparison of the second rating with the first rating.

11. The method of claim 1, wherein determining the endpoint further comprises determining, from the plurality of endpoints, the endpoint based on at least one of (i) a baseline assessment and (ii) an indication by the user requesting an activity towards achieving the endpoint.

12. The method of claim 1, wherein at least one configuration file of the plurality of configuration files defines a finite state machine, the finite state machine identifying:

the plurality of states including at least the first state and the second state, each of which corresponds to an intensity level for a corresponding activity and specifies an output, the output identifying one or more of the respective set of content items to present via a user interface of the application, and the plurality of events, each of the plurality of events identifying the respective event corresponding to the interaction to be performed via the application for the corresponding activity.

13. The method of claim 1, wherein the plurality of endpoints is associated with at least one of a plurality of classifications for endpoints.

14. The method of claim 13, wherein a first subset of the plurality of endpoints is associated with a first classification and a second subset of the plurality of endpoints is associated with a second classification.

15. The method of claim 1, wherein the user is on a medication to address the condition, at least partially in concurrence with performance of the activity via the application, wherein the condition includes a mental illness.

16. A system for selecting configuration files for applications, comprising a computing system having one or more processors coupled with memory, an application, wherein the system is configured to:

maintain a plurality of configuration files for an application to address a condition in a user, each of the plurality of configuration files comprising respective instructions including a respective logic to define placement of a respective set of content items associated with one or more elements of a graphical user interface of the application, the respective logic comprising:

(i) a plurality of states, each state of the plurality of states identifying at least one of the respective set of content items associated with the one or more elements of the graphical user interface to prompt users to perform at least one of a plurality of activities via the application towards achieving a respective endpoint of a plurality of endpoints, and (ii) a plurality of events, each event of the plurality of events identifying a respective interaction to be detected via an event bus of the application to change from a first state to a second state among the plurality of states;

determine an endpoint of the plurality of endpoints associated with addressing the condition in the user, using one or more parameters associated with the user;

select, based on the endpoint for the user, from the plurality of configuration files, a configuration file comprising instructions including a logic to define placement of a set of content items associated with the one or more elements of the graphical user interface for an activity of the plurality of activities to be performed by the user;

generate, based on the configuration file, at least one package comprising machine-executable code;

transmit the at least one package to the application;

parse the at least one package to invoke the logic of the configuration file to cause the application to display a selectable first element on the graphical user interface;

automatically insert, in accordance with one or more criteria, a selectable second element onto the graphical user interface, wherein a selection of the selectable second element by the user causes display of at least one of the set of content items;

monitor, via the event bus, one or more interactions by the user in accordance with the logic;

update, based on a transition from the first state to the second state and based on the one or more interactions, the logic of the configuration file to define placement of the set of content items as one or more elements of the graphical user interface of the application; and responsive to updating the configuration file, cause placement of at least one of the set of content items corresponding to the second state associated with one or more elements of the graphical user interface corresponding to the endpoint.

17. The system of claim 16, wherein the computing system is further configured to:

receive, from the application, response data identifying one or more interactions by the user with the set of content items presented via the application towards achieving the endpoint;

determine a second endpoint of the plurality of endpoints based on the response data for the endpoint; and select, from the plurality of configuration files, a second configuration file based on the second endpoint to provide to the application.

18. The system of claim 16, wherein the computing system is further configured to:

identify, from a profile of the user, a first level of a plurality of levels towards achieving the endpoint;

determine a transition from the first level to a second level, based on response data identifying one or more interactions by the user with the set of content items presented via the application; and select, from the plurality of configuration files, a second configuration file based on the transition to the second level.

19. The system of claim 18, wherein the computing system is further configured to determine, based on a performance of the activity of the user towards achieving the endpoint, whether to transition to the first level or the second level of the plurality of levels towards achieving a second endpoint.

20. The system of claim 16, wherein each of the plurality of configuration files identifies a respective criterion defining a first measure of the user to select a corresponding configuration file identifying the set of content items to prompt users to perform the activity, and wherein the computing system is further configured to:

determine a second measure based on a profile of the user, the second measure identifying at least one of: (i) a likelihood that the user is to perform the activity or (ii) a predicted efficacy of the activity on the user towards achieving the endpoint; and identify, from the plurality of activities, the activity based on a comparison of the first measure with the second measure.

21. The system of claim 16, wherein the computing system is further configured to:

receive, from the application, a response identifying a mood of the user in response to presentation of a prompt via the application at a defined time, and identify, from the plurality of activities, the activity based on the mood of the user indicated in the response.

22. The system of claim 16, wherein the computing system is further configured to:

receive, from the application, a response identifying a plurality of personal values of the user, and identify, from the plurality of activities, the activity based on the plurality of personal values associated with the user identified in the response.

23. The system of claim 22, wherein the computing system is further configured to:

determine a progression metric based on performance of the activity towards achieving the endpoint; and present, via the application, a connection between the progression metric and the plurality of personal values associated with the user.

24. The system of claim 16, wherein the computing system is further configured to:

present, via the application, a prompt for the user to indicate a first rating associated with the activity prior to performance of the activity via the application; and store a response identifying the first rating associated with the activity from the application.

25. The system of claim 24, wherein the computing system is further configured to:

present, via the application, a prompt for the user to indicate a second rating associated with the activity subsequent to performance of the activity via the application; and present, via the application, a comparison of the second rating with the first rating.

26. The system of claim 16, wherein the computing system is further configured to determine, from the plurality of endpoints, the endpoint based on at least one of (i) a baseline assessment and (ii) an indication by the user requesting an activity towards achieving the endpoint.

27. The system of claim 16, wherein at least one configuration file of the plurality of configuration files defines a finite state machine, the finite state machine identifying:

the plurality of states including at least the first state and the second state, each of which corresponds to an intensity level for a corresponding activity and specifies an output, the output identifying one or more of the respective set of content items to present via a user interface of the application, and the plurality of events each identifying the respective event corresponding to the interaction to be performed via the application for the corresponding activity.

28. The system of claim 16, wherein the plurality of endpoints is associated with at least one of a plurality of classifications for endpoints.

29. The system of claim 28, wherein a first subset of the plurality of endpoints is associated with a first domain and a second subset of the plurality of endpoints is associated with a second domain.

30. The system of claim 16, wherein the user is on a medication to address the condition, at least partially in concurrence with performance of the activity via the application, wherein the condition includes a mental illness.

31. The method of claim 1, further comprising:

identifying, by the computing system, from a profile of the user, a first stage of a plurality of stages towards achieving the endpoint;

determining, by the computing system, a transition from the first stage to a second stage, based on response data identifying one or more interactions by the user with the set of content items presented via the application; and selecting, by the computing system, from the plurality of configuration files, a second configuration file based on the transition to the second stage.

32. The method of claim 31, wherein determining the transition further comprises determining, based on a performance of the activity of the user towards achieving the endpoint, whether to transition to the first stage or the second stage of the plurality of stages towards achieving a second endpoint.

33. The system of claim 16, wherein the computing system is further configured to:

identify, from a profile of the user, a first stage of a plurality of stages towards achieving the endpoint;

determine a transition from the first stage to a second stage, based on response data identifying one or more interactions by the user with the set of content items presented via the application; and select, from the plurality of configuration files, a second configuration file based on the transition to the second stage.

34. The system of claim 33, wherein the computing system is further configured to determine, based on a performance of the activity of the user towards achieving the endpoint, whether to transition to the first stage or the second stage of the plurality of stages towards achieving a second endpoint.

35. The method of claim 31, wherein the plurality of stages is associated with at least one of: time, progress, difficulty, activity duration, activity frequency, activity type, and endpoint.

36. The method of claim 31, wherein the plurality of stages comprises a plurality of levels based on difficulty.

37. The system of claim 33, wherein the plurality of stages is associated with at least one of: time, progress, difficulty, activity duration, activity frequency, activity type, and endpoint.

38. The system of claim 33, wherein the plurality of stages comprises a plurality of levels based on difficulty.

* * * * *